US011877958B2

United States Patent
Bos et al.

(10) Patent No.: US 11,877,958 B2
(45) Date of Patent: Jan. 23, 2024

(54) ACCOMMODATIVE LENS DEVICE

(71) Applicant: KEJAKO SA, Plan-les-Ouates (CH)

(72) Inventors: Gilles Bos, Plan-les-Ouates (CH); Aurélien Maurer, Plan-les-Ouates (CH); David Enfrun, Plan-les-Ouates (CH); Michael Assouline, Plan-les-Ouates (CH); Pierre-Francois Isard, Plan-les-Ouates (CH); Pierre-Yves Maitre, Plan-les-Ouates (CH); Gabriel Delage, Plan-les-Ouates (CH); Charles-Olivier Zuber, Plan-les-Ouates (CH); Mario Carta, Plan-les-Ouates (CH); Moïse Seguin, Plan-les-Ouates (CH); Quentin Guyot, Plan-les-Ouates (CH)

(73) Assignee: KEJAKO SA, Plan-les-Ouates (CH)

( * ) Notice: Subject to any disclaimer, the term of this patent is extended or adjusted under 35 U.S.C. 154(b) by 984 days.

(21) Appl. No.: 16/493,130

(22) PCT Filed: Mar. 13, 2018

(86) PCT No.: PCT/EP2018/056305
§ 371 (c)(1),
(2) Date: Sep. 11, 2019

(87) PCT Pub. No.: WO2018/167099
PCT Pub. Date: Sep. 20, 2018

(65) Prior Publication Data
US 2020/0113736 A1 Apr. 16, 2020

(30) Foreign Application Priority Data

Mar. 13, 2017 (EP) ..................... 17160516
Mar. 13, 2017 (EP) ..................... 17160686

(51) Int. Cl.
A61F 2/16 (2006.01)
A61F 9/008 (2006.01)
G06T 17/00 (2006.01)

(52) U.S. Cl.
CPC ........ A61F 9/00834 (2013.01); A61F 2/1635 (2013.01); A61F 2/1694 (2013.01); G06T 17/00 (2013.01); A61F 2009/0087 (2013.01)

(58) Field of Classification Search
CPC ... A61F 2/1635; A61F 2/1694; A61F 9/00834
See application file for complete search history.

(56) References Cited

U.S. PATENT DOCUMENTS

2002/0188351 A1* 12/2002 Laguette ............... A61F 2/1635
623/6.37
2005/0021139 A1* 1/2005 Shadduck ............ A61F 2/1694
623/6.37

FOREIGN PATENT DOCUMENTS

CN 101868196 A 10/2010
EP 0166051 A1 1/1986

OTHER PUBLICATIONS

CN Office Action dated Mar. 29, 2021.
* cited by examiner

Primary Examiner — Javier G Blanco
(74) Attorney, Agent, or Firm — IPSILON USA, LLP

(57) ABSTRACT

The invention concerns an implant that comprises an anterior part and a posterior part extending along a longitudinal axis and having respectively an anterior (A) and a posterior pole (E) both located on axis. The anterior and posterior parts extend each radially relative to axis, on either side thereof, the anterior and posterior parts having each two portions located on both sides of axis respectively when viewed in a sagittal plane. Each portion of the anterior part has a radial extension that increases from anterior pole (A) to a point (B, B') where the anterior part ends and the posterior part begins, each portion of the posterior part having a radial extension decreasing from point (B, B') to the posterior pole (E). The outer outline of each portion of the anterior part forms a curve having a radius of curvature that is greater at anterior pole (A) than at point (B, B'). The implant is made of one or more materials that have elastic or visco-elastic and cohesive properties in a solid state such that the shear modulus is between 10 Pa and 10 kPa.

6 Claims, 16 Drawing Sheets

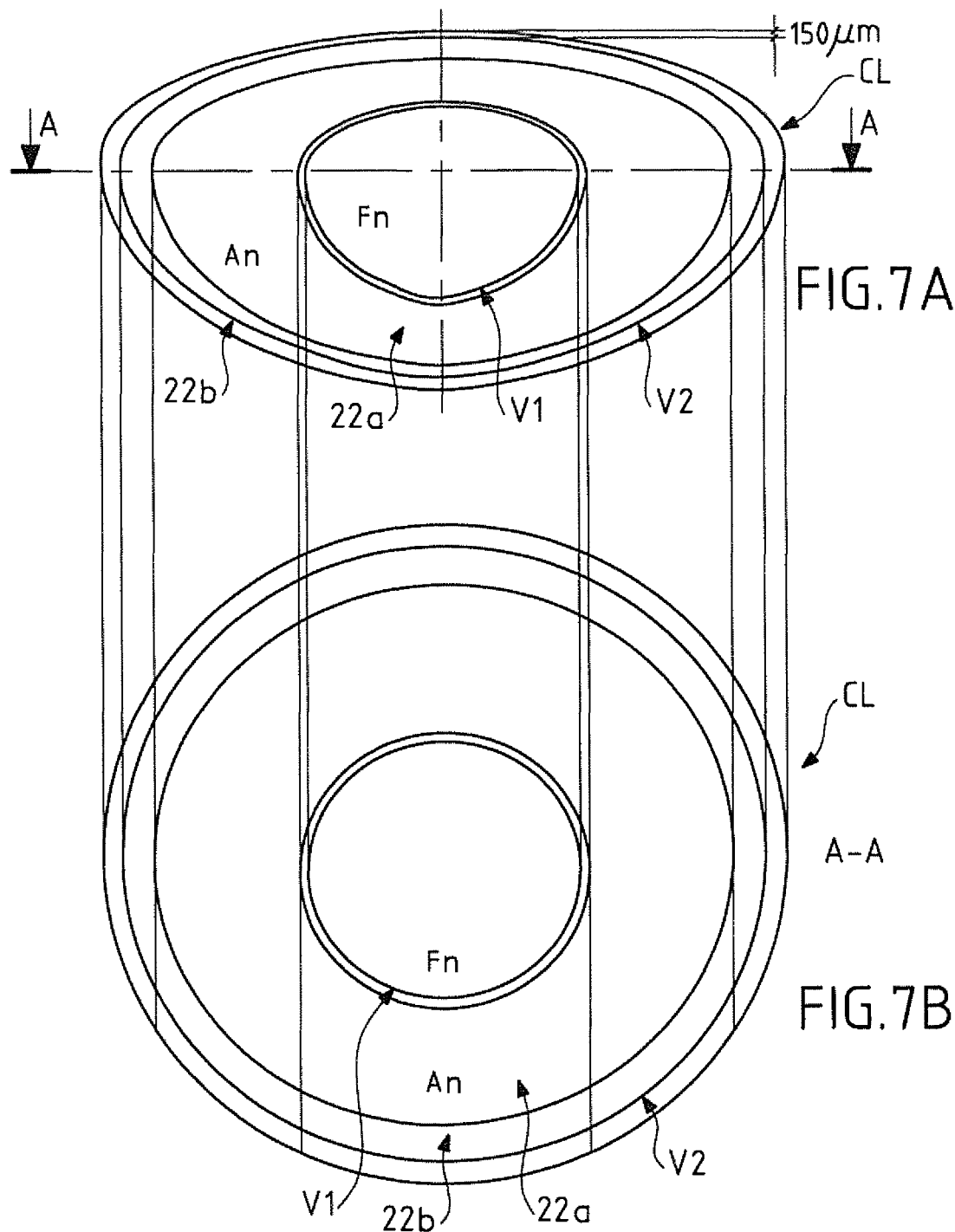

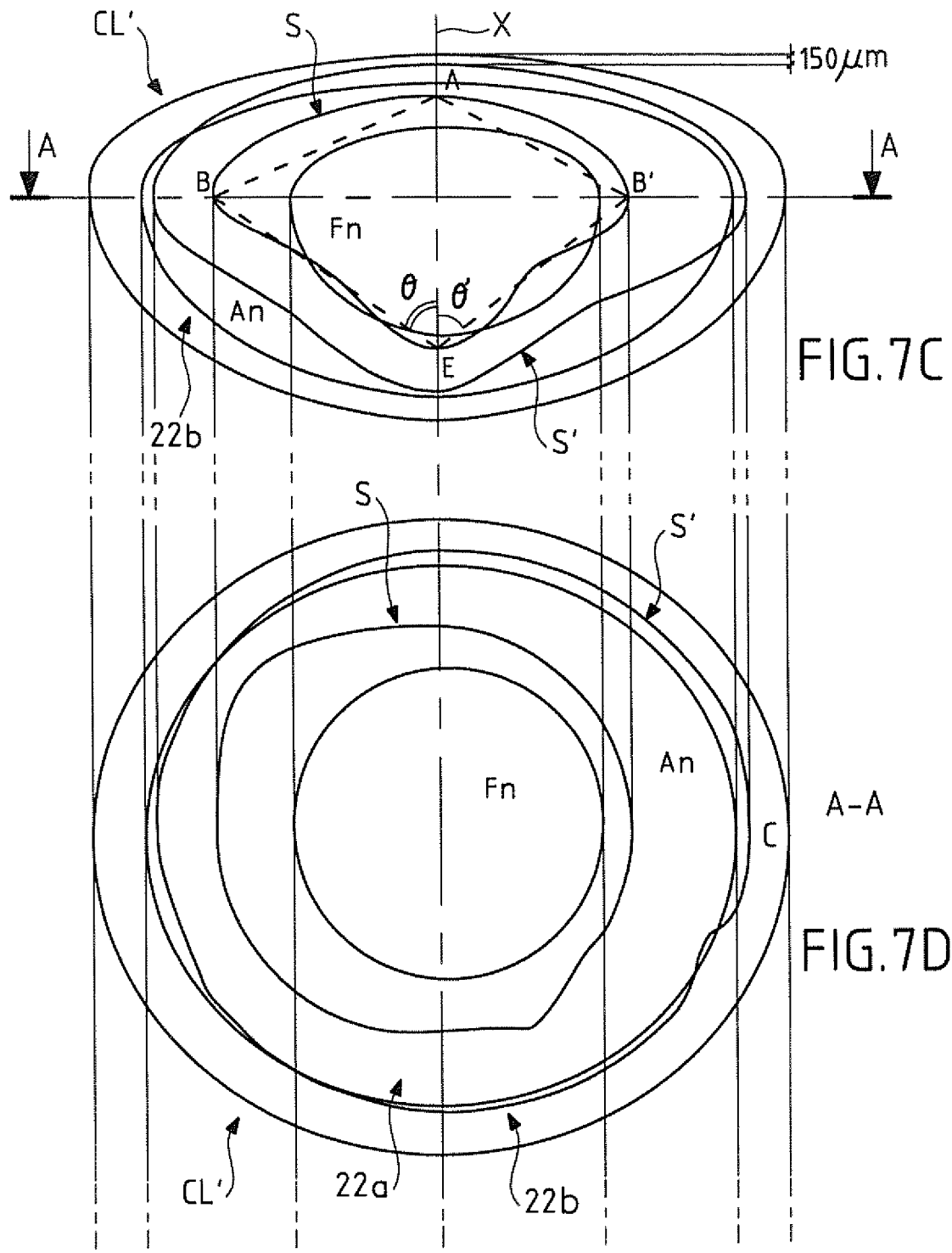

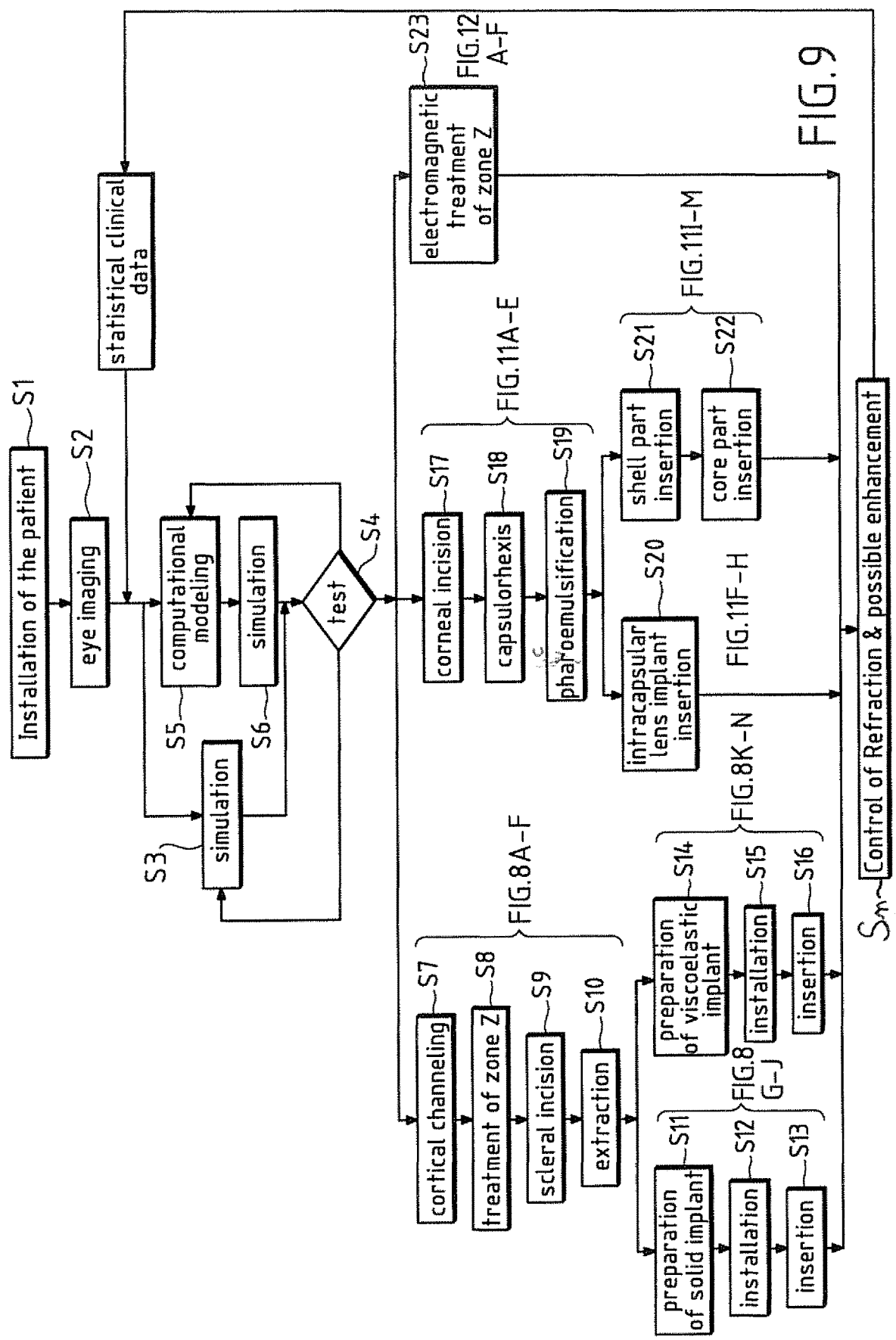

ACCOMMODATIVE LENS DEVICE

RELATED APPLICATION

This application is a National Phase of PCT/EP2018/056305 filed on Mar. 13, 2018, which claims the benefit of priority from European Patent Application Nos. 17 160 686.6, filed on Mar. 13, 2017, and 17 160 516.5, filed on Mar. 13, 2017 the entirety of which are incorporated by reference.

The invention concerns an accommodative lens device which may provide lens physical restoration, and more particularly, an intra cortical lens implant and an intra capsular lens implant.

DESCRIPTION OF RELATED ART

Presbyopia most often presents as a near vision deficiency, the inability to read small print, especially in dim lighting after about 40-45 years of age.

Presbyopia, or the loss of accommodative amplitude with age, relates to the eye's inability to change the shape of the natural crystalline lens, which allows a person to change focus between far and near, and occurs in essentially 100% of the population. Accommodative amplitude has been shown to decline with age steadily through the fifth decade of life.

Historically, studies have generally attributed loss of accommodation to the hardening of the crystalline tens with age and, more specifically, to an increase in the Young's Modulus of Elasticity of the lens material.

According to the Helmholtz theory, presbyopia is caused by increased stiffness of the lens with age which makes it harder to change the shape of the lens during accommodation and thus to focus the incoming light properly on to the retina.

More recent studies have examined the effect of aging on the relative change in material properties between the nucleus and the cortex. These studies have provided various theories and data with respect to the hardening of the lens. In a general manner, such studies have essentially proposed the theory according to which the loss of flexibility is the result of an increase in the Young's Modulus of Elasticity of the nucleus and/or cortex material. Such studies have viewed this hardening as the primary factor in the loss of accommodative amplitude with age and hence the cause of presbyopia.

Due to the phases of growth, the eye has various nuclei which differ in age and are superimposed on each other in an onion-like manner. The innermost and thus oldest nucleus hardens as it ages.

As the eye ages, there are also age related changes to these structures that include the development of intermolecular bonding, mostly disulfide bonding, the compaction of tissue, the breakdown of some of the original attachments, and the yellowing or darkening of older lens areas.

Actually, compaction of the lens occurs with aging. The number of lens fibers that grow every year is relatively constant throughout life. However, the size of the lens does not become as large as expected from new fiber growth. The lens grows from birth through age 3, from 6 mm to 7.2 mm or 20% growth in only three years. Then during the next approximate decade, growth is from 7.2 mm to 9 mm or 25%. However, this is over a three times longer period of 9 years. Over the next approximate two decades, from age 12 to age 36 the lens grows from 9 mm to 9.6 or 6.7% growth in 24 years, showing a dramatically slowing observed growth rate, while it is believed there is a relatively constant rate of fiber growth during this period. Finally, in the last approximately two decades described, from age 36 to age 54, the lens grows by a tiny fraction of its youthful growth, from 9.6 to 9.8 mm or 2.1% in 18 years. Although there is a geometry effect of needing more lens fibers to fill larger outer shells, the size of the older lens is considerably smaller than predicted by fiber growth rate models, which consider geometry effects. Fiber compaction including nuclear fiber compaction is thought to explain these observations.

Presbyopia may be corrected by the use of external optical correction devices including reading glasses, progressive spectacles, bifocal or trifocal lenses, contact lenses etc. However, many patients would like to avoid these external optical correction devices, especially the use of reading glasses considered as very troublesome.

All other commercially available products which may help restore accommodation are overall surgical and invasive.

A single method has been approved by the FDA as a temporary cure for presbyopia: conductive keratoplasty, e.g. as described in US 2007/038210. However, the effect only lasts for 3-6 months.

Another method, called lentotomy e.g. as described in US 2014/378955 and US 2010/191230 is based on cutting gliding planes inside the intact lens to allow for greater flexibility of the lens by the use of a femtosecond laser. This method is not commercially available.

None of the above methods has been satisfactory yet.

OBJECT AND SUMMARY

There still exists a need for an accommodative lens device, in particular an implant, which restores flexibility, and therefore increase visual accommodative amplitude, in a human eye.

There also exists a more general need for a new accommodative lens device which may remedy other optical disorders while providing actual dynamic visual accommodation.

According to a first aspect of the invention, a first embodiment concerns an intra cortical lens implant having a longitudinal axis corresponding to a polar axis of the intra cortical lens implant, wherein the intra cortical lens implant comprises an anterior part and a posterior part that extend axially along the polar axis, the anterior part having an anterior pole (A) located on the longitudinal axis and the posterior part having a posterior pole (E) located on the polar axis, the anterior part and the posterior part extending each radially relative to the polar axis on either side thereof, the anterior part and the posterior part having each two portions located on both sides of the polar axis respectively when viewed in a plane including the polar axis, called sagittal plane, each portion of the anterior part having a radial extension that increases from the anterior pole (A) to a point (B, B') where the anterior part ends and the posterior part begins, each portion of the posterior part having a radial extension that decreases from the point (B, B') where the posterior part begins to the posterior pole (E), the outer outline of each portion of the anterior part forming a curve having a radius of curvature that is greater at the anterior pole (A) than at the point (B, B'), the intra cortical lens implant being made of one or more materials that have elastic or visco-elastic and cohesive properties in a solid state such that the shear modulus is greater than 10 Pa and less than 10 kPa, the one or more materials having a refractive index that is suitable for being used in a crystalline lens.

This new intra cortical lens implant makes it possible to bring flexibility or elasticity in a patient's eye which has been affected by ophthalmic disorders such as presbyopia. Thus, the implanted eye is provided with a new accommodative amplitude which increases the natural accommodative amplitude of the aged non-implanted eye. The new intra cortical lens implant may provide the patient with an accommodative amplitude (or increased accommodative amplitude) that gives comfortable near and far sight in the day to day patient life (e.g. the patient is capable of far distance viewing and reading at a distance of about 30 cm). Given the patient age, he/she will be given back an amplitude of accommodation that can be found in a natural younger crystalline lens (several years backward). This will make it possible to compensate for the loss of visual accommodation that affects the aged non-implanted eye.

This intra cortical lens implant acts as a soft or elastic core in a surrounding more rigid/stiff natural crystalline lens and helps reduce the rigidity/stiffness of the natural lens after implantation. Thus it is possible to come back to initial overall relative mechanical properties (nucleus softer than cortex) that can be found on a younger crystalline lens. The rigidity/stiffness features the relationship between a mechanical stress that is applied to an object and the displacement or deformation of the latter induced by this stress.

The intra cortical lens implant may be made of one material or a combination or mixture of several materials in a solid state that confer mechanical flexibility or elasticity properties to the intra cortical lens implant. The one or more materials have elastic or viscoelastic properties (e.g. a gel has visco-elastic properties and may be in a solid state) that are featured by a shear modulus greater than 10 Pa and less than 10 kPa.

The one or more materials in a solid state have cohesive properties. This means that an intra cortical lens implant made of such material or materials is has its own shape when not implanted, i.e. its shape is maintained without specific external constraints.

The implant made of one or more materials with elastic or visco-elastic properties as defined above can therefore be elastically deformed. This means that the implant is able to deform in an elastic manner when subjected to constraints and therefore to change its initial shape. When the constraints do no longer exert on the implant, the latter may take over its initial shape. This deformation under constraint may be repeated a great number of times in the course of life of the implant.

The one or more solid materials have a refractive index that is suitable for being used in a crystalline lens. More particularly, the refractive index of the material(s) is such that when the intra cortical lens implant is put in place in the crystalline lens, the refractive index of the latter in its most flattened shape is adapted to the far vision.

The new intra cortical lens implant as defined above may deal with other optical disorders linked with lens aging (either as a preventive or curative treatment to such disorders) when at least part of a natural crystalline lens is replaced by an artificial accommodative lens that is not subject to such disorders.

To be noted that the intra cortical lens implant may be put in place in one eye or two eyes of a patient when dealing with a presbyopia disorder or other optical disorders.

In the above new intra cortical lens implant embodiment the anterior pole A and posterior pole E both located on the longitudinal axis of the implant (polar axis) are fixed points of the implant whatever the sagittal plane of the implant (plane including the longitudinal axis). In contrast, the points B and B' that are the most radially extended points of the implant relative to the longitudinal axis may take different positions relative to this axis and to the poles A and E in different sagittal planes. In other words, the axis passing by the points B and B' may be at different angles to the polar axis AE. The four points A, B, E and B' define in every sagittal plane a quadrilateral that may vary in shape from one plane to the other or remain the same for an axi-symmetrical implant. The outer shape of the implant may therefore extend based on such a quadrilateral.

In substance the implant comprises:
a substantially convex anterior surface having an anterior pole A located on the optical axis,
a posterior surface,
the anterior and posterior surfaces connecting in the sagittal plane at the two respective spaced apart points B and B', the anterior part having an outer outline forming a curve that has a radius of curvature that is greater at the anterior pole than at either of the two respective spaced apart points.

According to possible features of the implant:
the anterior part has a convex shape when viewed in a sagittal plane;
the outer outline of each portion of the anterior part is a continuous curve with a radius of curvature R that overall decreases from the anterior pole A to point B, B' in a sagittal plane;
each portion of the posterior part has an outer outline that forms a continuous curve between the point B, B' and the posterior pole E when viewed in a sagittal plane;
the outer outline of each portion of the posterior part includes two points C, D, respectively C', D', located on the curve between the point B, respectively B', and the posterior pole E and that form two inflexion points for the curve;
the two points C, D, respectively C', D', are located on a straight line between the point B, respectively B', and the posterior pole E;
each curve between the point B, respectively B', and the posterior pole E includes two side portions B, C, respectively B', C', and D, E, respectively D', E, flanking a central portion C, D, respectively C', D', the two side portions having a curvature of the same type, convex or concave, and the central portion having a curvature of the opposite type, concave or convex;
the intra cortical lens implant has an axi-symmetrical shape relative to its polar axis when viewed in a sagittal plane;
the intra cortical lens implant has not an axi-symmetrical shape relative to its polar axis when viewed in a sagittal plane;
the intra cortical lens implant has an axi-symmetrical shape relative to its polar axis when viewed in a front plane that is perpendicular to the sagittal plane;
the intra cortical lens implant has not an axi-symmetrical shape relative to its polar axis when viewed in a front plane that is perpendicular to the sagittal plane;
the intra cortical lens implant has an overall volume that is between 10% and 90% of a crystalline lens inner volume in which it is intended to be implanted;
the intra cortical lens implant has a refractive index that is higher than that of the remaining part of the natural crystalline lens within which the implant is intended to be inserted (the refractive index is generally increasing from the periphery towards the core of the implant except for very specific optical disorders); a gradient of refractive index may therefore be established between the implant and the natural lens.

The refractive index of the intra cortical lens implant may be per se a gradient of refractive index or take a single constant value. The gradient may be continuous or not. Continuity or discontinuity in the refractive index may take place at the interface between the intra cortical lens implant and the remaining part of the natural crystalline lens or inside the intra cortical lens implant.

To be noted that the refractive index is generally increasing from the periphery towards the core of the implant except for very specific optical disorders. Overall, the refractive index may lie in the range from 1 to 3. Also a refractive index gradient or refractive index may be selected in a non axi-symmetrical way.

To be noted that the refractive indices and their gradient(s) may be selected when simulation is carried out for a patient's eye as explained subsequently in relation with the second and third aspects of the invention.

A second embodiment of the first aspect concerns an intra capsular lens implant intended to wholly fill in the capsular bag in an eye.

This intra capsular lens implant comprises a core part and a shell part that surrounds the latter, the intra capsular lens implant having a longitudinal axis corresponding to a polar axis of the intra capsular lens implant, wherein the core part comprises an anterior part and a posterior part that extend axially along the polar axis, the anterior part having an anterior pole (A) located on the polar axis and the posterior part having a posterior pole (E) located on the polar axis, the anterior part and the posterior part extending each radially relative to the polar axis on either side thereof, the anterior part and the posterior part having each two portions located on both sides of the polar axis respectively when viewed in a plane including the polar axis, called sagittal plane, each portion of the anterior part having a radial extension that increases from the anterior pole (A) to a point (B, B') where the anterior part ends and the posterior part begins, each portion of the posterior part having a radial extension that decreases from the point (B, B') where the posterior part begins to the posterior pole (E), the outer outline of each portion of the anterior part forming a curve having a radius of curvature that is greater at the anterior pole (A) than at the point (B, B'), both the core part and the shell part being made of one or more materials that have elastic or visco-elastic and cohesive properties in a solid state such that the shear modulus is greater than 10 Pa and less than 10 kPa, or the shell part being made of one or more of the previous materials and the core part being made of a fluid, both the one or more materials and the fluid having a refractive index that is suitable for being used in a crystalline lens.

The intra capsular lens implant comprises a core part and a shell part that surrounds the latter. The core part may act as the above intra cortical lens implant embodiment and more particularly comprises the geometrical features of this intra cortical lens implant. The core part is surrounded by the shell part whereas the above cortical lens implant is intended to be surrounded by natural tissues of the crystalline lens when put in place in the latter. Both the core part and the shell part may be made of one or more materials that have elastic or visco-elastic and cohesive properties in a solid state such that the shear modulus is greater than 10 Pa and less than 10 kPa. Alternatively, the shell part may be made of one or more of the previously described materials while the core part may be made of a fluid (e.g. a liquid or a gas). All that has been described above for the material(s) in relation with the intra cortical lens implant embodiment also applies here.

When both the core part and the shell part are made of one or more of the above materials, the shell part may be made of one or more materials of which the shear modulus is greater than that of the core part.

Both the one or more materials and the fluid have a refractive index that is suitable for being used in a crystalline lens. More particularly, the refractive index is such that when the intra capsular lens implant is put in place in the crystalline lens, the refractive index of the latter in its most flattened shape is adapted to the far vision.

To be noted that the shell part and core part may be viewed as two distinct parts and not as an homogenous single part.

The whole intra capsular lens implant is to be inserted within a natural crystalline lens. The inner of the lens has been cleared beforehand so as to leave unaffected the capsular bag only and the intra capsular lens implant then may perfectly fill in the void created inside the capsular bag.

Alternatively, the intra capsular lens implant may comprise a hollow shell that is intended to be inserted within a natural crystalline lens (the inner of the lens has been cleared beforehand so as to leave unaffected the capsular bag only) and subsequently filled in by one or more visco-elastic materials or a fluid as defined above so as to act as the core part. In this alternative, the capsular bag together with the surrounding external shell part of the hollow shell play the role of a more rigid part of the lens while the core part is more flexible or elastic.

The new intra capsular lens implant may deal with other optical disorders (either as a preventive or curative treatment to such disorders) when the whole natural crystalline lens is replaced by an artificial accommodative lens that is not subject to such disorders.

The core part may be considered as having the features of the above intra cortical lens implant embodiment. In particular, it may also have a shape that is defined by the quadrilateral ABB'E defined above.

According to other possible features of the intra capsular lens implant:
  the shell part of the intra capsular lens implant that surrounds the core part is more rigid than the latter;
  the surrounding shell part is made of one or more materials of which the shear modulus is greater than that of the core part.

The intra capsular lens implant according to the first aspect of the invention aims at physically restoring the flexibility of the crystalline lens and bringing the amplitude of accommodation as close as possible to that of a younger crystalline lens.

The shell part may have a shear modulus less than or equal to the shear modulus of the cortex of the crystalline lens to be physically restored.

To be noted that the core part has a shear modulus less than the shear modulus of the shell part.

Typically, the shell part may have a shear modulus of 5 or 10 kPa approximately and the core part may have a shear modulus of 200 Pa, 500 Pa, 800 Pa, 1000 Pa, or 2 kPa approximately. When the shell part is made of one or more of the above materials, the core part may be made of a fluid which therefore acts a softer core part in a more rigid surrounding shell part.

According to another possible feature, the refractive indices of both the shell part and the core part are defined so as to establish a gradient of refractive index. Refractive indices may be values or distribution of values within each part. The gradient may be continuous or not in each part or from one part to the other, i.e. at the interface between each part. Each of the shell part and core part may have gradient of refractive index in itself or one of them only. In the latter case, the other part has a constant value for the refractive index. Alternatively, both the shell part and the core part have each a constant value for the refractive index and both values are different from each other. To be noted that the refractive index is generally increasing from the periphery towards the core of the implant except for very specific optical disorders. A peripheral zone of the lens may remain untreated (natural). In this case, the above gradient may also take place between the peripheral natural lens part and the shell and core parts. All that has been mentioned above regarding the shell and core parts may be extended to the peripheral natural lens part. Overall, the refractive indices may lie in the range from 1 to 3. Also a refractive index gradient or refractive index may be selected in a non axi-symmetrical way. To be noted that the refractive indices and their gradient(s) may be selected when simulation is carried out for a patient's eye as will be explained subsequently in relation with the second and third aspects of the invention.

All that has been described above for the intra cortical lens implant embodiment may also apply to the above intra capsular lens, in particular to its core part.

The intra capsular lens implant may also comprise any one of the features defined above in relation with the intra cortical lens implant embodiment and that define possible features of the core part.

A second aspect of the invention pertains to the field of systems for simulating the functioning of a human eye. This second aspect concerns in particular a computer system (computer-based system) and method (computer-based method) for simulating a process of visual accommodation.

The mechanism of visual accommodation and presbyopia disorder have been extensively described above in relation with the first aspect of the invention and will not be repeated here.

As presbyopia relates to some deterioration in the visual accommodation process, computer systems have been designed to allow the provision of simulations of the functioning of an eye, more precisely simulations of the process of visual accommodation. However, the computer systems for simulating visual accommodation and currently available are either limited, because they rely on too few physiological entities and physics, or inefficient, because of the large amount of computational resources they need to operate or the computational time required for providing results. These downsides drastically decrease the interest for making use of such systems in a therapeutic environment or for purposes of research and development of therapeutic solutions.

The second aspect of the invention intends to remedy at least one of these disadvantages.

One goal of this second aspect is to provide a computer system (computer-based system) for simulating visual accommodation, i.e. a computer system that is able to simulate a process or operation of an eye switching between far vision and near vision (mechanical and optical simulation) and able to provide graphical and/or numerical outputs in this regard, that mimics more accurately the physiological reality of the visual accommodation process as it naturally occurs.

The computer system according to this second aspect may also address the need for medical actors to use the system in relation to in-vivo cases and real therapeutic constraints. Thus, the computer system for simulating visual accommodation may facilitate the submission and processing of modifications in relation to the geometry and/or to the material properties of the physiological entities that form an eye.

Moreover, while it is possible to use the computer system standalone, for instance for research and developments purposes, it is also possible to make use of the computer system in a computerized therapeutic environment, for instance in relation to a medical imaging device or to a medical instrument or tool (ex: surgical tool) used for the treatment of visual disorders. Thus, the computer system for simulating visual accommodation according to the second aspect of the invention must include functionalities to enable an interface through which it may be connected via a communication link to a remote computer, with which data may be exchanged. Moreover, for the sake of efficiency in such situations where the computer system is part of a distributed environment, it must implement mechanisms for automatic data retrieval to ensure that simulation outputs that are provided are automatically and continuously updated in accordance with retrieved and/or submitted data.

At least one of these goals is achieved by a computer system for simulating visual accommodation, wherein said system comprises one or more processors and one or more computer-readable storage media encoded with instructions that, when executed by at least one of the processors, cause the computer system at least to:

retrieve a pre-defined geometrical model, said pre-defined geometrical model delineating volumetric boundaries of a set of physiological entities of an eye, said set including at least a crystalline lens, a zonula, a ciliary muscle, a sclera and a cornea;

determine if at least one geometry-related change is set and, if so, alter said pre-defined geometrical model using said geometry-related change to set an updated geometrical model;

retrieve a physics-related environment, said physics related environment including at least one physics-related parameter assigned per physiological entity of said set of physiological entities, said physics-related parameter characterizing a mechanical property or an optical property;

determine if at least one physics-related change is set and, if so, alter said physics-related environment using said physics-related change to set an updated physics-related environment; and combine said pre-defined geometrical model, or said updated geometrical model, and said physics-related environment, or said updated physics-related environment, to establish a simulation model.

The computer system for simulating visual accommodation more accurately mimics the physiological reality because simulation outputs provided by the system rely on a three-dimensional geometry of an eye that includes and distinctively addresses all important physiological entities of the eye, which are at least the crystalline lens, the zonula, the ciliary muscle, the sclera and the cornea. More accurate outputs provided by the system result also from the specific way of modeling physiological entities of an eye, from the ability to specify numerous parameters with respect to each physiological entity of an eye, which parameters may define mechanical or optical properties in relation to those entities, and from the variety of results (forces, displacements, optical parameters for specific areas or volumes) that are provided. Greater accuracy and greater efficiency are also achieved because of the system configuration to establish a simulation environment which combines geometrical inputs and parameters characterizing material's properties in a specific manner, with the ability to submit and immediately consider changes and modifications applied to the simulation environment. The computer system further provides improvements in terms of user interaction because it is configured to automatically determine whether data must be retrieved from remote data sources. The simulation model that is established by the computer system integrates all the above-mentioned parameters so as to make them interdependent from each other. The simulation model is both physical and dynamic. The simulation model is conceived so as to take into account (and parameterize) non axi-symmetrical configurations for at least some physical entities in the eye (in particular from a geometrical point of view). This may also be the same for the management of optical and mechanical properties. For example, non axi-symmetrical stresses may be modeled and introduced in the simulation model. The simulation model may also take into account materials and their properties as parameters, which provides a more powerful modeling tool. To be noted that fluidic aspects may also be modeled through this simulation model and therefore be taken into account as parameters together with optical and mechanical parameters. Also the simulation model is not based only on shell and volumes elements for modeling physiological entities but also integrate truss and membranes. Further, gradients of refractive index within the crystalline lens may be parameterized through this simulation model.

All these aspects allow the computer system to be more efficient when used in a therapeutic environment, especially for surgical planning procedures or diagnosis of residual accommodation capability.

To be noted that the simulation model established by the above computer system may be used for any other purpose than correcting presbyopia in a human eye, in particular for correcting any optical disorders in a human eye.

By way of example, the simulation model may be used in the following applications:
refractive calculation;
optimization of an Intra Ocular Lens (IOL) after refractive disorders have already been treated by corneal modification (LASIK);
design of progressive optical surfaces;
diagnosis (the model may be used in connection with existing imaging methods in order to get an improved knowledge of a patient's eye);
glaucoma (the model may be used to simulate flows of fluids inside a patient's eye);
keratoconus detection (the model may be used together with corneal topography technologies to identify and determine the evolution of qualitative and quantitative parameters of the corneal topography);
Corneal treatment such as preventive ones (e.g. contact lenses) or corrective ones (e.g. crosslinking, keratoplasty) (the model may be used to determine and evaluate a possible treatment/process in order to put an end to keratoconus development or to correct any other corneal topographic disorder);
IOL and AIOL (Accommodative IOL) design, in particular an implant for cataract disorder may be designed through using the model, e.g. an implant with specific accommodative features (AIOL).

The computer system as described above is configured to receive data and output other data (either on a display assembly or interface or outside the system, e.g. the outputted transformed data may be transmitted to a distinct outside device or system). This computer system may comprise computer programs that are stored on computer readable storage media and may be executed or run upon command or automatically. Execution of the programs causes execution or performance of steps of corresponding computer-based method(s).

Correspondingly, this second aspect also concerns a computer-based method for simulating visual accommodation, the method comprising the steps of:
retrieving a pre-defined geometrical model, said pre-defined geometrical model delineating volumetric boundaries of a set of physiological entities of an eye, said set including at least a crystalline lens, a zonula, a ciliary muscle, a sclera and a cornea;
determining if at least one geometry-related change is set and, if so, alter said pre-defined geometrical model using said geometry-related change to set an updated geometrical model;
retrieving a physics-related environment, said physics related environment including at least one physics-related parameter assigned per physiological entity of said set of physiological entities, said physics-related parameter characterizing a mechanical property or an optical property;
determining if at least one physics-related change is set and, if so, alter said physics-related environment using said physics-related change to set an updated physics-related environment; and
combining said pre-defined geometrical model, or said updated geometrical model, and said physics-related environment, or said updated physics-related environment, to establish a simulation model.

Further possible features of the computer system and/or computer-based method are defined below:
said instructions, when executed by at least one of the processors, further cause the computer system to display a graphical user interface in which at least a three-dimensional representation of an eye is presented, said graphical interface being configured to contain at least one input area for submitting said geometry-related change and/or said physics-related change;
said instructions, when executed by at least one of the processors, further cause the computer system to detect when said geometry-related change results from an action performed in relation to said three-dimensional representation;
said instructions, when executed by at least one of the processors, further cause the computer system to retrieve said geometry-related change and/or said physics-related change from a remote source;
said instructions, when executed by at least one of the processors, further cause the computer system to compute, using said simulation model, at least one simulation result of visual accommodation, said simulation result containing data that, in relation to one physiological entity of said set of physiological entities, relates to a force, a mechanical stress, a deformation or a displacement, and/or, in relation to an optical domain, relates to an optical change, and/or relates to an accommodation amplitude value of said eye;
said simulation result is computed on the basis of a first value of tension applied on a posterior part of said zonula and a second value of contraction of said ciliary muscle;

said physics-related parameter or said physics-related change relates to a contraction level of said ciliary muscle and/or an elongation level of a posterior part of said zonula;

said physics-related parameter or said physics-related change relates to a contraction and/or elongation level of a part of said ciliary muscle;

said geometry-related change relates to said crystalline lens' shape and/or said sclera's shape;

said geometry-related change relates to said cornea shape and/or said zonula's length;

said geometry-related change relates to at least one position where said ciliary muscle, or said crystalline lens, is connected to said zonula;

said crystalline lens includes at least a nucleus, a lens cortex, a lens capsule and a lens epithelium;

said set of physiological entities includes a vitreous body and an aqueous humor;

said physics-related parameter or said physics-related change relates to said aqueous humor's viscosity, said aqueous humor elasticity and/or a viscoelastic property of said vitreous body;

said physics-related parameter or said physics-related change applies to only a part of said physiological entity to which it is assigned.

A third aspect of the invention concerns a method for correcting optical disorders of a human eye, comprising the following steps:

obtaining biometric data representing dimensional, mechanical and optical properties of a patient's eye, in particular of physiological entities thereof including a crystalline lens;

updating the dimensional, mechanical and optical parameters of a 3D model representative of a human eye based on the obtained biometric data so that the model be representative of the patient's eye, in particular its physiological entities;

applying the following sub-steps:

i) entering possible mechanical and optical corrections into at least one of the physiological entities of the updated model;

ii) simulating the mechanical and optical behavior of the updated model with these mechanical and optical corrections;

until the entered possible mechanical and optical corrections allow the desired mechanical and optical behavior to be reached through simulation so as to correct optical disorders and improve comfort of vision in terms of far and near vision (e.g. relative to predetermined far and near vision);

validating these mechanical and optical corrections;

setting up operating parameters for a surgical piece of equipment so that the latter be operative to apply the validated mechanical and optical corrections to said at least one of the physiological entities of the patient's eye.

Steps i) and ii) may be carried out as many times as necessary until obtaining the desired mechanical and optical behavior.

The 3D model is used through the above method so as to define for example the location, shape and size of an inner lens zone that is to be treated/processed (by insertion of a lens implant or electromagnetic treatment) in order to correct optical disorders and improve comfort of vision in terms of far and near vision. By way of example, use of this model makes it possible to define the location, shape and size of the phakorestoration pattern that will correct optical disorders and improve comfort of vision in terms of far and near vision. Correction of optical disorders may include optimizing the accommodation power (increase of accommodative amplitude) of the patient's eye.

The surgeon may validate, possibly in consultation with the patient, these mechanical and optical corrections or decide to carry out one or several of the above-mentioned obtaining, updating and i) and ii) steps.

Following the validation operating parameters of a surgical piece of equipment or tool or apparatus are set up in accordance with the validated corrections. In the case of electromagnetic treatment with an electromagnetic apparatus, such operating parameters may include energetic parameters (ex for a femtosecond laser: energy, pulse duration, spatial density, pulse frequency, repetition) and geometric parameters (axial position, envelope shape). The apparatus is thus programmed accordingly.

Next the surgeon activates the treatment or surgical step on the patient's eye with the surgical piece of equipment or tool or apparatus that has been set up accordingly.

In a general manner, the third aspect method provides the following advantages:

it provides a tailored treatment/process for the patient which makes it possible, thanks to simulation, to optimize the optical result while minimizing the volume of the patient's eye to be treated (e.g. only a portion of the crystalline lens may be treated instead of the whole lens) and the intensity of the treatment;

the results of the treatment may be simulated before carrying out the treatment;

the simulation process may control a surgical piece of equipment or tool or apparatus so as to perform exactly what has been obtained through simulation;

there is no need to have an additional simulator since the steps i) and ii) are sufficient to provide the desired results in terms of mechanical and optical behavior;

this method makes it possible to increase the reliability in the choice of a solution for correcting optical disorders;

this method makes it possible to increase the reliability in the achievement of a solution for correcting optical disorders;

this method makes it possible for the practitioner to gain time when correcting optical disorders.

According to other possible features:

the physiological entities of the patient's eye include the crystalline lens, a zonula, a ciliary muscle, a sclera and a cornea;

the crystalline lens includes at least a nucleus, a lens cortex, a lens capsule and a lens epithelium;

the physiological entities includes a vitreous body and an aqueous humor;

the 3D model representative of a human eye is established by the above-mentioned computer system;

the above correction method more particularly applies to the correction of presbyopia, the possible mechanical and optical corrections to be entered relating to the crystalline lens, the steps i) and ii) being applied until the entered possible mechanical and optical corrections enable the desired mechanical and optical behavior in terms of restoration of flexibility and increased amplitude of visual accommodation to be reached through simulation and the operating parameters for a surgical piece of equipment or tool are set up so that the latter be operative to apply the validated mechanical and optical corrections to the crystalline lens of the patient's eye.

This third aspect method may further include a treatment or surgical step or phase that uses the surgical piece of equipment or tool or apparatus of which the operating parameters have been set up.

To be noted that a possible control step (or diagnosis step) is performed after the treatment or surgical step has been carried out, including in particular control of refraction. Depending on the result of this control step, possible enhancement of the process may be envisaged, e.g. leading to enhanced simulation or computational modeling and simulation.

A fourth aspect of the invention concerns a method for correcting presbyopia of a human eye, comprising a step of applying electromagnetic radiation to an inner zone Z of the crystalline lens of the human eye through an electromagnetic apparatus so as to render the inner lens zone more flexible than the unmodified surrounding remainder of the natural crystalline lens and with a higher refractive index than the latter, the inner lens zone Z including at least a portion of the crystalline lens nucleus, when viewed in a sagittal plane including the optical axis (or polar axis) of the lens the inner lens zone including:
- a substantially convex anterior surface having an anterior pole located on the optical axis,
- a posterior surface,
- the anterior and posterior surfaces connecting in the sagittal plane at two respective spaced apart points, the anterior part having an outer outline forming a curve that has a radius of curvature that is greater at the anterior pole than at either of the two respective spaced apart points.

In a general manner, the fourth aspect method provides the following advantages:
- it is a non-invasive method since no implant has to be put in place in the lens;
- this method makes it possible to deal with the origin of the optical disorder not the consequences thereof;
- through this method the patient's crystalline lens is restored with accommodative capacities that are comparable to those inherent to a natural lens in its origin; therefore there is no need for the eye to adapt as this would be the case with an implant and no visual compromise has to be made; here the eye will function normally;
- this method may be implemented at successive time instants over the years, for instance to apply successive treatments, e.g. by modifying the inner lens volume to be treated and/or by modifying the energy applied to the inner lens volume etc.;
- this method may take place in an existing patient planning for example before envisaging cataract surgery.

The inner lens zone Z of the lens may have the shape that is defined for the intra cortical lens implant of the above first aspect in its overall shape and with at least one of the above-mentioned possible more detailed features.

To be noted that this method may include beforehand the third aspect method that sets up appropriate operating parameters for the electromagnetic apparatus to be used in the treatment or surgical step. These parameters are adapted to the patient's eye features and have been determined through the third aspect method for correcting the specific presbyopia disorders the patient suffers.

A possible control step (or diagnosis step) is performed after the treatment or surgical step has been carried out, including in particular control of refraction. Depending on the result of this control step, possible enhancement of the process may be envisaged, e.g. leading to enhanced simulation or computational modeling and simulation.

According to other possible features:
- the electromagnetic apparatus may be chosen among a femtosecond laser, an ultrasound generator, in particular an HF focused ultrasound generator;
- the method includes scanning the inner zone Z of the crystalline lens with a spot (ex: laser) or beam (ex: ultrasound) according to a predetermined scanning pattern;
- the scanning starts with the posterior part of the inner zone towards the anterior part thereof;
- the scanning may be performed by successive layers;
- the scanning may be performed so that the spot (ex: laser) or beam (ex: ultrasound) follows a spiral path.

A fifth aspect of the invention concerns a method for correcting presbyopia of a human eye through introducing a lens implant inside a natural crystalline lens of a patient affected with presbyopia disorders. The lens implant may be the lens implant according to the above first aspect, i.e. an intra cortical lens implant or an intra capsular lens implant.

Overall if an intra cortical lens implant is to be implanted within the crystalline lens of a patient, then the following main steps may be carried out:
- cortical channeling;
- treatment of the inner zone of the lens where the implant has to be placed so as to remove this inner zone (this step may be achieved through using an electromagnetic apparatus such as one described in the fourth aspect);
- scleral incision;
- extraction;
- insertion of the intra cortical lens implant in the freed inner zone.

If an intra capsular lens implant is to be implanted within the crystalline lens of a patient, then the following main steps may be carried out:
- cortical incision;
- capsulorhexis;
- phakoemulsification; and
- insertion of the intra capsular lens implant within the void crystalline lens capsule or insertion of a shell part intra capsular lens implant followed by the insertion of a core part intra capsular lens implant.

To be noted that the fifth aspect method may include beforehand the third aspect method that sets up appropriate operating parameters for the surgical piece of equipment or tool or apparatus to be used in the treatment or surgical step. These parameters are adapted to the patient's eye features and have been determined through the third aspect method for correcting the specific presbyopia disorders the patient suffers.

A possible control step (or diagnosis step) is performed after the treatment or surgical step has been carried out, including in particular control of refraction. Depending on the result of this control step, possible enhancement of the process may be envisaged, e.g. leading to enhanced simulation or computational modeling and simulation.

To be noted that some of the above aspects may be further completed by additional features and aspects that will be described subsequently.

BRIEF DESCRIPTION OF THE DRAWINGS

Other features and advantages will emerge in the course of the remainder of the description, given by way of non-limiting example only, with reference to the following drawings, in which:

FIGS. 7A and 7B schematically illustrate in a crystalline lens CL the extreme volumes that can be occupied by an intra cortical lens implant according to the invention;

FIGS. 7C and 7D schematically illustrate in a crystalline lens CL' possible shapes/volumes of an intra cortical lens implant according to the invention;

FIG. 9 is a flowchart illustrating several possible methods for placing an intra cortical lens implant or an intra capsular lens implant in a patient's eye and for non-invasively treating a patient's crystalline lens;

FIGS. 12G-J illustrate examples regarding application of a possible electromagnetic pattern (laser or ultrasound) on an inner zone IZ of a crystalline lens CL;

DETAILED DESCRIPTION

Figure 1:
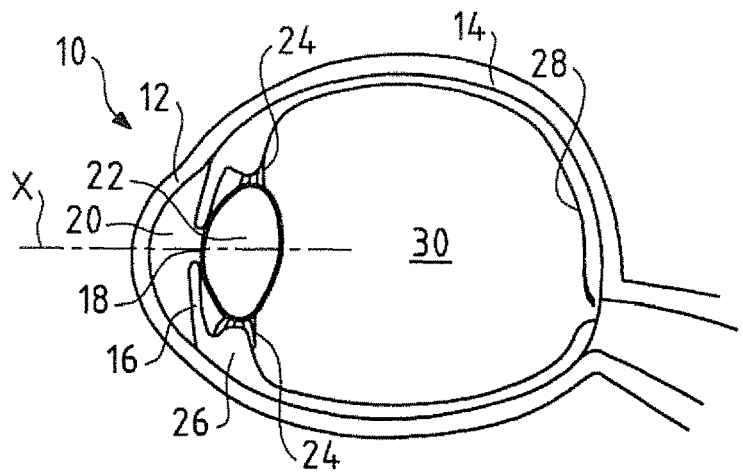
FIG. 1 is a diagrammatic illustration of a human eye in a sagittal cross-section.

FIG. 1 shows a human eye cross-section (viewed in a sagittal plane) or side view.

The eye 10 includes the cornea 12 and the sclera 14. The iris 16 and pupil 18 are located behind the cornea 12. The iris includes muscles called sphincter muscles that are able to contract and expand in order to control the diameter of the pupil 18.

The eye includes an anterior chamber 20 that is located between the cornea and the iris and pupil.

A crystalline lens 22 is located posterior to the cornea 12 and the iris 16. Crystalline lens 22 is sustained by zonules 24 which form a complex web connecting the latter to the ciliary muscle 26. Thanks to this sustaining configuration the lens is able to change shape for focusing.

The eye also includes the retina 28 located at the back of the eye, the purpose of which is to form an image of an object looked at by the eye.

A posterior chamber 30 located between crystalline lens 22 and retina 28 forms the major part of the eye and is filled in by the vitreous body not represented here for the sake of clarity.

The optical axis of the eye is commonly known as being an average between the optical axis of the cornea and the optical axis of the crystalline lens. In FIG. 1 an optical axis X is illustrated and will be used in the remainder of the description as being the optical axis of the crystalline lens.

Figure 2:
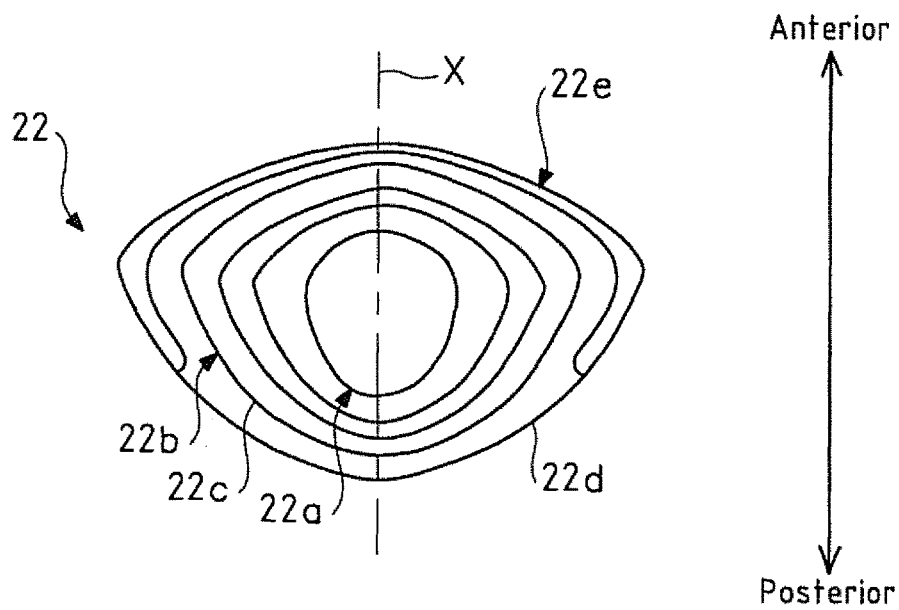
FIG. 2 is a diagrammatic illustration of a human eye crystalline lens in a sagittal cross-section.

FIG. 2 illustrates a diagrammatic overall enlarged view of crystalline lens 22 in a sagittal plane. Such a plane includes the optical axis X of the lens.

Crystalline lens 22 is a multilayered structure of collagen and crystalline that can change its optical power depending on its state of deformation. The lens has an onion-like structure and comprises four sub-parts or components:

- the nucleus 22a is a central part made of multiple layers, also known as age related nuclei; in particular, nucleus 22a successively includes for an adult, from the center towards the periphery, the embryonic nucleus (En), the fetal nucleus (Fn), the juvenile or infantile nucleus (Jn) and the adult nucleus (An) which are not identified on FIG. 2 for the sake of clarity (some of these different layers are illustrated in FIGS. 7A-D);
- the cortex 22b surrounds nucleus 22a and the frontier between both sub-parts is denoted 22c;
- the capsule 22d is a thin, relatively stiff bag that contains both nucleus 22a and cortex 22b;
- the epithelium 22e is an anterior layer located in between the anterior portion of cortex 22b and capsule 22d (also called capsular bag) and made of active cells.

The external shape of the lens looks like an ellipsoid in a sagittal plane, with a greater curvature on the posterior pole than on the anterior one.

The inventors have discovered that appropriate flexibility can be restored to a crystalline lens which hardens with age (presbyopia is the first optical disorder that appears in connection with the aging of a lens). Accommodative amplitude of an aged natural lens can therefore be modified, in particular increased, so as to provide the patient with comfort visual accommodation. The patient's eye is therefore restored with visual accommodation of a younger eye. This has been made possible thanks to new lens accommodative devices, in particular specific implants, and methods/systems for implementing/achieving these lens accommodative devices in patient's eyes, in particular the specific implants. The lens accommodative devices, in particular specific implants, in accordance with the present embodiments have not anatomical outlines or inner structures. However, in some other embodiments they may have anatomical outlines or inner structures. The inventors have also discovered that new lens physical restoration methods which do not involve any implant make it possible, when applied to a patient's crystalline lens, to restore flexibility and, therefore, increase accommodative amplitude. These methods may restore optical properties to the crystalline lens and possibly, when needed, bring optical correction(s), e. g. correct astigmatism and increase the depth of field.

Figure 3A:
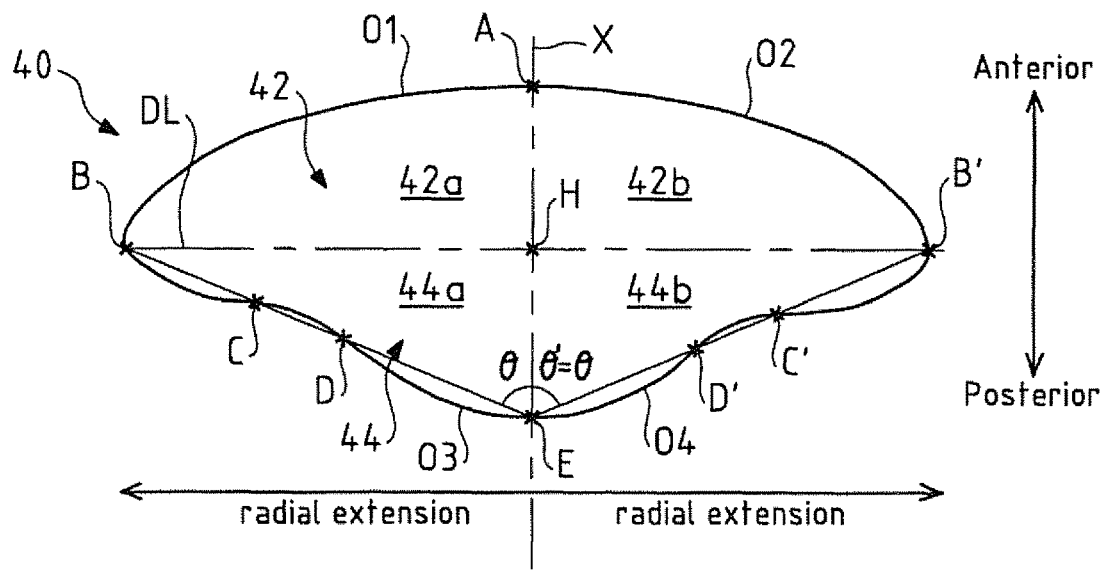
FIG. 3A is a sagittal view of an intra cortical lens implant according to an embodiment of the invention.

FIG. 3A illustrates an intra cortical lens implant according to a first embodiment of the invention.

This view illustrates an intra cortical lens implant 40 in a sagittal plane which has an axi-symmetrical shape relative to its longitudinal axis, also called polar axis as it passes by the poles of the implant as will be seen subsequently. This means that each portion located on either side of the axis has the same shape as in a mirror whatever the cross section plane including this axis. When such an implant 40 is placed within the FIG. 2 lens it is centered about the optical axis X of the lens and the polar axis of the implant 40 therefore coincides with the optical axis X of the FIG. 2 lens. For this reason the polar axis of the implant 40 is considered as identical to the optical axis X of the lens. Thus, the axis X is considered as both the optical axis of the lens and the polar axis of the implant in the remainder of the description unless otherwise specified such as in the description of FIG. 6 where the polar axis of the implant does not coincide with axis X.

The intra cortical lens implant 40 has for instance an overall shape of a mushroom or butterfly wings.

This implant is intended to be located within crystalline lens 22 (FIG. 2) at a location which will be described subsequently. When in place the implant 40 will occupy a portion of the inner volume (this volume comprises nucleus 22a and cortex 22b) of the crystalline lens 22 that is bounded by the capsular bag 22d. This holds true for any other shape of intra cortical lens implant envisaged in accordance with the present invention.

As illustrated in FIG. 3A, the implant 40 extends axially along its polar axis from an anterior location represented by a point called anterior pole A to a posterior location represented by a point called posterior pole E. Poles A and E are fixed whatever the sagittal cross section of the implant.

Implant 40 also extends radially relative to its polar axis, i.e. in a direction that is perpendicular to this axis.

Figure 4A:
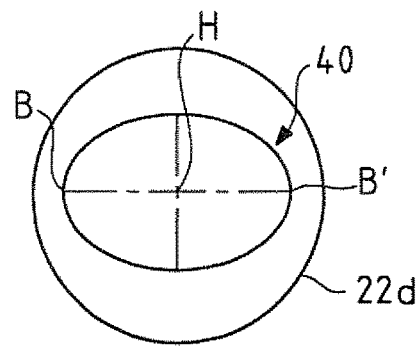
FIGS. 4A and 4B illustrate different possible intra cortical lens implant shapes in a crystalline lens front view.

Although the intra cortical lens implant is represented in a sagittal plane it is a 3D volume and its radial extension is to be considered in every radial direction around its polar axis X perpendicularly thereto, e.g. as illustrated in the front view of FIG. 4A.

As illustrated in FIG. 3A, the radial extension of implant 40 varies along the polar axis when following the outer outline of the implant from anterior pole A to posterior pole E: it first increases when following the outer outline from anterior pole A to both points B and B' simultaneously (maximum radial extension) and then decreases when following the outer outline from points B and B' to posterior pole E simultaneously. The points B and B' in a sagittal section are located on the equatorial plane of the implant which is here represented by the dashed line DL (this line is the intersection between the equatorial plane and the sagittal plane). This definition of the equator also applies to other inner structures/layers of the lens.

The implant 40 comprises a body in a solid form or state, i.e. having a given shape that can be maintained as such in the absence of any external constraints (such as constraints exerted by an outer device). It therefore has cohesive properties.

As will be seen subsequently, the intra cortical lens implant may alternatively take other embodiments forms.

The body is made of one or more materials with elastic or visco-elastic properties which have a shear modulus that is greater than 10 Pa and less than 10 kPa. This guarantees that the intra cortical lens implant will be flexible enough relative to the remainder of the natural crystalline lens that surrounds the implant and that is more rigid than the latter. As already mentioned above the one or more materials of the implant are such that it can be elastically deformed. The one or more materials may be a gel. The value of the shear modulus is adapted to the patient's eye and particularly the crystalline lens, i.e. its mechanical properties (according to clinical results or literature) and geometrical features (obtained through imaging such as the residual amplitude, i.e. the gap between the most and the least accommodated position of the lens, the geometry specific to each position, i.e. for each position the anterior and posterior curvature radii, the equatorial diameter and the thickness or axial extension of the lens along the optical axis X, and the possible axial shift of the lens between the two extreme positions).

Typically, the natural peripheral part of the crystalline lens that surrounds the intra cortical lens implant has a shear modulus greater than 1 or 2 kPa (which corresponds to a 40 years eye on average), which corresponds to a more rigid or stiff part than the implant.

Figure 3B:
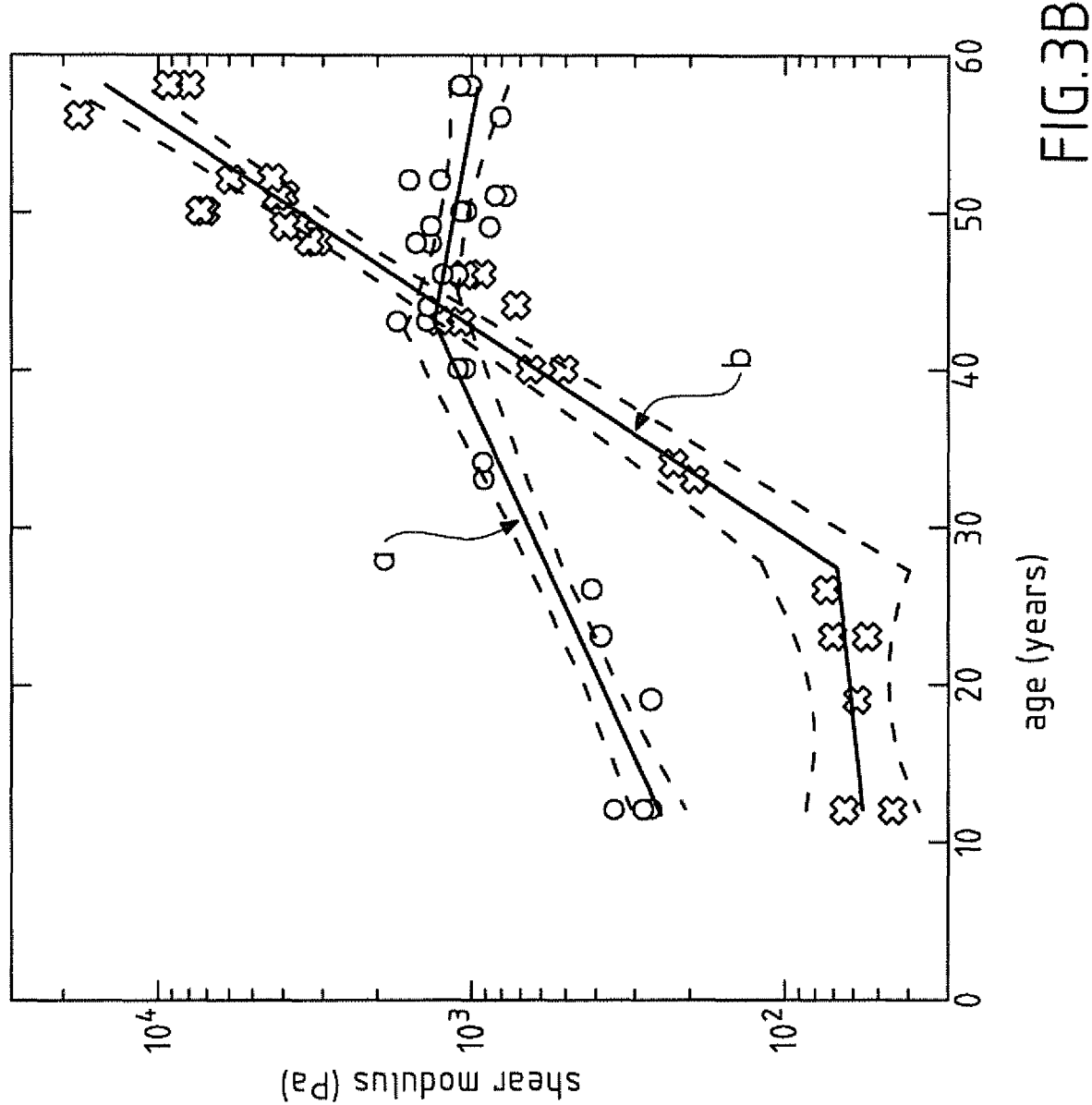
FIG. 3B is a graph representing the variation in the cortical and nucleus shear modulus over time.

FIG. 3B represents the evolution of the shear modulus (it is a logarithmic scale of the shear modulus) of both the cortex (curve a) and the nucleus (curve b) of an eye over time between ages of 10 and 60. These curves are illustrated and described in an article entitled "Shear modulus data for the human lens determined from a spinning lens test" from Wilde G S, Burd H J, Judge S J, Experimental Eye Research, vol. 97 Issue 1, p 36-48, April 2012. These curves show an inversion area between 40 and 50 years around a shear modulus value of 1 kPa: the shear modulus of the nucleus (curve b) keeps on increasing with age with a greater rate than the shear modulus of the cortex (curve a) and with greater values. Past this inversion area the relative properties between the nucleus and the cortex are inverted. The curves illustrate the trend that has been observed on a plurality of patients' eyes over years (this is an example of statistical clinical data). Thus, for a given patient affected with presbyopia the shear modulus of the intra cortical lens implant will be selected at a value much less than that of the natural cortex. This will make it possible to get back to a more favorable zone of the graph, prior to the inversion area, where the nucleus is younger and softer. For example, for a cortex with a shear modulus value of 1 kPa the nucleus will be allocated with a value of 0.5 kPa.

Figure 11A:
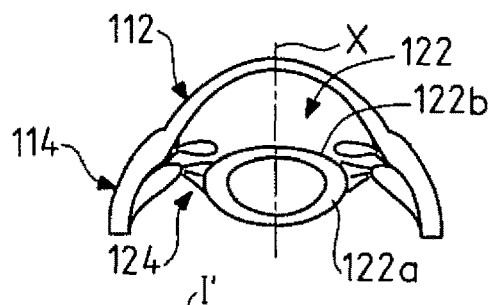
FIGS. 11A-M are views illustrating different steps performed in other methods of FIG. 9 for placing an intra capsular lens implant in a patient's eye.
Figure 11B:
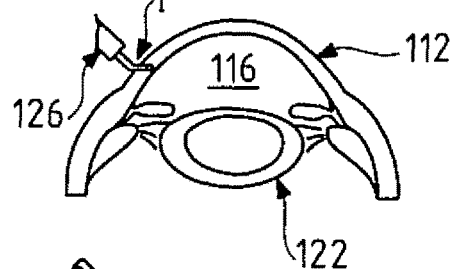
Figure 11C:
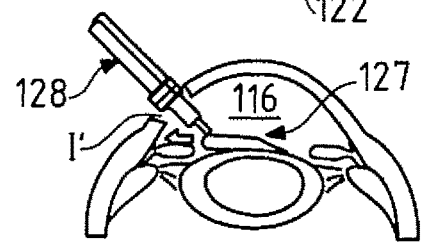
Figure 11D:
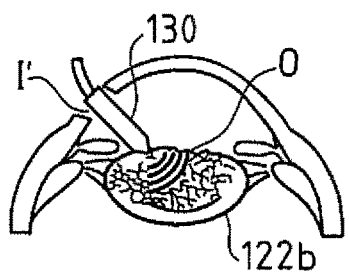
Figure 11E:
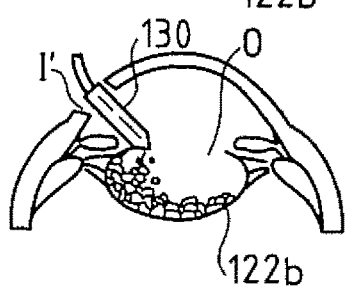
Figure 11F:
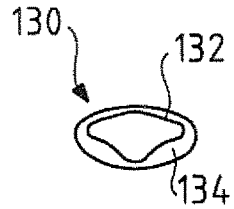
Figure 11G:
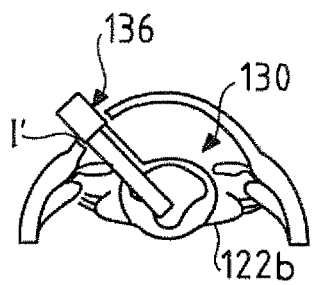
Figure 11H:
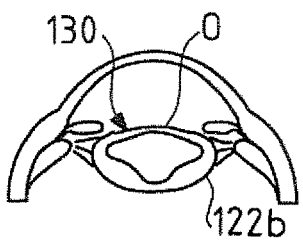

In another embodiment such as that illustrated in FIGS. 11F-H the peripheral or surrounding implant part 134 (shell part 134) may be slightly softer than the initial (natural) cortex and may take a shear modulus value of 0.7 kPa for example, or may have a viscosity in register with this shear modulus. The nucleus may take a shear modulus value of 0.5 kPa for example, or may have a viscosity in register with this shear modulus.

By way of example, the material body is made of silicon or hydrophilic acrylics or hydrophobic acrylic or elastomer and, for example, may be cross-linked polydimethylsiloxanes possibly reinforced with silica or EMA (ethyl methacrylate), or HEMA (Hydroxyethyl methacrylate), or a combination of both previous examples (co-polymers) (material adapted for a medical use). Other materials may alternatively be used for manufacturing the intra cortical lens implant.

The implant 40 comprises an anterior part 42 and a posterior part 44 that are each defined along the polar axis X by extending therealong.

The anterior part 42 begins at anterior pole A and extends rearwardly towards the posterior part. The anterior part 42 is defined by the upper part of the body (FIG. 3A) that is delineated by the outer convex outline that connects point B to point B' through anterior pole A and by the equatorial plane (line DL) that connects directly point B to point B'. Put it another way, the anterior part 42 is located on one side of the equatorial plane (upper side in FIG. 3A) and the posterior part 44 is located on the opposite side (lower side in FIG. 3A). The point denoted H that is situated both on the equatorial plane and axis X corresponds to the orthogonal projection of each of points B and B' on axis X.

As already mentioned above, the anterior part 42 extends radially relative to the polar axis X on either side thereof in the sagittal plane of FIG. 3A.

On this sagittal plane of FIG. 3A, the anterior part 42 has two portions located on both sides of the longitudinal axis respectively: a left side portion 42a and a right side portion 42b that are symmetrical to each other with respect to axis X in this embodiment.

To be noted that in other embodiments the left and right side portions of the anterior part may not be symmetrical.

Each portion 42a, 42b of the anterior part has a radial extension or dimension that increases from the anterior pole A to point B for portion 42a and to point B' for portion 42b, where the anterior part 42 ends and the posterior part 44 begins.

The outer convex outline O1, O2 of each portion 42a, 42b forms a continuous curve in the plane of FIG. 3A with a radius of curvature that is greater at the anterior pole A than at point B and B' depending on the portion.

In the present embodiment the radius of curvature continuously decreases from A to B for left side portion 42a and from A to B' for right side portion 42b. This configuration of the anterior part of the intra cortical lens implant makes it possible to continuously increase the thickness of the anterior part of the crystalline lens that is located between the capsular bag and implant 40 (see for example FIG. 5). This may therefore cause a continuous and controlled increase in the rigidity of this anterior part of the crystalline lens. This configuration makes it possible to precisely control the distribution of the stresses between the ciliary muscle and the zonules and the softer/more flexible intra cortical lens implant through the peripheral more rigid part of the crystalline lens (cortex). The above may apply to other intra cortical lens implants that may have different overall shapes, non axi-symmetrical configurations, different posterior parts etc.

However, in other embodiments, the radius of curvature may locally vary differently between A and B (same between A and B'), e.g. by successively alternating portions of curve with decreasing and increasing radii of curvature such as waves while overall decreasing from A to B (same from A to B'). This alternate configuration provides an overall control increase in the rigidity of the lens anterior part. Such an alternate configuration with local curvatures induces controlled astigmatism and increase in the depth of field. Also, such a shape makes it possible to improve spherical aberrations that disturb visual acuity by creating a gradient of refractive index depending on the refractive index of the material.

As represented in FIG. 3A, the value of the angle θ defined by the two segments [A, E] and [B, E] in the sagittal plane may be comprised between 1° and 90°. This is the same for the angle θ' (here the two angles θ and θ' are the same) between the segments [A, E] and [B', E]. Such an angle makes it possible to have an intra cortical lens implant with sufficient flexibility or softness relative to the more rigid part of the crystalline lens located around the intra cortical lens implant within the capsular bag (ex: cortex). More particularly, such an angle θ makes it possible to control the curvature change of the anterior face of the crystalline lens in accordance with the direction and the distribution of the stresses that are available in a conventional zonular system.

Figure 6:
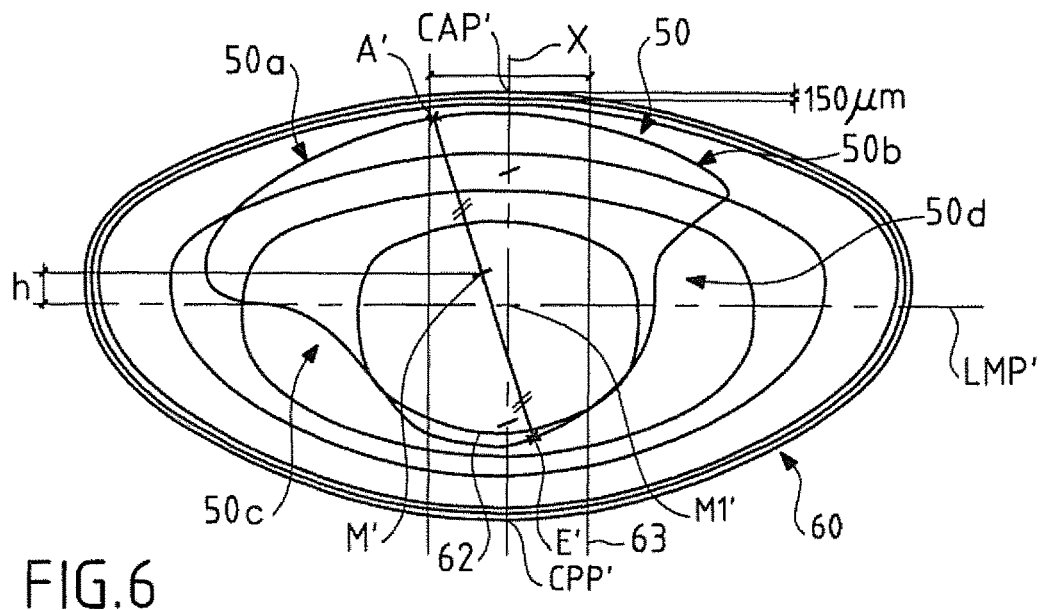
FIG. 6 illustrates a variant embodiment of an intra cortical lens implant with a non-axisymmetric shape in a sagittal view.

However, in other configurations, the angle may differ from one side to the other (θ≠θ') when the intra cortical lens implant has not an axi-symmetrical configuration (ex: FIG. 6).

As already mentioned above, the posterior part 44 extends radially relative to the polar axis X on either side thereof in the sagittal plane of FIG. 3A.

On this sagittal plane of FIG. 3A, the posterior part 44 has two portions located on both sides of the longitudinal axis respectively: a left side portion 44a and a right side portion 44b that are here symmetrical to each other with respect to axis X in this embodiment.

Each portion 44a, 44b of the posterior part has a radial extension that decreases from the point B for portion 44a and from the point B' for portion 44b respectively, where the posterior part begins, towards the posterior pole E.

As represented in FIG. 3A, the outer outline O3, O4 of each portion 44a, 44b respectively is not a straight line between B and E (resp. B' and E).

More particularly, each outer outline O3, O4 forms a continuous curve between the point B, B' respectively and the posterior pole E in FIG. 3A. Each curve is wavy in this embodiment.

Each outer outline O3, O4 includes two points C, D, respectively C', D', located on the curve between the point B, respectively B', and the posterior pole E and that form two inflexion points for the curve.

As represented in FIG. 3A, the two inflexion points C, D, respectively C', D', are located on a straight line between the point B, respectively B', and the posterior pole E.

Each curve between the point B, respectively B', and the posterior pole E includes two side portions (B, C), respectively (B', C'), and (D, E), respectively (D', E), flanking a central portion (C, D), respectively (C', D'). The two side portions for each curve have a curvature of the same type and the central portion has a curvature of the opposite type.

Each curve might therefore be seen here as including a double hump.

Thus, in the present embodiment, the two side portions (B, C) and (D, E) for curve O3 (respectively (B', C') and (D', E) for curve O4) have an outwardly convex shape while the central portion (C, D) (respectively (C', D')) has an inwardly concave shape.

To be noted that the overall shape of each curve O3 and O4 can be inverted in a variant embodiment: the two side portions are concave and flank a central convex portion. Alternatively, only one shape of a curve is inverted relative to the other curve.

This overall shape is adapted to a patient and here makes it possible to create an aspherical intra cortical lens implant:

the region corresponding to DED' has a marked curvature allowing close objects to be seen;

the region corresponding to BC and B'C' has a less marked curvature which allows far objects to be seen.

Overall the shape of the curve connecting B and E as well as B' and E is a polynomial of a degree that is adapted to the patient's eye. This polynomial may be designed so as to favor the volume of nucleus to be treated relative to the untreated volume of cortex in the natural crystalline lens with a view to obtaining a spring effect. This spring effect relies on the more rigid cortex on which the intra cortical lens implant may rest and compress before returning to its initial shape. To be noted that the above may apply to other implant shapes, with different anterior parts, with non axi-symmetrical configurations etc.

To be noted that in any sagittal cross-section the four points A, B, E and B' form a quadrilateral and the outer outline of the posterior part has to be convex overall even though some local concavities may be present. This overall biconvex shape of the anterior part and posterior part outer outlines makes it possible to have a biconvex intra cortical lens implant. When the quadrilateral ABEB' is defined the four points are properly defined relative to each other. The two segments AE and BB' intersect and are perpendicular to each other in the implant 40. However, in a non axi-symmetrical shape the segments AE and BB' are not perpendicular to each other. In such a configuration the two poles A and E are still the same whatever the sagittal plane (passing by the polar axis AE) whereas the segment BB' may vary depending on the sagittal plane.

The above holds true for any other shapes of intra cortical lens implant according to the invention than that of FIG. 3A and for instance for non-axi symmetrical implant shapes.

If the posterior part were concave overall then optical artefacts, diffraction might occur and the gradient of refractive index (GRIN) would vary in an undesired way. In addition, the mechanical performance of such a soft intra cortical lens implant on the crystalline lens could be adversely affected due to a less efficient mechanical cooperation between the concave posterior part of the intra cortical lens implant and the more rigid posterior cortex against which it rests.

It is to be noted that the two side portions of each curve here are symmetrical to each other relative to the polar axis of the implant.
In another embodiment the two side portions may not be symmetrical to each other relative to the polar axis of the implant, and the angles θ and θ' may be different between the two side portions. Such an asymmetrical configuration may be useful, e.g. when one of the patient's eyes is affected by a strong astigmatism. In such a case, an optical correction is applied through an asymmetrical configuration of the intra cortical lens implant in order to create a deformation of the intra cortical lens implant that is different from one side to the other when installed in the natural lens.

The intra cortical lens implant adapts to the patient's eye morphology and may therefore be symmetrical or asymmetrical depending on the morphology, with different anterior and posterior portions than those of FIG. 3A (however, these portions keep the same main characteristics in terms of convexity of the anterior and posterior parts and opening angles θ and θ').

In other embodiments the curvature radius of one or several of the side and central portions of one or both curves O3 and O4 may vary (with respect to the curvatures of FIG. 3A) so that the convexity/concavity is more or less pronounced. In other alternative embodiments the number of convex and/or concave portions may differ between left and right curves relative to the polar axis of the implant.

Whatever the embodiment, the posterior part outer outline may be continuous and convex overall so as to form an optical interface adapted to the patient's eye morphology.

To be noted that the shape of the posterior part outer outline may vary in other embodiments that are not depicted here.

By way of example, the outer outline between B and E (same for B' and E) may be strictly convex or rectilinear and the connection or edge between the outer outline and the anterior part at point B (same for B') is rounded. The shape of the outer outline at point E is also rounded. If any sharp edge were present on the optical path or at any point on the outer outline of the intra cortical lens implant, then unwanted mechanical stresses and optical artefacts and diffraction might be generated during the implant deformation in situ.

Whatever the accurate shape of the intra cortical lens implant, its overall aim is to restore mechanical properties, in particular flexibility, to the natural crystalline lens when implanted so as to increase accommodative amplitude and, therefore, at least reduce presbyopia disorders. Such an intra cortical lens implant may also provide optical correction(s) for correcting astigmatism and/or increasing the depth of field in the patient's eye.

FIG. 4A illustrates a front view, i.e. a view taken in a plane that is perpendicular to the polar axis of the implant (here axis X), of the implant 40 located inside capsular bag 22d. This view is taken in the equatorial cross-section plane perpendicular to a sagittal plane and that includes points B and B' of FIG. 3A.

As represented in FIG. 4A, the cross section shape of the intra cortical lens implant is that of an ellipse.

However, in other embodiments not represented here, the outer outline of the intra cortical lens implant in a front view plane as that of FIG. 4A may assume other shapes, e.g. with recesses and bumps, or a perfect circle.

Figure 4B:
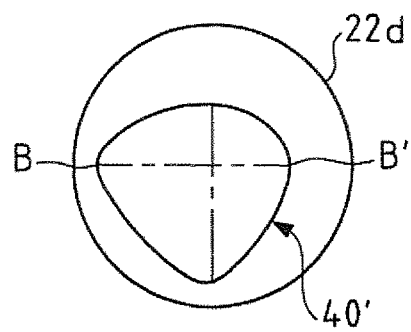

FIG. 4B illustrates a front view of an intra cortical lens implant 40' according to a variant embodiment located inside capsular bag 22d. The implant 40' has the same overall features as implant 40 of FIG. 3A except that the left and right side portions of the intra cortical lens implant relative to the polar axis of the implant, and thus, points B and B', are not symmetrical to each other. The intra cortical lens implant has therefore not an axi-symmetrical shape relative to its longitudinal axis when viewed in a front plane. Here the polar axis of the implant does not match the optical axis X of the lens.

As shown in FIGS. 4A and 4B embodiments, the intra cortical lens implant can take various forms in cross sectional planes that are perpendicular to the polar axis of the implant and to any sagittal plane thereof. As represented in FIG. 4B, the radial extension of the implant 40' is not the same in every radial direction.

Figure 5:
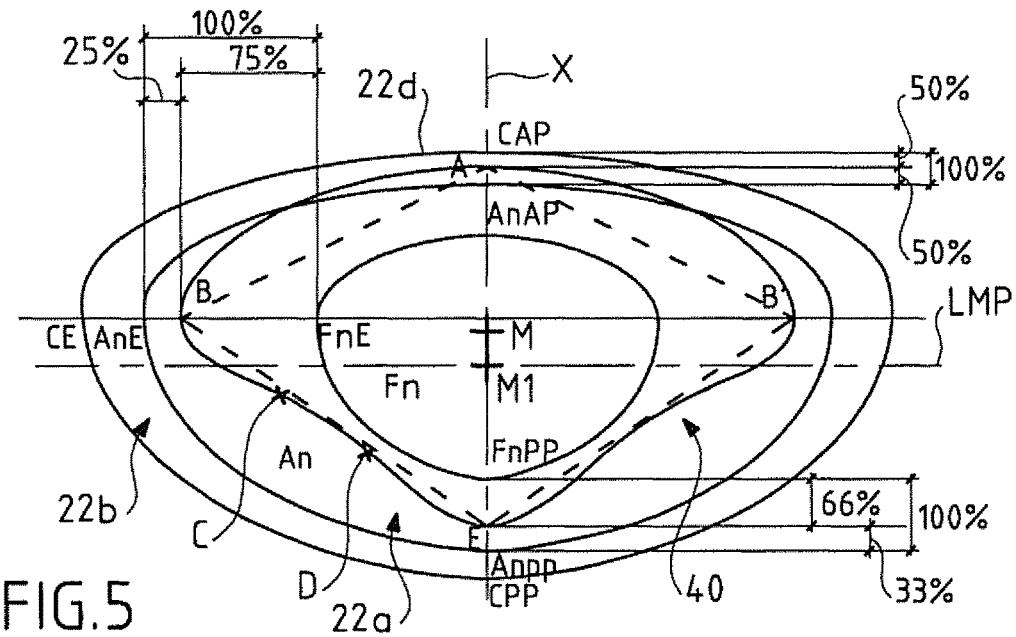
FIG. 5 represents a sagittal view of FIG. 3A intra cortical lens implant in a crystalline lens.

FIG. 5 is a sagittal cross section of the intra cortical lens implant 40 inside the capsular bag 22d of the crystalline lens and surrounded by a remaining natural part of the lens. The intra cortical lens implant occupies a part of the lens that has been previously removed as will be seen subsequently Several salient geometrical and physiological points/zones have been identified in the sagittal cross section of the lens as follows:

CAP designates the anterior pole of the crystalline lens that is located on the optical axis X (as already mentioned above, here the polar axis of the implant coincides with the optical axis of the lens X);

CE designates the lens equator (this is a physiological zone surrounding the lens);

AnE designates the adult nucleus equator;

FnE designates the fetal nucleus equator (this is a physiological zone surrounding the embryonic nucleus);

AnPP designates the adult nucleus posterior pole;

CPP designates the cortex posterior pole;

FnPP designates the fetal nucleus posterior pole; and

AnAP designates the adult nucleus anterior pole.

FnE is represented on the contour of the fetal nucleus (at the location it would occupy if the nucleus were present in the lens) and the same holds true for FnPP.

In an embodiment, these above geometrical and physiological points/zones may satisfy the following simple mathematical relations that are also illustrated in FIG. 5 for intra cortical lens implant 40:

$$[A, \text{AnAP}] = \tfrac{1}{2}[\text{CAP}, \text{AnAP}] \quad (1)$$

$$[B, \text{FnE}] = \tfrac{3}{4}[\text{AnE}, \text{FnE}] \quad (2)$$

$$[E, \text{FnPP}] = \tfrac{2}{3}[\text{AnPP}, \text{FnPP}] \quad (3).$$

When relation (1) is satisfied this means that there is a sufficient anterior distance and therefore a sufficient thickness of a more rigid part between the soft implant 40 and the capsular bag 22d so that sufficient relative rigidity is achieved between the non treated lens (mainly the cortex) and the intra cortical lens implant in the anterior part of the lens.

This sufficient thickness of the anterior rigid layer or shell surrounding the intra cortical lens implant makes it possible to redirect the stresses from the zonules towards the central zone of the lens, i.e. the implant. This relation may also hold true for other intra cortical lens implant shapes.

A minimal distance above 150 μm between any point of the outer shape of the implant 40 (or any other implant according to the invention) and the lens external capsule profile ensures that the active cells of the epithelium will not be damaged by the presence of the implant.

When relation (2) is satisfied this means that there is a sufficient equatorial rigid transmission zone around the intra cortical lens implant since the zonules are connected to this zone (FIG. 5) and therefore exert a mechanical tension or stress thereon during the accommodative process.

As represented in FIG. 5, a soft intra cortical lens implant is surrounded by a more rigid part of the natural crystalline lens. The softness/flexibility of the implant enables its compression when the zonules exert a tautness on the lens, in particular in the central zone of the implant that would correspond to the nucleus. This is because the rigid/stiff posterior part of the natural (genuine) crystalline lens that is located between the posterior part of the intra cortical lens implant and the capsular bag serves as a rigid basis for the implant in order to give rise to a spring effect.

Depending on the shape of the intra cortical lens implant the axial extension of the rigid part located behind the posterior part of the implant may be more or less great provided that it is sufficient for producing the above effect. In other words the posterior part of the natural crystalline lens has to keep its structural stiffness and appropriate mechanical reaction as much as possible in order to round the lens when releasing zonules 24 for near vision. According to above relation (3), a sufficient volume of posterior natural tissues remains in the lens to make it possible for the intra cortical lens implant to produce such a spring effect.

The shape of the soft/flexible anterior part of the intra cortical lens implant enables a change in the outer curvature of this anterior part when the zonules exert a tautness on the lens.

More particularly, as explained in relation with FIG. 3A, the shape of the outer outline O1 and O2 in the anterior part of the intra cortical lens implant causes an increase in the thickness of the rigid/stiff posterior part of the natural crystalline lens when moving from anterior pole AP towards the periphery of the lens. This makes it possible to control the quadratic moment of the shape and, therefore, maximize the transmission of the zonular effort and appropriate consecutive central deformation of the lens (flattening).

All that has just been mentioned above in relation with FIG. 5 (in particular as regards the technical effects and functions) equally applies to any other shape of implant according to the invention.

Generally speaking the intra cortical lens implant 40, as well as any other implant according to the invention, is mainly located in the anterior part of the lens so as to give rise to the above-described technical effects. This is illustrated, by example, in FIG. 5 by the relative position between the intra cortical lens implant 40 and the lens. M is the mid-point located on the segment that connects the anterior pole A and the posterior pole E of the implant and LMP represents the lens plane that is perpendicular to the polar axis (optical axis X) and crosses the latter at point M1 that is midway the lens poles CAP and CPP. Thus, mid-point M is located above plane LMP in FIG. 5, i.e. it is located in the anterior part of the lens. This explanation holds true for any other implant according to the invention.

To be noted that the outer outline of any implant according to the invention must not have sharp angles but a smooth shape so as to best mechanically cooperate with the surrounding crystalline lens and avoid to cause any injury thereto. Local stresses and optical artefacts can thus be avoided.

Non-axisymmetry of the intra cortical lens implant in some embodiments may induce desired optical features (ex: desired astigmatism) such as a controlled increase in the depth of field.

Overall the implant according to the invention (whatever its embodiments/shapes) gives rise to a new accommodative amplitude that makes the lens flatter than it is for far vision when submitted to zonules constraints (decrease in curvature) and elastic enough to come back to a rounder shape when ciliary muscle contracts. The thus obtained rounder shape is equivalent to the previous possible roundest shape (obtained for the lens without the implant) but might go beyond the latter in some instances.

Thus, a new offset is needed for this new optical system. This offset could be reached through any kind of stromal refractive surgery e.g. by changing the curvature of the cornea or by creating internal optical diopters in the same modified lens material/zone.

FIG. 5 illustrates the four points A, B, E and B' of the intra cortical lens implant forming a quadrilateral in dashed lines that is here inscribed within the outer shape of the intra cortical lens implant 40. This quadrilateral may also be present in any other intra cortical lens implant according to the invention and the shape of the implant develops around or is based on this quadrilateral.

FIG. 6 illustrates a variant embodiment of a non axisymmetric intra cortical lens implant 50 inside a crystalline lens 60 in a sagittal plane including optical axis X of the lens. Here the polar axis A'E' of the implant 50 does not coincide with optical axis X of the lens. The intra cortical lens implant 50 has two left and side portions 50a and 50b that are not symmetrical to each other relative to the polar axis A'E' for the anterior part of the intra cortical lens implant as well as for the posterior part thereof. The right side portion is smaller than the left side portion and, more particularly, the right side portion has an anterior part that has a smaller radial extension than the left side.

Further, the posterior part 50c, 50d of each of left and side portions 50a and 50b is dramatically asymmetrical since:
the outer outline of the right side portion 50b makes a smaller angle to axis X than that of left side portion 50a;

the curvatures of the different portions of each of the left and right side portions posterior part are inverted and there are not as many portions in both left and right side portions: for left side portion 50*a*, two outwardly convex shapes flank a central concave portion whereas, for right side portion 50*b*, there are only a convex portion and a concave adjacent to each other.

Such an asymmetry causes astigmatism and therefore an increase in the depth of field.

The intra cortical lens implant covers here completely the fetal nucleus 62 of the lens.

Such an asymmetrical shape enables the suppression of mechanical blocking of the lens accommodative mechanism which is due to the natural increase in the relative rigidity of the nucleus with age.

Overall the intra cortical lens implant according to the invention is tailored to the patient's eye and, e.g. may be adjusted either for correcting astigmatism and/or for compensating a non desired deformation in the lens.

To be noted that the main features of this implant 50 correspond overall to that of implant 40, in particular, as regards the anterior part of each left and side portion and their posterior part and the relative position of the intra cortical lens implant in the lens, the quadrilateral structure ABEB' etc. The shapes are however somewhat different as well as the values for the angles, curvature radii, radial extension etc.

In addition, FIG. 6 also illustrates another possible configuration that better defines the location of an intra cortical lens implant inside a lens.

In the present embodiment the anterior pole A' and the posterior pole E' of the implant are located inside an infinite cylinder (or at least a cylinder that is as long as crystalline lens thickness or height on FIG. 6) 63 centered about axis X and having a diameter of approximately 2 mm. Here the polar axis A'E' of the implant intersects optical axis X. However, this may not be the case in other configurations where both axis may be parallel to each other.

The above may apply to any other implant according to the invention and helps to better define the location of an intra cortical lens implant inside a lens whatever the shape of the latter and its axi- or non-axi-symmetrical shape. Such a definition also contributes to the overall technical effects of the intra cortical lens implant, e.g. as those already described above in relation with FIGS. 3A and 5.

Further, here M' is the mid-point located on the polar axis and LMP' represents the lens plane that is perpendicular to the optical axis X and crosses the latter at point M'1 that is midway the lens poles CAP' and CPP'. Thus, mid-point M' is located above plane LMP' in FIG. 6 (at a distance h therefrom), i.e. it is located in the anterior part of the lens, for the same reasons as in FIG. 5.

FIGS. 7A and 7B schematically illustrate in a crystalline lens CL (in a sagittal plane and in a front plane viewed in a cross section according to AA) the extreme volumes V1 and V2 that can be occupied by an implant according to the invention.

Overall the volume of the intra cortical lens implant according to the invention (whatever its shape and location) is between 10% and 90% of the crystalline lens inner volume (these values may be taken) so as to provide the lens with appropriate elasticity or flexibility.

A minimal volume V1 of 10% approximately corresponds to the volume of the fetal nucleus (Fn).

A maximal volume V2 of 90% approximately encompasses the whole nucleus 22*a* and may even encroach locally upon the cortex 22*b*.

These extreme volumes/sizes represent respectively the minimal and maximal overall functional zones to be treated but do not identify the accurate geometries and relative positions of the intra cortical lens implants that will occupy each of these zones or zones in-between. The intra cortical lens implant geometries may somewhat differ from the overall geometry of the functional zones.

Overall, the intra cortical lens implant may take various forms the volume of which lies between 10% and 90% of the crystalline lens inner volume. However, the outer shape of the intra cortical lens implant must not locally be too close to the epithelium as already described with reference to FIG. 5 (not at less than 150 µm from the external capsule profile).

FIGS. 7C and 7D schematically illustrate in a crystalline lens CL' (in a sagittal plane and in a front plane viewed in a cross section according to AA) possible intra cortical lens implant shapes and volumes according to the invention. Again the quadrilateral formed by the four points A, B, E and B' has been represented.

For example, the intra cortical lens implant S in solid lines represents a possible implant shape corresponding to a functional zone located in between the two extreme volumes. The implant S has a volume of approximately 20% of the crystalline lens inner volume. Implant S does not wholly cover fetal nucleus (Fn) but a major portion thereof and here the whole anterior part of fetal nucleus is covered. Only small posterior portions of the fetal nucleus are not covered. This shape evolves around the fetal nucleus shape. Implant S is not axi-symmetrical relative to axis X (and to its polar axis) and angles θ and θ' for the two side portions of the intra cortical lens implant in FIG. 7C are different from each other.

The outer outline of intra cortical lens implant shape S includes curvatures and rounded edges that more precisely define an appropriate shape tailored to a patient's eye. This shape may be the result of the use of a simulation model together with clinical measurements performed on the patient's eye as will be further described.

Whatever the accurate shapes the intra cortical lens implant may assume it has to occupy a part of the natural crystalline lens that includes at least a major portion of the fetal nucleus so as to restore flexibility in this core zone relative to a more rigid/stiffer surrounding zone of the untreated natural lens. The flexibility restoration in this zone of the lens is necessary to allow the lens shape to be deformed as desired during the accommodative process.

In some instances, the juvenile and adult (An) layers of the nucleus may also be at least partly impacted/covered by the intra cortical lens implant as represented by the intra cortical lens implant S.

In FIGS. 7C and 7D another shape S' represents a possible intra cortical lens implant shape with a volume of approximately 60% of the crystalline lens inner volume that locally covers an anterior portion of the cortex. Implant S' also covers the major portion of adult nucleus (An). The 60% volume value of the total crystalline lens inner volume represents a preferred value in terms of technical effects according to the invention.

When the intra cortical lens implant encroaches upon the cortex there should not be excessive overlap with the anterior and posterior cortex so as to keep the functionalities described above (sufficient thickness of rigid anterior and posterior cortex for the distribution of stress and spring effect etc.).

For instance, the intra cortical lens implant of FIG. 5 occupies 50% of the lens inner volume and 35% for the FIG. 6 intra cortical lens implant.

All that has been described above in relation with FIGS. 3A, 5 and 6 may also apply here to intra cortical lens implants that occupy the extreme functional volumes/zones as well as intermediate volumes/zones, in particular, regarding the anterior part of the crystalline lens and the posterior rigid part of the natural crystalline lens, and more generally, regarding the relative position of the intra cortical lens implant to the lens (main location in the anterior part of the lens, polar axis within a given cylinder etc.).

Given the implant volumes requirements explained above, the angles θ and θ' illustrated in FIG. 3A may each lie between 1° and 90° as explained above for an axi-symmetrical intra cortical lens implant shape (all the sagittal cross sections are the same and θ=θ').

If the angle θ is less than 1°, the intra cortical lens implant will be too small to produce a mechanical effect on the crystalline lens and the flexibility brought by the intra cortical lens implant will therefore not provide the lens with enough accommodative amplitude.

Conversely, if the angle θ is greater than 90°, the intra cortical lens implant will be less efficient since either a too large portion of cortex will be occupied by the implant or a too small portion of nucleus will be affected by the implant. The spring effect will therefore disappear.

More particularly, the above angle may be comprised in a narrower range lying between 15° and 75° to provide better results (the intra cortical lens implant thus covers a greater zone of the lens including the equatorial diameter and better manages the distribution of stresses in the implanted lens).

Still more particularly, the above angle may be comprised in a still narrower range lying between 30° and 60° to provide even better results and, more preferably, between 45° and 60°. An angle of 60° is an example in the present embodiment.

The above discussion regarding the values of the angles θ and θ' applies equally if the intra cortical lens implant has not an axi-symmetrical configuration.

However, for a non axi-symmetrical configuration other aspects may be envisaged for the angles θ and θ' since it has to be kept in mind that the implant volume has to be overall between V1 and V2 (these values may be included) as explained above.

In particular, in one or more given sagittal sections the angles θ and θ' may be both (or only one of them) locally either small, e.g. less than 1° or great, e.g. greater than 90° provided that the overall implant volume meets the above requirements. In other words, the angles have to be properly balanced all around the polar axis so as to ensure a minimal zone for the implant.

According to another possible configuration, if, in one or more sagittal sections, the angle θ has a value of 1° or of a few degrees, then the other angle θ' may have a greater value provided that the overall implant volume meets the above requirements.

According to still another possible configuration, the value of 90° for the angles θ and θ' is preferably not reached at the same time in one and the same sagittal section (for the two side portions of the implant in this section). In this respect, if one angle takes the value of 90°, then the other angle is preferably less than 90° so that the posterior part still takes a convex shape overall and a quadrilateral ABEB' be still present in the implant shape.

Figure 8A:
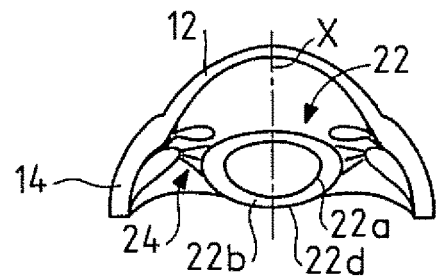
FIGS. 8A-N are views illustrating different steps performed in some of the methods of FIG. 9.
Figure 8B:
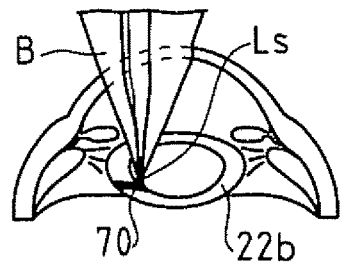
Figure 8C:
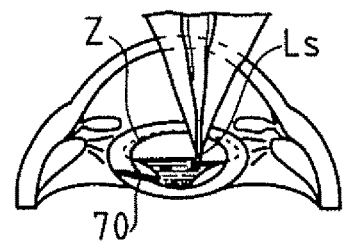
Figure 8D:
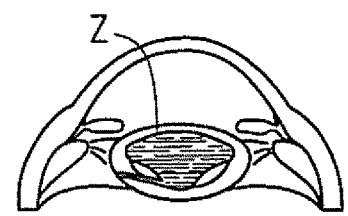
Figure 8E:
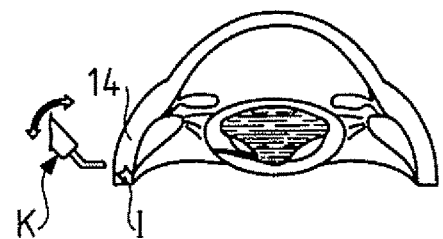
Figure 8F:
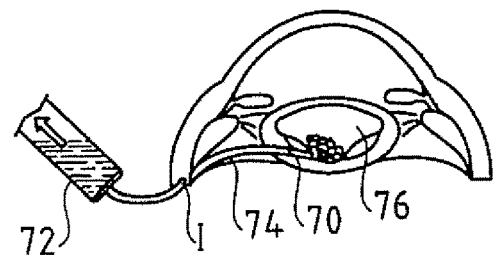
Figure 8G:
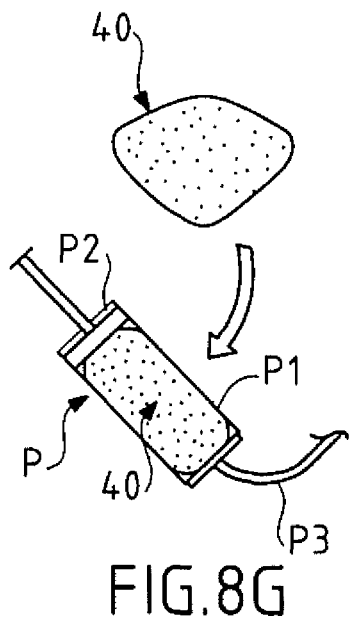
Figure 8H:
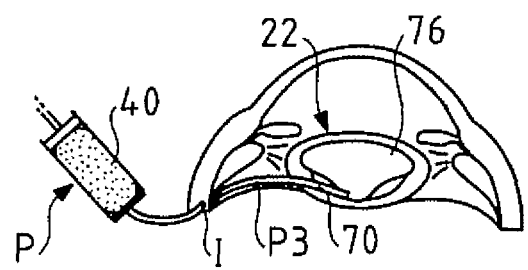
Figure 8I:
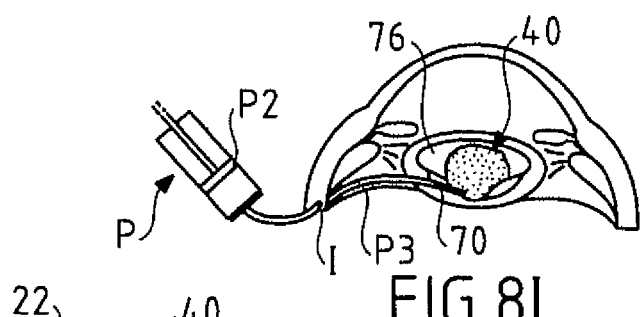
Figure 8J:
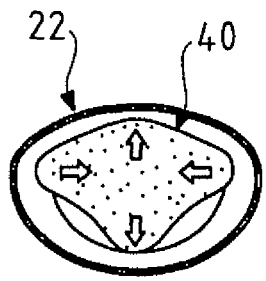
Figure 8K:
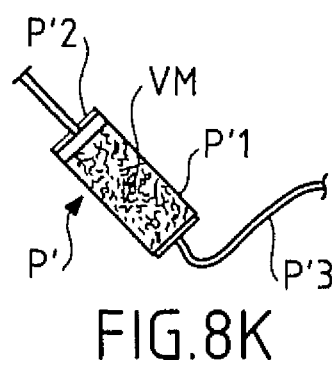
Figure 8L:
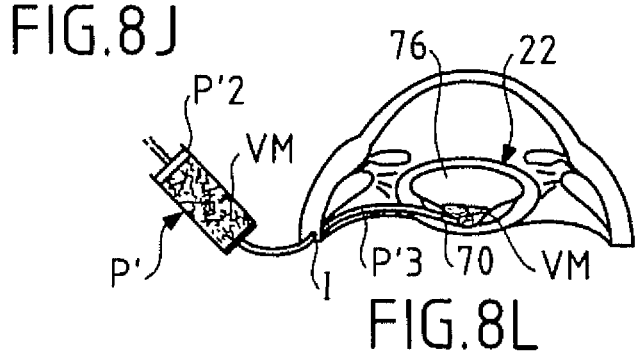
Figure 8M:
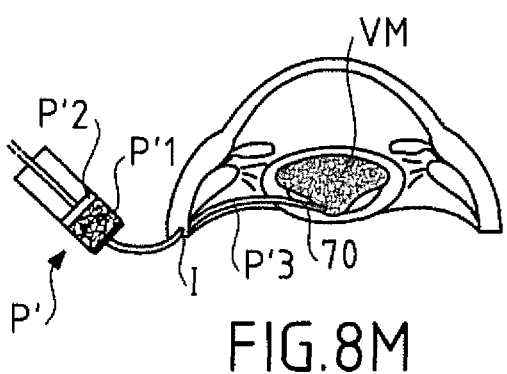
Figure 8N:
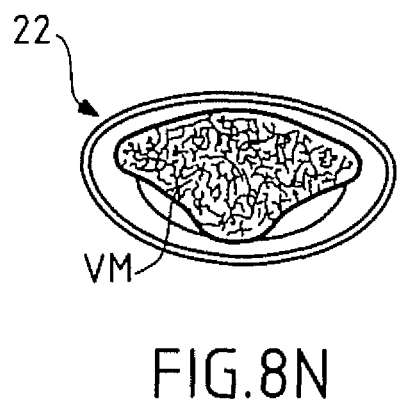

FIGS. 8A-N schematically represent different views of methods steps for putting in place intra cortical lens implants according to embodiments of the invention in a crystalline lens such as any one of the implants described above. By way of example, the intra cortical lens implant 40 will be considered for one embodiment (FIGS. 8A-J).

An example embodiment of possible methods is illustrated in FIG. 9.

An example of an appropriate apparatus and associated equipment for implementing at least several steps of these methods will be described further with reference to FIG. 10.

FIG. 8A illustrates in a sagittal plane the eye 10 of a patient (as in FIG. 1) with a natural crystalline lens affected with presbyopia disorders such as the one described with reference to FIG. 2. For the sake of simplicity, only the nucleus 22a surrounded by the cortex 22b have been represented inside the capsular bag 22d in FIG. 8A.

The methods illustrated in FIG. 9 includes several steps that spread over time. The steps may be grouped in three phases:

a first conventional imaging phase during which measurements and observations relating to a patient are performed and a diagnosis may also be made based on these previous results and data (steps S1 and S2); during this phase biometric data representing dimensional, mechanical and optical properties of the patient's eye are obtained;

a second phase during which mechanical and visual simulation is performed based on the previous phase results (steps S3 to S6);

and a third phase in the course of which a lens implant is introduced in the patient's crystalline lens or the latter is treated/modified, e.g. in accordance with the simulation results (steps S7 to S23).

The first and second prior phases are common to the following steps of possible different methods for placing an implant inside a crystalline lens (ex: FIGS. 8A-N and 11A-M) or of a method for treating a crystalline lens without introducing any implant (ex: FIGS. 12A-F). Overall these prior phases may be used before any other method for putting in place an implant inside a crystalline lens or any other method for treating a crystalline lens without introducing any implant. The methods illustrated in FIGS. 8A-N, 11A-M and 12A-F and that are described after the performance of the first and second prior phases in the present description may alternatively be performed without using these first and second prior phases. Overall the diagnosis made on the patient's eye(s) makes it possible to give a clear picture of the aging grade of the crystalline lens(es). Based on such a diagnosis the most appropriate implant (intra cortical or intra capsular lens implant to replace in whole or in part the inner volume of the lens by an accommodative lens device) and/or treatment is selected. In addition, the diagnosis of the aging grade of a lens may identify other optical disorders than presbyopia. Thus, the above selection may also be made according to such other optical disorders.

According to the first step S1 (first phase), the patient is installed in a position where he/she is maintained immobile during the implementation of the method, e.g. he/she is seated or lies on an operating table.

Next step S2 (first phase) is a step of imaging the eye through conventional imaging method and associated equipment such as Optical Coherence Tomography (OCT).

By way of example, an apparatus called IOL Master 700 from Zeiss may be used for performing this imaging step. Such an apparatus provides a full-length OCT image showing anatomical details on a longitudinal cut through the entire eye.

Other OCT imaging methods and associated equipment as described in the following documents the content of which is hereby incorporated by reference: U.S. Pat. No. 6,004,314

("Optical coherence tomography assisted surgical apparatus"), U.S. Pat. No. 6,741,359 ("Optical coherence tomography optical scanner"), U.S. Pat. No. 8,908,189 ("Systems and methods for swept-source optical coherence tomography") and US2016166147 ("Optical coherence tomography system") may also be used for performing imaging step S2.

Different conventional imaging methods and associated equipment may alternatively be used for performing imaging step S2.

In the course of imaging step S2 clinical or biometric data representative of the patient's eye geometry (physical characteristics of the eye) are obtained such as: nucleus posterior curvature radius, nucleus thickness, nucleus equatorial diameter, anteroposterior nucleus thickness ratio, nucleus anteroposterior position, pupil diameter, iris width (to scleral spur), eye length, vitreous size (height), intraocular pressure, anterior zonula insertion, anterior zonula attachment band width, equatorial zonula insertion, equatorial zonula attachment band width, posterior zonula insertion, posterior zonula attachment band width, ciliary scleral spur, ciliary apex anteroposterior position.

Other measurements/data may be derived from the above data through extrapolation such as scleral inner curvature radius, scleral external curvature radius, posterior scleral thickness and epithelium thickness.

The above results (biometric data of the patient) makes it possible for the ophthalmologist (diagnosis) to identify and quantify the loss for visual accommodative amplitude of the eye, the residual accommodation capability, the axial displacement of the lens along the optical axis, as well as the ratio between the nucleus and the cortex and, more generally, the aging grade of the lens. Some of these results may alternatively be directly measured without the help of the ophthalmologist.

Next step S3 concerns the second phase and may be performed just after the first phase or subsequently, e.g. several days afterwards.

Step S3 is a step of simulation that is based on the results of the imaging and diagnosis which are representative of the patient's eye anatomy. Also statistical clinical data, for instance characterizing several physics-related parameters, may concern a sample of crystalline lens and may be used during this step. Such statistical data may be built on the basis of studies performed on representative samples of patients, accumulated imaging and classified in accordance with several criteria such as age, ethnicity, gender, etc.

For example, data characterizing a refractive index in relation to the age of a crystalline may be used Simulation step S3 may be performed through optical simulation using a conventional simulator instrument such as the one described in US 2016296110 ("miniature simultaneous vision simulator instrument") the content of which is hereby incorporated by reference.

This step aims at simulating the vision through optical corrections set in the simulator instrument which are representative of the vision through a lens accommodative implant as though it were installed inside the patient's lens.

For the performance of the simulation the ophthalmologist selects the shape and dimensions of the implant to be put in place inside the patient's crystalline lens (curvature radii of the anterior and posterior parts, diameter of the equatorial plane, thickness along the polar axis etc. for both the most and the least accommodated positions of the lens, etc.), location of the implant in the crystalline lens (zone of the lens concerned, e.g. with respect to the different zones described with reference to FIGS. 7A-B) based on the above measurements/data (biometric data), observations and diagnosis while possibly taking into account the description of the above embodiments (see for example FIGS. 3A-B, 4A-B, 5 and 7A-B).

Then test step S4 is performed. If the results of the simulation step are not in accordance with the aim to be achieved (increase in the lens flexibility and in the accommodative power of the aged patient's eye), then test step S4 leads to a new iteration and step S3 is repeated.

In a variant embodiment not illustrated here, step S3 may be achieved during the first phase.

Steps S5 and S6 illustrate another alternative embodiment that may take place instead of step S3. According to this new embodiment the simulation may be achieved differently and combine clinical measurements performed on the patient's eye (eye imaging), possibly with statistical clinical data, with a generic mechanical and optical model of a human eye for producing better quality simulation results. The generic mechanical and optical model of the eye that is used here will be more thoroughly described subsequently with reference to FIG. 13 and following. This model integrates, on the one hand, a 3D representation of an eye with mechanical links between the eye's components and variables parameters that can be adjusted by a user or by automatic inputs from imaging and, on the other hand, a conventional calculation module which includes, in particular, physical equations, ray-tracing module etc. The conventional calculation module is for example a software product called Comsol Multiphysics.

Figure 13:
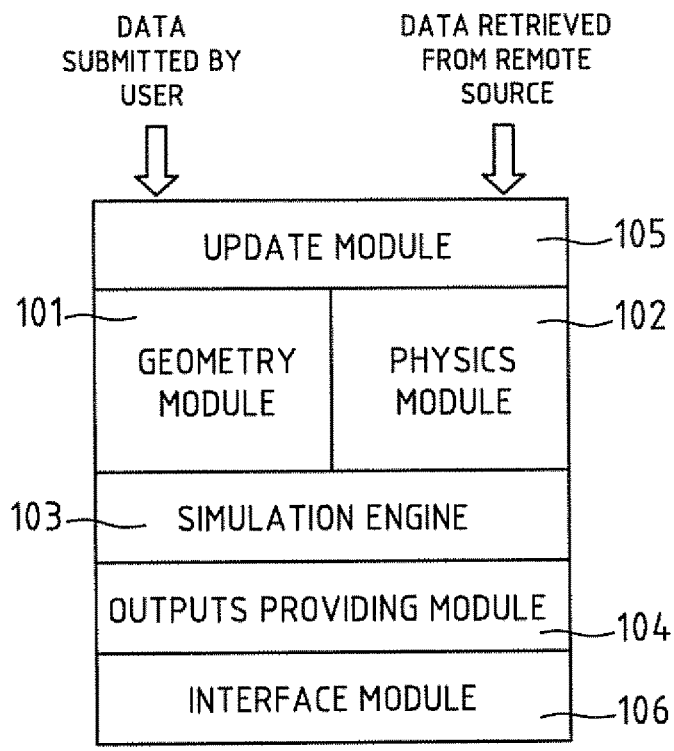
FIG. 13 is a schematic view of the main components of a computer system.

Statistical clinical data as already described above in relation with step S3 is stored in a dedicated database that is part of the system 100 of FIG. 13. Advantageously, the statistical data may be correlated to the patient to be treated by extracting from it mean values in relation to the patient's profile. Accordingly, an additional step of sorting the statistical data extracted from the database in relation to one or more characteristics that are specific to the patient to be treated, for instance the patient's age or the patient's gender, may be provided here before using such data.

Computational modeling step S5 includes an updating sub-step of the model and a calibration sub-step thereof.

In the updating sub-step measurements/data obtained in the course of imaging step S2 and possible statistical clinical data are entered into the generic mechanical and optical model as parameters of this model of the eye so that the model become faithfully representative of the patient's eye through computation. This updating sub-step of the model may concern parameters such as mechanical parameters and geometrical parameters (e.g. parameters relating to the relative positions between the elements/components of the model, parameters relating to the geometry of the elements/components etc.), parameters relating to optical and/or mechanical properties of materials/components etc. . . . .

Further a calibration sub-step of the model is performed through computation so that the optical properties of the latter be adapted to that of the patient's eye.

In particular, the refractive index of the lens is selected/adjusted through the model (by calculation) so that the latter correctly positions an image of an object on the retina in near and far vision so as to be representative of the same visual characteristics as those of the patient's eye.

To be noted that other parameters may be adjusted likewise during the calibration step.

After this calibration sub-step, the model is now representative of the patient's eye, in particular of the crystalline lens before surgery.

Next simulation step S6 may be performed. In this step, the ophthalmologist selects the features of a possible implant to be placed in the patient's lens (e.g.: shape, dimensions, location, material(s)/substance(s) used for the implant etc.) and enters them into the model in order to simulate the mechanical behavior of this implant in the eye's model, as though it were placed in the patient's eye. In other words, the practitioner provides the updated model with possible geometrical and/or mechanical corrections in order to determine the mechanical behavior of the updated model through simulation. Practically, data generated by the calculation module of the model will inform the ophthalmologist of, e.g. possible concentration of stresses at a particular location in the lens, undesired deformation of the lens etc. If the results are not satisfactory, then at least one of the above features of the implant is modified and entered into the model and the above process is repeated as often as necessary.

Once the mechanical and geometrical aspects of the implant have been validated, optical results of the implant have to be checked.

Optical simulation is performed using the above calculation module and ray-tracing module which simulates the emission of optical beams, their passage through the simulated/modelled representation of the patient's eye with the simulated/modelled implant and the resulting beams after traversing the patient's implanted eye model and their location/spot size on the retina. During this phase the practitioner provides the updated model with possible optical corrections in order to determine the optical behavior of the updated model through simulation.

According to the results of the test step S4, the optical simulation results may lead to validate the mechanically selected/defined implant or to alter the latter and perform again the previous steps S5 and S6, in particular the mechanical and optical simulation steps, until validating the features of an implant.

Once the simulation phase has been achieved the geometry and mechanical and optical properties of the implant that gave rise to the desired simulated optical results (restoration of flexibility and increased amplitude of accommodation) have been determined and validated by the practitioner. The corresponding implant can then be selected on the shelves if available or planned for the manufacture if customized. In case no implant is to be inserted into the patient's lens, then the corresponding surgical method may be planned and performed (see for example the method of step S23 and FIGS. 12A-F).

Implanting or treating the patient's crystalline lens may be performed based on the above simulation results. Put it another way, these results will be used for determining/setting up operating parameters for a surgical piece of equipment or tool or apparatus so that the latter be operative to apply the validated mechanical and optical corrections to the patient's crystalline lens. This applies equally the methods for putting in place an intra cortical lens implant or an intra capsular lens implant and to the electromagnetic treatment method.

Following steps S7 to S23 concern the third phase and possible surgical methods for treating/implanting the patient's crystalline lens in view of increasing visual accommodative amplitude in a patient's eye.

Two methods for placing an intra cortical lens implant in the patient's lens are described in steps S7 to S16 and illustrated in FIGS. 8A-N. Steps S7 to S10 are common to the two methods.

In step S7 an access or passage is created inside the lens (zone Z). More particularly, a channel 70 is formed in the cortex 22b (FIG. 8B), e.g. by drilling, in order to provide access (e.g. syringe access) to the zone Z from outside the lens capsule. The thus formed cortical channel may exit outside the lens capsule or not depending on the method used for channeling and the aim to be achieved.

For instance, electromagnetic treatment/processing may be used for channeling and perforation of the lens capsule at one end of the channel may be performed at the same time.

Step S7 is used in the described two surgical methods but may be optional in relation with other surgical methods for treating the crystalline lens. For example, if the method does not use any implant (as in FIGS. 12A-F), then step S7 may be omitted.

More particularly, in step S7 the electromagnetic treatment may be a laser treatment. An example of an apparatus and associated equipment used for performing this step will be described subsequently with reference to FIG. 10.

FIG. 8B illustrates a laser beam B and a laser spot Ls that is focused on the lens. In FIG. 8B, the channel 70 has been formed. However, at the very beginning of the laser process, the laser spot Ls is focused on a posterior region of the capsule (under the epithelium) and moves along a predetermined inclined direction so as to connect the outside of the capsule to the inner central zone of the lens which will be further treated/processed with a view to accommodating the intra cortical lens implant. The laser treatment/processing aims at removing the tissues and forming channel 70 connecting the zone Z to the outside surface of the lens capsule. More details on the laser treatment/processing will be given in connection with the following step.

Other alternative methods for lens channeling may be envisaged such as laser treatment using a laser apparatus as a cutting apparatus or instrument.

The posterior location of the lens channel makes it possible not to affect the epithelium. The side location enables easy access to the lens channel through the sclera.

Other alternative locations for the lens drilling/channeling may be envisaged.

It is to be noted that this step which is the first step of a surgical method may be carried out several hours or days after the last simulation step S3 or S6.

FIG. 8C identifies in the lens 22 of FIG. 8B a zone Z (partly illustrated in dotted lines) that is to be treated/processed before putting in place the intra cortical lens implant 40 in this zone. This zone Z here partially covers the nucleus and the cortex. The geometry and location of this zone are known from the previous steps, in particular S6, and are tailored to the patient.

Step S8 concerns the electromagnetic treatment of zone Z that uses, for example, the same apparatus and associated equipment as above.

In the present embodiment zone Z is laser processed so as to produce photoablation of the zone and create a cavity inside the lens. The operating laser parameters for photoablation will be described with reference to FIG. 10. Photoablation is a conventional process used in eye's surgery. To be noted that step S7 illustrated in FIG. 8B may also be performed by photoablation.

FIG. 8C illustrates a laser spot Ls that is focused on a region of zone Z. The laser spot is programmed in the above apparatus to scan the whole zone Z, starting by the posterior part thereof (close to the posterior part of the cortex 22b) and moving forward towards the anterior part of the zone (close to the anterior part of the cortex) in the direction of the optical axis X. By analogy, the scanning process is carried out as in a known 3D printing process. The laser spot removes the tissues by transferring the laser energy to the zone Z where the tissues are vaporized. The zone Z is therefore laser processed by scanning successive layers, layer by layer as diagrammatically illustrated in FIG. 8C (each layer is defined in a plane that is perpendicular to axis X). Operating parameters used for the photoablation will be provided subsequently.

In alternative embodiments zone Z may be processed differently for ablating the tissues of the zone, e.g. through radiofrequencies, UltraSounds, UV radiation, etc. For instance, a Phacoemulsification technique may alternatively be applied here.

FIG. 8D represents the lens after core zone Z has been prepared for subsequent installation of the intra cortical lens implant.

Steps S7 and S8 may be inverted or performed at the same time.

In step S9 an incision I is made in the sclera 14 (one or more incisions may be made) so as to provide access to the lens from outside the eye. For instance a conventional surgical tool such as a calibrated knife K may be used as represented in FIG. 8E.

To be noted that any cut, incision or opening made in the sclera, the cornea or lens should be as watertight as possible for subsequent quick sealing. For example a Z-shaped opening or openings in a sagittal view may be envisaged. Any cut, incision or opening may be made by any conventional technique.

This incision step may be omitted if no implant is put in place in the lens and only electromagnetic treatment/processing of the lens is performed to alter the latter so as to provide it with new accommodative amplitude (ex: FIGS. 12A-F). Steps S8 and S9 may be inverted in a variant embodiment.

Further step S10 is an extraction step of the natural material (tissues) of the lens that has been ablated in the zone Z as illustrated in FIG. 8F. This step may include the perforation of the capsule if it has not been done during step S7.

Extraction of the material is performed through channel 70 connecting zone Z to outside surface of the lens capsule (once the channel has been opened to the outside either by photoablation or by any other surgical method/instrument) and through the sclera incision I using a conventional instrument that is connected to a phacoemulsification equipment. The phacoemulsification equipment is a microprocessor-based machine which controls fluid dynamics through the microprocessor. The equipment includes a peristaltic or Venturi type of pump for sucking out the lens material. FIG. 8F partially represents such a pump with an aspiration chamber or reservoir 72 disposed outside the eye and connected to a flexible connecting duct 74 that has been previously inserted into the sclera incision I and the channel 70 so as to establish communication between the zone Z and the chamber 72. When the pump is operated the material and tissues debris are sucked out through the duct and reach the chamber where they may be collected or where they just go through before being collected or evacuated elsewhere as indicated by the arrow.

Such a technique is described for example in U.S. Pat. No. 5,154,696 ("Phacoemulsification, irrigation and aspiration method and apparatus") and US2002099400 ("Method and apparatus for lenticular liquefaction and aspiration"), the content of which is hereby incorporated by reference.

After complete extraction a cavity 76 has been freed up inside the natural lens 22 so as to enable insertion of implant 40 therein. The shape of the outside outline of the intra cortical lens implant corresponds to the shape of the cavity (so that the implant is in contact with the cavity wall at any point) apart from the dimensions of the implant that may differ to some extent as will be further described.

After these common steps S7-10, two surgical methods will now be described: a first method according to steps S11-13 (FIGS. 8G-J) and a second method according to steps S14-16 (FIGS. 8K-N).

According to the first method step S11, illustrated by FIG. 8G, is a preparation step during which intra cortical lens implant 40 is introduced into a piston or syringe type device P. Device P comprises a chamber P1 and a piston P2 that is configured to axially slide within chamber P1 when pushed forward through its rod. A hollow insertion tip or cannula P3 with flexibility capabilities is connected to the device and in communication with the interior of the chamber. The implant 40 is introduced in the chamber before placing the piston. As the implant 40 is a flexible or malleable material or combination of materials with elastic or visco-elastic and cohesive properties it can be elastically deformed under external stress to be accommodated within the chamber and the piston is placed in the upper position. Alternatively, preparation step S11 may be omitted within the described method. In such a case, this step is performed beforehand: the device P is already pre-loaded with implant 40 and therefore ready for use by the surgeon as a kit assembly in the described method.

Next device P is connected to lens 22 by inserting tip P3 successively through sclera incision I and channel 70 during an installation step S12 (FIG. 8H). Thus installed, the distal end of the tip opens out within cavity 76.

As illustrated by FIG. 8I, the implant 40 is progressively inserted in the cavity 76 (step S13) by pushing forward the piston P2, which forces the implant to further elastically deform in order to be introduced inside tip P3, and pushed inside the latter along the whole length thereof until it enters into cavity 76. The implant 40 being pushed by the piston expands within cavity 76 as it progressively exits the distal end of tip P3 and the constraints exerted by the walls of the tip do no longer apply on the implant. The inserted intra cortical lens implant fills in the space within the cavity. This insertion or injection step (device P may be viewed as an injectable device in which the intra cortical lens implant or any other intra cortical lens implant according to the invention is loaded; a pre-loaded injectable device of this type may be envisaged) is made possible thanks to the elasticity or flexibility of the implant.

The shape of the implant 40 has greater dimensions than those of the internal cavity. Thus, when the intra cortical lens implant expands within the cavity it is maintained in a (slightly) compressed state and closely spouses the inner wall delineating the cavity. The difference between the volume of the intra cortical lens implant and that of the emptied cavity is for example between 2 and 5%.

A further aspect of the invention which does not depend on the shape and localization of an intra cortical lens implant within the lens is that a difference in volume between the implant and the clear cavity may induce a controlled deformation of the lens. The shape of the lens may then be changed/altered by this volume difference. The intra cortical lens implant may assume any convenient shape that makes it possible to induce a controlled desired deformation of the lens. The shapes of the intra cortical lens implant and the cavity lens will adapt to each other. A simulation process may be helpful to ensure that there will be mechanical contact at any point between the shape of the intra cortical lens implant and the lens cavity and that the induced deformation will be the desired one. In particular, the lens deformation may take place along the polar axis where the intra cortical lens implant is the most mechanically constrained, which induces a more curved lens as illustrated in FIG. 8J by the internal arrows. In other words, the intra cortical lens implant causes the remaining natural tissues of the lens to be rounded up when inserted in the lens.

Where necessary, the cornea 12 may also be laser processed so as to modify the curvature of the cornea. In this case the laser apparatus is used as a cutting apparatus or instrument. This optional step (laser refractive surgery) may take place after the laser apparatus has been used at step S7 or S8 or at any other time. In the present embodiment, this optional step may be achieved at the following step Sn (Control of Refraction and possible enhancement) in FIG. 9. The operating parameters of the laser apparatus will be adapted to this specific step. When the crystalline lens has been modified by the above intra cortical lens implant, it has been given a new amplitude of accommodation with two new extreme shapes (one is more curved while the other is more flattened in the respective two extreme positions of the altered accommodative lens) and a new refractive index. It may happen that this new refractive index does not correspond to the desired one whatever the reason. In such a case recalibration of the eye has to be made so that the eye in a non-accommodated state (the lens is as flat as possible) may see far objects in an acceptable manner without any correction. Thus the whole eye optical system has improved since it has obtained an increase in accommodative amplitude for near vision. Then a change in the curvature of the cornea by refractive surgery turns out to be necessary to proceed to this recalibration. In contrast, if the new refractive index does correspond to the desired one, no change has to be made in the cornea. To be noted that step Sn may also be carried out after each of the other methods and, in particular, after steps S16, S20, S22 and S23. Further step Sn may provide data to the statistical clinical data to update the latter. Overall step Sn may be viewed as a further diagnosis step which takes place after the patient's crystalline lens has been optically corrected to ensure achievement of the desired optical results (either in terms of presbyopia correction or any other optical disorder correction).

According to the second method of intra cortical lens implantation, step S14, illustrated by FIG. 8K, is a preparation step during which one or more viscoelastic materials (a mixture or compound of viscoelastic materials), called hereinafter the viscoelastic material VM, (the viscoelastic material or materials have a refractive index that is suitable for being used in a crystalline lens) are introduced into a piston or syringe type device P'. The viscoelastic material VM has viscoelastic properties that confer flexibility to the core part of the lens as with the implant 40. Device P' comprises a chamber P'1 and a piston P'2 that is configured to axially slide within chamber P'1 when pushed forward through its rod. A hollow insertion tip or cannula P'3 with flexibility capabilities is connected to the device so as to be in communication with the interior of the chamber. The viscoelastic material VM (e.g. a gel) is introduced in the chamber before placing the piston. Alternatively, it may be preloaded in the device well in advance (for example, the viscoelastic material may be pre-loaded by the device manufacturer) and the preloaded device may then be ready for use by the surgeon.

Next device P' is connected to lens 22 by inserting tip P'3 successively through sclera incision I and channel 70 during an installation step S15 as in FIG. 8L. Thus installed, the distal end of the tip opens out within cavity 76 (FIG. 8L).

In the course of step S16 (FIG. 8M) the fillable or injectable visco-elastic material VM is injected through tip P'3 to fill in the cavity 76 by pushing forward the piston P'2, which forces the flexible/malleable substance to elastically deform in order to be successively introduced inside tip P'3 and pushed inside the latter along the whole length thereof until it enters into cavity 76. The visco-elastic material being further pushed by the piston fills in the space within cavity 76 as it progressively exits the distal end of tip P'3 and the constraints exerted by the walls of the tip do no longer apply. Once the injection has been achieved the injected visco-elastic material VM perfectly spouses the shape of the inner wall delineating the cavity. The injected visco-elastic material VM behaves as an intra cortical lens implant, such as elastically deformable implant 40, and produces the same mechanical effects, in particular in terms of flexibility/softness so that it is able to provide new visual accommodative amplitude to the natural lens (this is an increase in the accommodative amplitude of the lens compared to the situation of the aged natural lens before the implantation).

FIG. 8N illustrates the new implanted lens in which the visco-elastic material VM may have a shear modulus of, e.g. 500 Pa or 1000 Pa (or other equivalent mechanical property). The shear modulus (or other equivalent mechanical property) for the visco-elastic material VM is generally less than that for an elastic implant as that of FIG. 8J and, for example, less than 1500 Pa. The surrounding part of the lens has for its part here a shear modulus between 1500-10000 Pa. The intra cortical lens implant will not reach the value of 1500 Pa if the surrounding part is known to be at 1500 Pa so as to respect the difference in the flexibility/rigidity between the intra cortical lens implant and the surrounding part; otherwise the spring effect would no longer apply.

Device P' may be viewed as an injectable device in which the visco-elastic material or any other substance according to the invention is loaded; a pre-loaded injectable device of this type may be envisaged.

For example, such a visco-elastic material may include siloxane (polysiloxane), hydrophilic gel.

Examples of substances called OVDs (acronym for "Ophtalmic Viscoelastic Devices") that are suitable for the visco-elastic material VM can be found in the following documents, the content of which is hereby incorporated by reference: WO2016203381 ("Viscoelastic preparation for use in surgical methods of ophthalmic surgery"), WO2006034383 ("Viscoelastic solution or gel formulation, and methods of treating a body site with the same"), U.S. Pat. No. 5,103,840 ("Viscoelastic collagen gel for ophthalmic surgery"), U.S. Pat. No. 4,965,253 ("Viscoelastic material for ophthalmic surgery").

Examples of suitable OVDs may be provided by the company Zeiss under the following commercial names and the main technical characteristics (these substances are commercialized pre-packaged in a syringe and therefore ready to use):

Visthesia 1.5% which is a viscoanesthetic OVD (substance: sodium hyaluronate; concentration: 1.5% NaHa, 1.0% lidocaine; volume: 0.8 ml inside the intra-cameral syringe; pH: 7.0-7.6; osmolality in mOsmol/kg: 280-330; molecular weight in Da: 2,900,000 on average; pseudoplasticity index: 80; zero-shear viscosity in mPa·s: 187,000 on average);

Visthesia 1.0% which is a viscoanesthetic OVD (substance: sodium hyaluronate; concentration: 1.0% NaHa, 1.0% lidocaine; volume: 0.8 ml inside the intra-cameral syringe; pH: 7.0-7.6; osmolality in mOsmol/kg: 280-330; molecular weight in Da: 2,900,000 on average; pseudoplasticity index: 58; zero-shear viscosity in mPa·s: 63,000 on average);

Z-Hyalin plus which is a high-viscosity OVD (substance: sodium hyaluronate; concentration: 1.5% NaHa; volume: 1.0 ml inside the intracameral syringe; pH: 7.2-7.6; osmolality in mOsmol/kg: 300-360; molecular weight in Da: 2,900,000 on average; pseudoplasticity index: 91; zero-shear viscosity in mPa·s: 250,000 on average);

Z-Hyalin which is a high-viscosity OVD (substance: sodium hyaluronate; concentration: 1.0% NaHa; volume: 1.0 ml inside the intracameral syringe; pH: 7.2-7.6; osmolality in mOsmol/kg: 300-350; molecular weight in Da: 2,900,000 on average; pseudoplasticity index: 50; zero-shear viscosity in mPa·s: 50,000 on average).

Also silicon oils may be employed for the visco-elastic material VM. Such substances are known today for their use in vitroretinal surgery.

Examples of suitable silicon oils are the following:

ZEISS-RT SIL-OL 1000 commercialized by the company Zeiss (composition: 100% ultra pure polydimethylsiloxane; viscosity of 1,050+/−150 mPas at 25° C.; specific weight of 0.97+/−0.01 g/cm3 at 25° C.; refractive index of 1.403+/−0.003 at 25° C.; OH end group content: 100 ppm; low molecular components (oligosiloxanes): 100 ppm);

SIL-1000-S Silicone Oil Syringe (a syringe of 10 ml) commercialized by the company Dutch Ophtalmic, USA is an ultra-purified silicone oil which leads a maximum interfacial tension and minimizes interaction between tissues, cells and endo-tamponades media (viscosity: 1,000-1,500 mPas; refractive index: 1.40; specific gravity: 0.97 g/cm3 at 25° C.; surface tension: 21 mN/m against air; interfacial tension: 40 mN/m against water);

SIL-5000-S Silicone Oil Syringe (a syringe of 10 ml) commercialized by the company Dutch Ophtalmic, USA is an ultra-purified silicone oil which leads a maximum interfacial tension and minimizes interaction between tissues, cells and endo-tamponades media (viscosity: 5,000 and 5,900 mPas; refractive index: 1.40; specific gravity: 0.97 g/cm3 at 25° C.; surface tension: 21 mN/m against air; interfacial tension: 40 mN/m against water).

To be noted that fluids such as gas or liquids may be used alternatively according to the desired mechanical and optical results for filling in the cavity 76 of the lens and constituting the core part of the lens.

Figure 10:
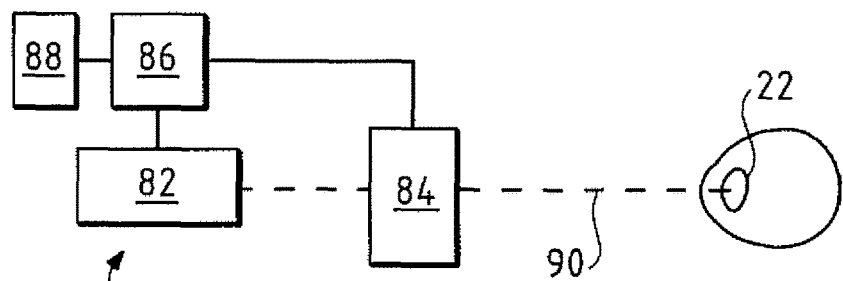
FIG. 10 is an example embodiment of an apparatus used in different embodiments of the invention.

FIG. 10 illustrates an embodiment of a system 80 used in the electromagnetic treatment/processing of a patient crystalline lens 22 according to the invention.

System 80 generates electromagnetic radiation and focuses it into the crystalline lens 22 of a patient eye.

System 80 comprises an apparatus 82 for generating electromagnetic radiation and a control device 84 such as a collimator for controlling and adjusting the direction of the generated radiation under the control of a data processing unit 86 or microprocessor and associated computer-readable storage media 88 (ex: memory or memories). Microprocessor unit 86 is also configured to operate apparatus 82 under the control of a computer program stored in computer-readable storage media 88.

In a particular embodiment, apparatus 82 is a laser, e.g. a femtosecond laser which delivers a beam 90 together with control device 84 focused onto crystalline lens 22 under the control of programmed microprocessor unit 86.

An example of femtosecond laser for performing laser phacofragmentation in the course of cataract surgery is commercially available from LenSx Lasers, Inc of Aliso Viejo, Calif. and may be used for carrying out steps in the methods of FIG. 9.

A Z8 Ziemer laser apparatus may alternatively be used. Such an apparatus is described in US2014098347 ("Ophtalmological device") the content of which is hereby incorporated by reference.

However, other types of laser may alternatively be used here.

A femtosecond laser has been used for ablating a lens during cataract surgery in US 2010/0191226. The content of this patent application is hereby incorporated by reference in particular as regards the laser ablation process.

Here, the femtosecond laser 82 is a laser of the YAG type and operates with the following parameters to carry out photoablation:

wavelength between 800 and 2000 nm;
frequency between 0.1 and 1 MHz;
spot diameter between 1 and 10 μm;
interaction time between 500 and 1000 femtosecond and
energy between 0.1 and 100 μJ (the intensity may be deduced from the energy and interaction time values).

These parameters are also used in step S6 (lens opening) when the laser apparatus is employed.

In step S7 of FIG. 9 and FIG. 8C the femtosecond laser 82 proceeds from a posterior region in zone Z towards an anterior region thereof (postero-anterior direction) and from the periphery of zone Z to the center thereof.

The path or trajectory to be followed by beam 90 for ablating the natural material of zone Z is programmed by the surgeon according to the results of steps S2 to S5.

To be noted that another type of laser source may be used when a setting of optical offset has to be made in the cornea as described above. In this case an excimer laser may be used and operates in accordance with the following parameters:

wavelength between 100 and 400 nm;
frequency between 0.1 and 10 kHz;
spot diameter between 100 and 1000 μm;
interaction time between 0.1 and 100 nanosecond and
energy between 0.1 and 10 mJ.

Such a type of excimer laser is described in US2016120700 ("Intastromal Corneal Reshaping Method and Apparatus for Correction of Refractive Errors Using Ultra Short and Ultra-Intensive Laser Pulses") the content of which is hereby incorporated by reference.

A laser apparatus commercialized by the Zeiss company under the commercial name VisuMax or MEL80 may be used here.

Another embodiment concerns an intra capsular lens implant that is intended to wholly fill in the capsular bag of a crystalline lens after the natural material (tissues etc.) contained in the latter has been wholly removed.

FIG. 11A illustrates a crystalline lens 122 including the natural material 122a (different successive layers: nucleus, cortex and epithelium) contained within the capsular bag 122b. Natural material 122a is as described above with reference to FIG. 2. The cornea 112, the sclera 114, the zonules 124 are represented as in FIG. 8A.

Two methods for putting in place two new intra capsular lens implants respectively will now be described with reference to FIGS. 11B to 11H and steps S17 to S22 of FIG. 9. Steps S17 to S19 are common to both methods.

In FIG. 11B a surgeon creates one or more corneal incisions I' in the cornea 112 (step S17) to provide access to the anterior chamber 116 and lens 122 using a conventional instrument 126. Instrument 126 is here a calibrated knife.

Alternatively, a laser apparatus may be used as a cutting instrument as already described above.

Next FIG. 11C illustrates a step S18 of creation of an opening of the lens 122 by tearing and lifting a cap or cover of the lens capsule as indicated by 127. This opening is called capsulorexhis and is made using a conventional instrument 128 introduced through incision I'. Instrument 128 may be capsulorexhis forceps.

Alternatively, the instrument or tool may be a femtosecond laser.

FIG. 11D corresponds to a step S19 during which the whole content of capsular bag 122b is being fragmented e.g. in accordance with the phacoemulsification surgery using a probe such as an ultrasonic handpiece 130 with a titanium or steel needle. Ultrasonic handpiece 130 is introduced through incision I' and in contact with the lens material/tissues through opening O. The tip of the needle vibrates at ultrasonic frequencies in order to sculpt and emulsify the tissues while aspirating fragments through the tip thanks to a pump or aspirator equipment (a peristaltic or Venturi type of pump) as illustrated in FIG. 11E. The conventional phacoemulsification equipment is a microprocessor-based machine which controls fluid dynamics through the microprocessor. Reference is also made to above step S10 of FIG. 9 for completing this description.

Extraction of the fragments (FIG. 11E) is here performed using a conventional instrument that is connected to a phacoemulsification equipment.

Such a technique of phacoemulsification surgery is described for example in U.S. Pat. No. 5,154,696 ("Phacoemulsification, irrigation and aspiration method and apparatus") and US2002099400 ("Method and apparatus for lenticular liquefaction and aspiration"), the content of which is hereby incorporated by reference.

In the end of the extraction step void has been created inside natural capsular bag 122b that remains intact but with an opening in its anterior part after capsulorhexis.

FIG. 11F represents a new intra capsular lens implant 130 which comprises two parts/zones: a soft central or core part/zone 132 corresponding in this example to implant 40 of FIGS. 3 and 5 (other examples of implant may be envisaged provided they have the main characteristics as the above described implants regarding their softness/flexibility and their anterior and posterior portions) and a peripheral more rigid part/zone, called shell part, 134 which surrounds less rigid core part 132. The shell part 134 plays the role of the natural surrounding zone in FIG. 5. The intra capsular lens implant may be considered as a one-piece unit even though the two parts have different mechanical characteristics (and possibly different materials). The intra capsular lens implant may be a bi-component implant with the two components being assembled together during the implant manufacture. The bi-component intra capsular lens implant may also be considered as a one-piece unit for the user.

In the present embodiment of this intra capsular lens implant, the materials used for each part/zone may be different (the materials for the two parts/zones are completely different in their composition): the material used for core part 132 may be the same as for implant 40 whereas the material used for the shell part 134 may be different. Alternatively, the same basic material may be used for both parts/zones but it is altered/changed either by modifying its composition or by a subsequent treatment/process (such as heating the material for cross-linking/curing polymers differently depending on the parts/zones and therefore increasing the rigidity of the material concerned) with a view to obtaining different shear modulus.

Thus, the core part/zone may have a shear modulus less than 10 kPa, e.g. equal to 250 Pa, and the shell part/zone may have a shear modulus of 750 Pa.

By way of example, the materials used for the intra capsular lens implant may be, e.g. HEMA, silicon etc. More particularly, cross-linked polydimethyl siloxanes reinforced with silica may be used. Cross-linking (curing) may be obtained by different manners: radical, hydrosilylation, condensation etc.

FIG. 11G illustrates a step S20 of insertion of intra capsular lens implant 130 inside the capsular bag 122b to fill in the void. Implant 130 is seized by a clamp instrument 136, introduced through corneal incision I' and placed within open capsular bag 122b so as to tension the inner wall of capsular bag 122b and come into close contact therewith. This insertion step is similar to that used in a process for inserting a conventional IOL in a lens where the haptics help to tension/stretch the capsular bag.

Implant 130 is therefore surrounded by the inner wall of capsular bag 122b apart from the upper region with opening O.

To be noted that in some instances, depending on the materials used for the intra capsular lens implant, conventional biological glue may be used to cause the capsule 122b to adhere to the implant 130.

FIG. 11H represents the new crystalline lens with the intra capsular lens implant 130. The opening O is left unclosed. Thanks to this new intra capsular lens implant the lens is provided with increased accommodative amplitude as explained above for the other embodiments.

A method for putting in place another new intra capsular lens implant according to another embodiment of the invention will now be described with reference to FIGS. 11I-N and steps S21-22. This method takes over the general steps S17 to S19 of FIG. 9 and FIGS. 11A-E as previously described.

Figure 11I:
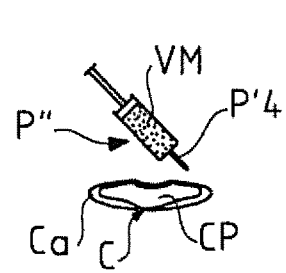

FIG. 11I illustrates both a piston or syringe-type device P''' similar to that of FIG. 8K and a closed flexible hollow envelope or shell C. Envelope C is represented in a cross-section in FIG. 11I and comprises a shell part or membrane Ca made in a soft material such as a material that is used for the envelopes of the breast prosthesis. For instance, silicon elastomer or an hydrophilic or hydrophobic polymer may be used for the material of the envelope. This material must be tear-resistant. Shell part Ca of FIG. 11I has a variable thickness along its circumference so as to define the outline of a central cavity Cp. Shell part may have a substantially annular shape.

Envelope or shell C also comprises a core or central cavity Cp surrounded by this soft shell part Ca. In FIG. 11I core cavity Cp does not contain any substance or material. Device P''' is filled in with viscoelastic material such as in FIG. 8K and differs from device P' in that flexible hollow tip P'3 is replaced by a rigid rectilinear hollow tip P'4.

Figure 11J:
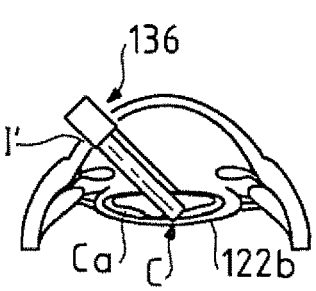

In FIG. 11J envelope C is handled by a clamp instrument 136 and introduced through incision I' so as to be placed within open capsular bag 122b and tension the latter so as to be in close contact with the inner wall of capsular bag 122b (step S21).

Figure 11K:
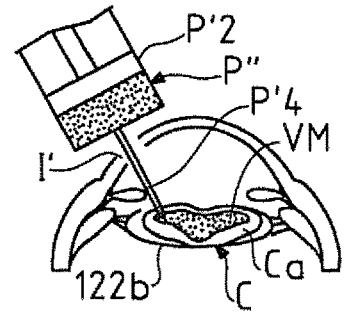

As represented in FIG. 11K, sharp tip P'4 is introduced through incision I', perforates shell part Ca of envelope C until reaching the core cavity Cp so as to fill in the latter when piston P'2 is actuated as already described with reference to FIG. 8M (step S22).

Once the core cavity Cp has been filled in with viscoelastic material, device P''' is withdrawn.

The injected viscoelastic material may be the same as the above material VM, and is of the gel-type for example. The viscoelastic material may also be pre-loaded in an injection device.

Figure 11L:
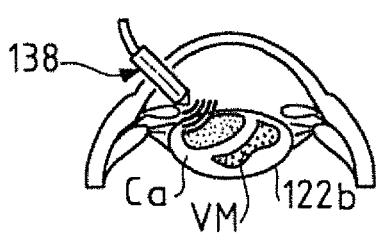

Next an instrument 138 that is configured to suture/close the small aperture made in the shell part Ca by tip P'4 is installed inside the anterior chamber in close proximity to the shell part (FIG. 11L). This instrument may generate, e.g. UV, thermal waves, RF etc. so as to cure/vulcanize the outer thin wall of the shell part.

In the present embodiment, this instrument may further cure/vulcanize the injected viscoelastic material VM so as to obtain the desired properties (viscosity etc.) for providing an intra capsular lens implant with relative flexibility/rigidity between the shell part Ca (more rigid) and the filled core part (more flexible). However, this further step may be omitted in some cases where the injected viscoelastic material VM has already the desired appropriate mechanical properties to form a soft core implant part.

Other instruments/methods may alternatively be used for suturing/closing the small aperture made in the shell as well as for curing/vulcanizing the injected substance and/or the substance in the annular portion. The degree of cure/vulcanization may vary according to the mechanical and optical results to be achieved.

Figure 11M:
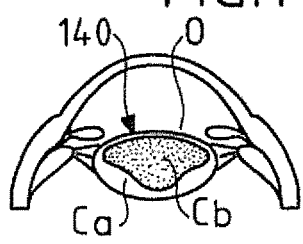

FIG. 11M illustrates the new crystalline lens with the intra capsular lens implant 140 which comprises shell part Ca surrounding core part Cb. The variable thickness of shell part defines in a complementary manner the outer shape of core part Cb. The two complementary shapes substantially reproduce the shapes of the implant 40 and surrounding natural tissues (mainly cortex) in the crystalline lens of FIG. 5. The opening O is left unclosed. Thanks to this new intra capsular lens implant flexibility and therefore accommodative amplitude of the natural lens is increased as explained above for the other embodiments. The same mechanical properties as for intra capsular lens implant 130 are obtained here for intra capsular lens implant 140.

In a variant embodiment the shell part Ca of envelope C is already filled with a visco-elastic material such as a gel, e.g. of the silicone gel or silicone elastomer type. For example, an appropriate silicon elastomer may be polydimethylsiloxane, polydiphenyl-siloxane or some combination of the two. This variant embodiment does not modify the above-described following operations in connection with FIGS. 11J to 11M.

Optionally, the visco-elastic material in shell part Ca may also be cured/vulcanized to increase its rigidity (i.e. reduce its flexibility) relative to the filled core part during the step illustrated in FIG. 11L.

In another variant embodiment, the core part Cb may be filled in by a fluid such as a liquid or a gas which will confer elasticity to the implant relative to a more rigid shell part.

In still another variant embodiment, the filled-in device P''' with hollow tip P'4 is already assembled with envelope C (through a temporary fixation, e.g. of the mechanical type or by biological glue) and therefore ready for use as a kit assembly (pre-loaded device). Device P''' with hollow tip P'4 can be easily separated from envelope C when the filling operation has been achieved, e.g. through a conventional instrument such as flat forceps.

In another embodiment the crystalline lens of the patient eye is treated/processed differently for restoring flexibility and increasing accommodative amplitude in a crystalline lens without placing any implant inside. The following surgical treatment/method may follow the steps S1 to S6 of FIG. 9 and be represented by step S23. Optionally, step Sn may be carried out afterwards as already mentioned for other surgical methods.

Electromagnetic radiation is applied to the lens in order to create an inner shape or modify an inner zone of the lens, such as the shape of implant 40 or the zone it occupies in the lens (FIG. 5) and bring to the lens appropriate mechanical properties in terms of softness/flexibility and optical properties (refractive index, diopter etc.). The remainder of the lens remains unmodified as in the FIGS. 3A and 5 embodiment. To be noted that any other shape of intra cortical lens implant such as those illustrated in FIGS. 5, 6, 7A-D may be obtained through appropriate electromagnetic treatment.

Figure 12A:
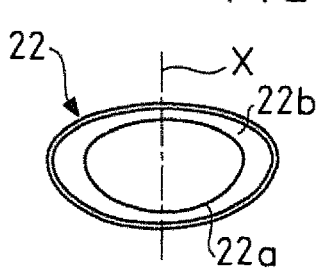
FIGS. 12A-F are views illustrating different steps performed in a method for electromagnetically treating a patient's crystalline lens.
Figure 12B:
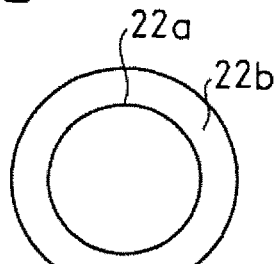

FIGS. 12A and 12B illustrate lens 22 of FIG. 2 in a sagittal view and front view respectively.

Electromagnetic radiation is applied to the specific zone of the lens identified by zone Z that is identical to that of FIG. 8C in order to modify the mechanical characteristics of this zone by breaking the links at the macromolecular level and the links between the layers so as to increase slip between the layers. In other words the structural resistance of this zone to the deformation is reduced. Such a treatment also modifies the optical properties (e. g. by shifting the refractive index) of the treated zone.

To be noted that the present description of this embodiment applies to any shape/zone internal to the crystalline lens and that provides the above-described technical effects and functions of the implant according to the invention (e.g. the mechanical implants, their shapes and locations within the crystalline lens as well as the mechanical and optical properties as illustrated in FIGS. 3A-B, 4A-B and 5). In particular, the present description also applies to the volumes and zones described in relation with FIGS. 7A-B.

Figure 12C:
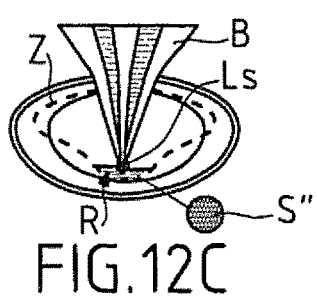
Figure 12D:
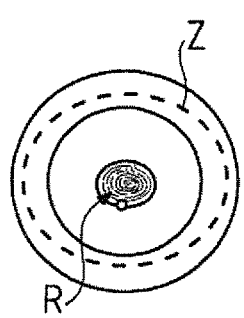

FIGS. 12C and 12D illustrate an example of electromagnetic treatment of zone Z on the views of FIGS. 12A and 12B respectively in accordance with step S23 of FIG. 9.

An example of electromagnetic radiation treatment system is given by the use of a femtosecond laser as that described above in relation with the ablation process and FIGS. 8B-C and 10.

As illustrated by FIGS. 12C and 12D the laser beam produces a laser beam B with a laser spot Ls which is first focused on the posterior part of zone Z. As explained above in relation with FIGS. 8B and 8C, the laser spot follows a predetermined trajectory or scan path from the posterior part of zone Z towards the anterior part thereof so as to homogeneously process the whole zone by successive smaller zones. Here, the laser spot describes a spiral path and as represented a first region R has already been laser processed at the posterior part of zone Z. S" is a partial enlarged view of an example laser pattern applied to the zone. The description of FIGS. 8B and 8C may also apply here as regards details of the operation. The operating parameters are however different. The coordinates of the spot are controlled by the processor of the apparatus in accordance with the predetermined scanning pattern. Other predetermined scanning patterns may alternatively be envisaged for yielding the same result.

Figure 12E:
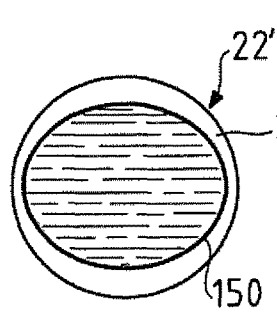
Figure 12F:
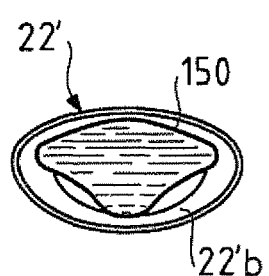
Figure 12G:
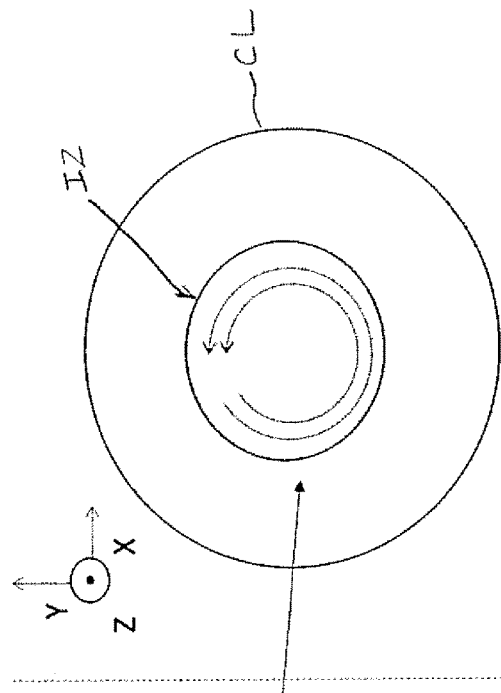
Figure 12H:
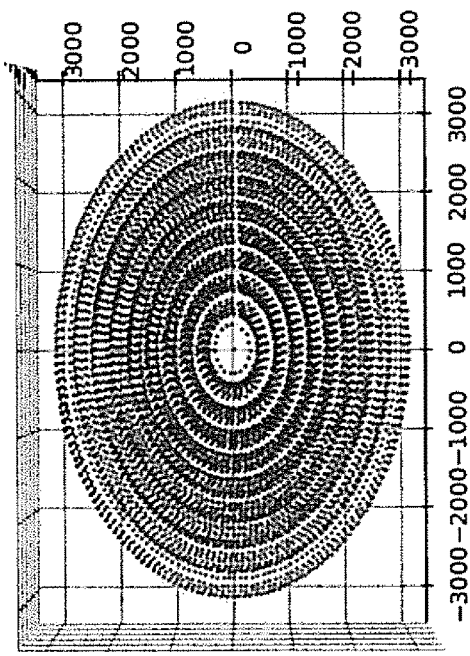

The result of the laser treatment/processing is illustrated in FIG. 12E (front view) and FIG. 12F (sagittal view) where the core 150 has been achieved. Core 150 has the same or similar features as above implant 40. In particular, it has softer/more flexible tissues and a higher refractive index than the natural surrounding part 22'b of the new lens 22'. Such a method for altering/modifying lens 22 is not invasive.

FIGS. 12G-J illustrate examples regarding application of a possible electromagnetic pattern (laser or ultrasound) on an inner zone IZ of a crystalline lens CL. Such electromagnetic treatment may be performed by successive passes or stages according to x, y and z coordinates as illustrated by the three axes in FIGS. 12G and 12H. The electromagnetic apparatus used for this treatment, e.g. of the above type (ex: femtosecond laser 82 of FIG. 10) or of a type described below, may be lifted or lowered according to z-axis. It may be placed on a mobile table in this respect.

According to this example the inner zone to be treated/processed is discretized in a plurality of strips or layers (in dotted lines on FIG. 12G) along axis z. For each strip of layer (FIG. 12H) the laser spot or ultrasound beam is driven (through an x, y scanner accessory/function) so as to describe successive concentric circles from the center or the periphery (successive passes in the same strip or layer). Once a strip or layer has been treated the laser spot or ultrasound beam is shifted to another one and the same or similar pattern is applied. All the strips or layers are therefore successively treated likewise.

Figure 12I:
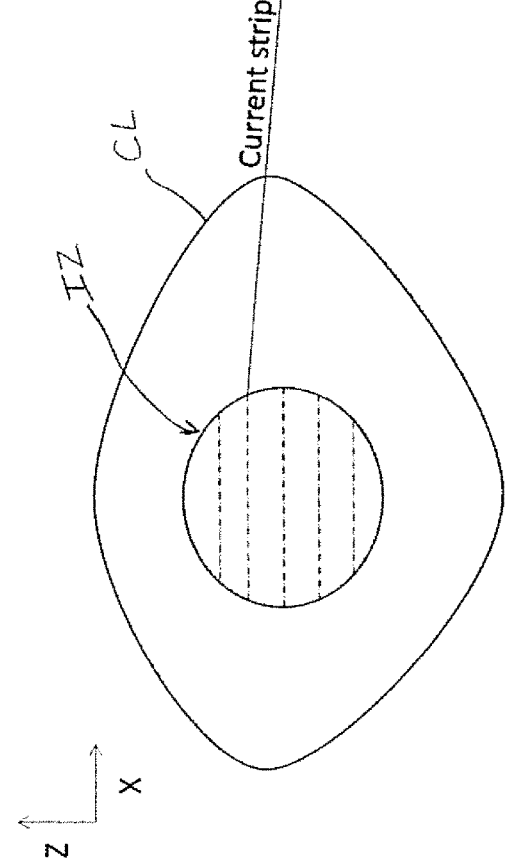
Figure 12I:
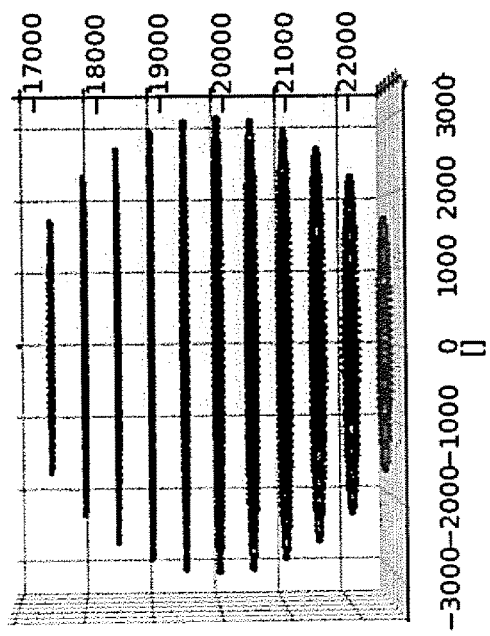

FIGS. 12I and 12J illustrate numerical examples (in micrometers) of laser patterns in a plurality of strips or layers along z axis (FIG. 12I) and viewed from above in the x,y plane.

In a general manner which does not necessarily depend on the above examples, the electromagnetic treatment of an inner lens zone for correcting optical disorders such as presbyopia (e.g. which has been defined by virtue of the FIG. 9 process through simulation) may be characterized by any of the following features:

the smallest beam size is that obtained by focusing the beam or spot on a point (the point may be a sphere or an ellipsoid);

the spacing between the successive points (in every direction x, y and z); this parameter is useful when managing the superimposition of the immediate effects produced by the beam or spot, for example if continuous or discontinuous treatment/process is searched for, and also for limiting or highlighting the immediate cumulative effects (in case of overlapping immediate effects);

the spacing between the points at the end of the treatment/process and therefore potentially after several passes; for example a point (obtained by an electromagnetic spot) may be added after other points and therefore be geometrically inserted; this may prove to be useful for treating the whole volume while avoiding the cumulative treatment/processing effects since a rest time will be left before exciting the material again;

the treatment order: the points that are geometrically juxtaposed may not be treated successively so as to leave them time for latency;

the number of identical passes: a same point may be impacted again so as to take advantage of the controlled cumulative effects with rest time;

Thus, the points that make up the volume may be treated in a non-successive manner while ensuring that treatment does not modify/forbid access to the zones that have not been treated by radiation yet.

Successive layers or strips may be treated/processed. Then intermediary layers or strips may be treated or new points may be treated in the existing layers or strips.

In order to modify the crystalline lens according to the present embodiment the femtosecond laser 82 of FIG. 10 may have the following characteristics or operating parameters (energetic parameters):

wavelength between 800 nm and 2000 nm;
frequency between 1 Hz ad 10 MHz;
spot diameter between 0.5 µm and 5 µm;
interaction time between 100 and 500 femtosecond;
energy between 0.1 and 10 nJ.

Also operating parameters defining the spatial geometry of the spot or beam (axial position of the spot or beam, shape of the envelope that circumscribes the inner lens zone) are set up.

These operating parameters are adapted to the patient's eye and have been determined based on the result of simulation step S6 (or test S4) of FIG. 9. The apparatus thus set up with these adapted operating parameters is therefore able to modify the natural lens of the patient's eye so as to correct the specific presbyopia disorders the patient's eye is affected with. The processor of the apparatus is therefore programmed with these parameters to produce a laser spot or beam that follows a predetermined scanning pattern (selected by the surgeon among plural possible predetermined scanning patterns or automatically) and processes the zone of interest Z.

The advantage in this embodiment is that no invasive action has to be performed on the lens to correct presbyopia and/or any other optical disorder or disease.

To be noted that other electromagnetic apparatuses may alternatively be used for treating/processing an inner lens zone as zone Z of FIGS. 12C-F and modifying it so as to correct presbyopia disorders as explained above with the femtosecond laser. For example, an HIFU (High Intensity Focused Ultrasound) generator may be used such as the one described in US 2017027751 which is here incorporated by reference. The ultrasound transducer(s) described in this document may be modified so that it is able to focus an ultrasound beam or spot in the crystalline lens instead of the ciliary body. In this respect, the transducer(s) may form a concave, convex or plane circular geometry (ex: disc or small height cylinder with a plane, concave or convex frontal surface) the size of which is less than or substantially the same as that of the lens. If a set of transducers is used, the transducers may be arranged according to a substantially circular geometry when viewed in an x, y plane (frontal plane) and may also be arranged axially (along perpendicular z-axis that passes by the two poles of the crystalline lens) with different axial positions relative to each other at least for some of them. In such a configuration, at least some of the transducers will be at different axial distances from the center crystalline lens which will make it possible to focus ultrasound beams on a 3D shape or zone inside the lens.

Also another focused ultrasound generator may be used such as the one described in EP 2 398 433 which is here incorporated by reference. The transducer arrangement may be annular shape with a single transducer or a set of transducers distributed among the circumference. The frequency of the ultrasound radiation may lie in the range from 1 kHz to 25 MHz, preferably between 500 kHz and 20 MHz. The ultrasound beam may be emitted in a pulsed mode or not.

The invention, either as an implant or through a non-invasive method for altering locally the flexibility and possibly the refractive index of the lens as in FIGS. 12A-F, makes it possible to increase the visual accommodative amplitude of an aged natural lens by more than 1 diopter and for instance up to 3 or 5 diopters. On average, an increase lying between 1.5 and 4.5 may be envisaged.

All that has been described above in connection with FIG. 9 and following may also be used for correcting any other optical disorders in a patient's eye.

The above-mentioned 3D model used in connection with simulation step S6 of FIG. 9 may be obtained through a computer system that will now be described with reference to FIGS. 13 to 17. To be noted that the following description concerns a computer (or computer-based) system and associated computer-based method that enable establishment or elaboration of a 3D human eye model. This model is capable of mechanically and optically simulating the behavior of a human eye. Such a simulation model may be used for any other purpose than that described with reference to FIG. 9.

A computer (or computer-based) system for simulating visual accommodation (hereinafter referred as "the system") comprises at least one processor and at least one computer-readable storage media. In an embodiment, the system includes a microcomputer whereas, in another embodiment, it includes a professional workstation, a server, a mainframe, a supercomputer or a combination of such systems. The computer-readable storage media of the system, for instance a memory, is encoded with instructions that, when executed by the processor, enable a simulation system for simulating visual accommodation, whose parameters, models, computations, results and advantages are described below.

As shown on FIG. 13, the system 100 comprises five main components, namely a geometry module 101, a physics module 102, a simulation engine 103, an output providing module 104, an update module 105 and an interface module 106.

The geometry module 101 allows to set a three-dimensional geometrical model of an eye. The three-dimensional geometrical model delineates volumetric boundaries of several physiological entities of an eye. The physiological entities whose volumetric boundaries are thus distinctively defined by the geometrical model are, preferably, the crystalline lens, the zonules, the ciliary muscle, the sclera, the cornea, the vitreous body and the aqueous humor. Accordingly, the geometrical model defined by the geometry module 101 results from an assemblage of several distinct geometries, each one relating to a specific physiological entity of an eye.

All physiological entities involved in the process of visual accommodation are defined by the geometrical model specified by the geometry module 101 of the system 100. As such, the geometry module 101 allows to faithfully transpose the geometry of a real eye and, therefore, it contributes to greater accuracy of the simulation results of visual accommodation which are provided by the system 100.

The crystalline lens as defined by the geometrical model is divided in four subparts, which are the nucleus, the lens cortex, the lens capsule and the lens epithelium. From a geometrical point of view, each subpart is defined as a solid generated by cross sectional continuous curves, forming a bi-convex aspheric and not necessarily regular domain. Each curve is the representation of a $5^{th}$ order polynomial I, where I is the considered plan of the cross section. The crystalline lens is thus defined as a set of four of such volumes nested together. The geometrical model further defines an offset of distance between each subpart along the crystalline lens polar axis With respect to the sclera and the cornea, the geometrical model defines the sclera's shape and the cornea's shape as a volume generated by an ensemble of $5^{th}$ order polynomial curves.

With respect to the zonules, since the zonular fibers form a complex web sustaining the lens, connecting it with the ciliary muscle, and linking the ciliary muscle to the sclera, the geometrical model defines three zonula groups (posterior, equatorial, anterior). Each group is made of two zonula rings delimiting the insertion thickness. The geometrical model further defines several intersections where each of these groups intersects with the crystalline lens and/or the ciliary muscle.

With respect to the ciliary muscle, which is a structure of multiple fibers orientation, the geometrical model defines its specific shape as bounded by a skin, which is defined through a generated central part of revolution from which are derived multiple discrete segments of extrusion.

The geometrical model further defines at least one area where the ciliary muscle is fixed to the sclera, points or areas at which it interacts with the zonules and further geometrical aspects designed to allow the ciliary muscle to slide on the choroid during the accommodation process.

The geometry module 101 interacts with the interface module 106 to generate a window of the graphical user interface provided by the interface module 106, in which a three-dimensional representation of the geometrical model is displayed.

The graphical user interface generated by the interface module 106 provides functionalities enabling data submission, including numerical and graphical inputs. Accordingly, the geometrical model managed by the geometry module 101 may be modified by means of graphical inputs performed directly on the three-dimensional representation displayed in the graphical user interface, thereby allowing a sort of "WYSIWYG—what you see is what you get" type of interaction. This feature is particularly advantageous in situations where, for instance, the geometrical model must be aligned to in-vivo measurements of real eyes' geometries. In this respect, the system 100 provides an improvement in terms of man-to-machine interaction, thereby enhancing its efficiency when used, for instance, in research & development or therapeutic environments.

Figure 14:
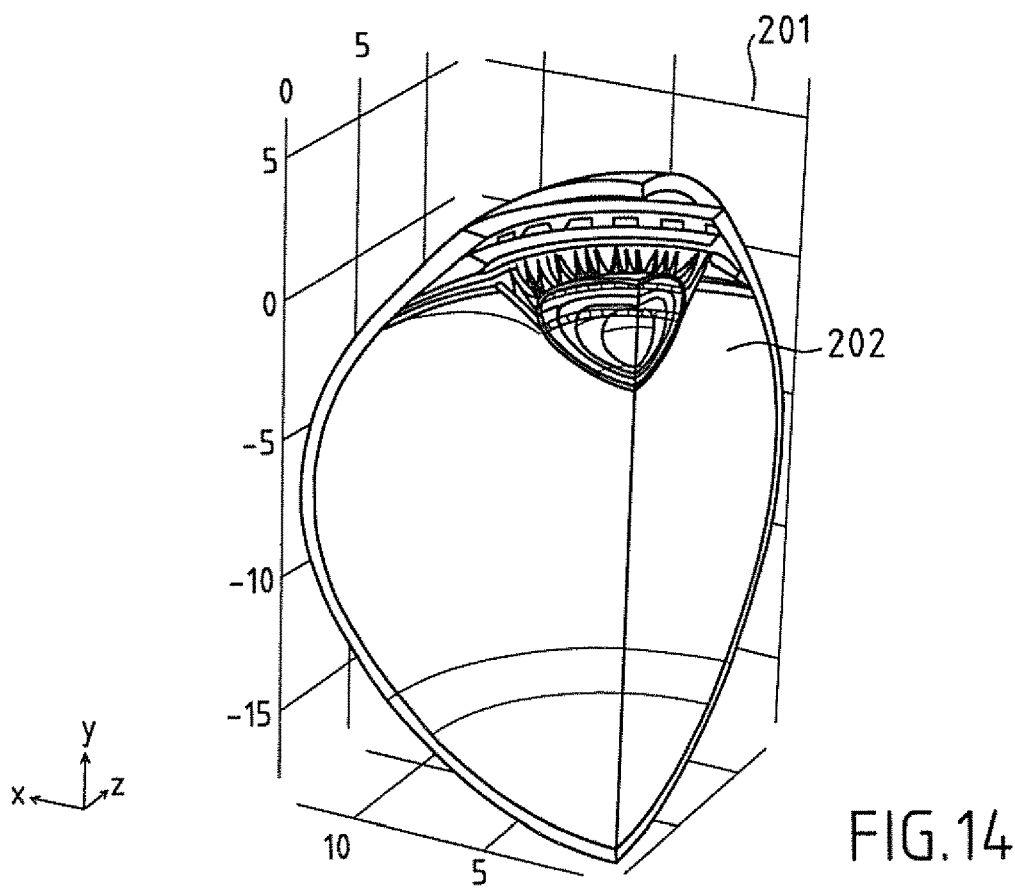
FIG. 14 is a schematic view of a window displayed in the graphical user interface of the system of FIG. 13.

FIG. 14 schematically depicts at least a part of a window 201 of the graphical user interface provided by the interface module 106, in which a partial three-dimensional representation 202 of the geometrical model is displayed.

The role of the physics module 102 is to define a physics-related environment in relation to the geometrical model managed by the geometry module 101. As such, it allows the simulation results provided by the system 100 to rely on a combination of geometry and physics, by means of a precise definition of mechanical and optical properties in relation to given eyes' geometries. To this end, the physics module 102 allows setting of numerous physics-related parameters to characterize optical and mechanical properties of, preferably, all parts defined by the geometrical model.

Advantageously, the physics module 102 processes data to assign mechanical and/or optical properties to specific points, areas or volumes defined by the geometrical model. Thus, the physics module 102 provides fine tuning capabilities for setting the physics-related environment, thereby contributing to the provision by the system of more accurate simulation results.

With respect to the mechanical properties of the crystalline lens, the physics module 102 allows to set a physics-related parameter that characterizes its stiffness. Preferably, the physics module 102 allows to set distinct physics-related parameters, some or all relating to stiffness, with respect to specific areas of the nucleus, the lens cortex, the lens capsule or the lens epithelium. Advantageously, a physics-related parameter may be set only for specific points, areas or volumes of those subparts.

Figure 15:
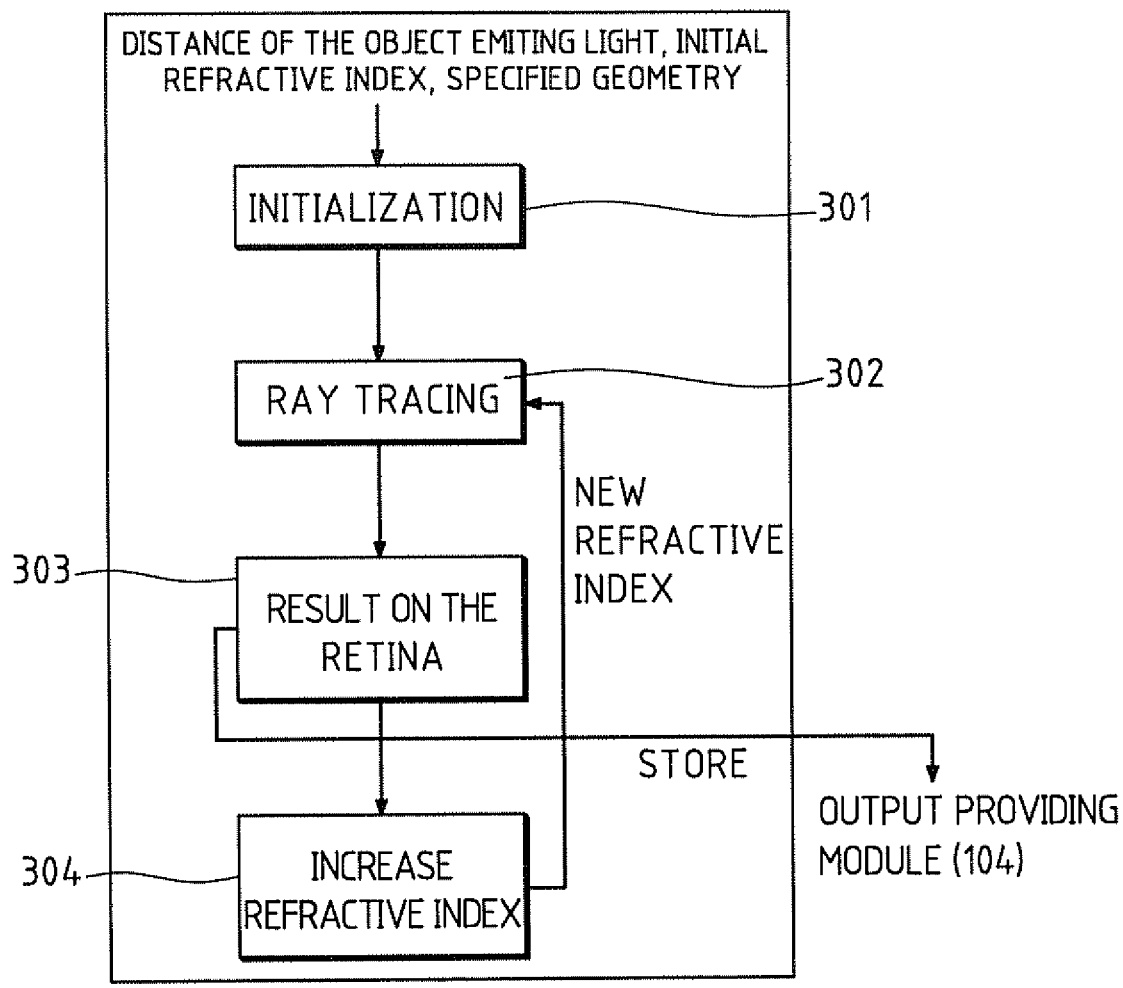
FIG. 15 is a schematic view of a process implemented by the system of FIG. 13.

With respect to the optical properties of the crystalline lens, the physic module 102 allows a physics-related parameter of refractive index to be set. Preferably, setting of the refractive index parameter involves determination of the refractive index parameter based on a computation of the sum of cumulated light received by the retina, for different concentric areas characterizing the sharpness of focus, when considering, for a given geometry, a situation where light is emitted by a point located one meter away from the cornea. This computation that may be performed by the physics module 102 in order to determine the refractive index parameter is depicted by FIG. 15.

In a step 301, the physics module 102 retrieves the geometrical model defined by the geometry module 101, a value characterizing the distance of the object emitting light and assigns an initial value to the refractive index parameter. In a step 302, the physics module 102 generates a ray tracing and, in a step 303, the physics module 102 determines a corresponding result on the retina by computing the cumulated light received by the retina. In a step 304, the physics module 102 increases the refractive index parameter by a pre-defined offset and repeats the steps 302 and 303 until a defined stop value of refractive index. Once it has performed those steps for several different values of refractive index, the physics module 102 sets the refractive index parameter by selecting the value which produces the sharpest result on the retina.

To be noted that the refractive index may take a single value or be a mathematical function that is defined by intervals (ex: nucleus, cortex etc.) or by zones that are created by an implant (ex: shell part and core part) or by electromagnetic treatment. The distribution of the refractive index by intervals is called a gradient of refractive index (GRIN). Examples of GRINs are provided on FIGS. 19B-F.

With respect to the mechanical properties of the sclera, the physics module 102 allows to set a physics-related parameter to characterize its stiffness, preferably by means of a linear material model.

With respect to mechanical properties of the zonules, the physics module 102 allows to set a physics-related parameter that characterizes the stiffness of its anterior, posterior and equatorial parts. Preferably, the physics module 102 allows setting of a physics-related parameter that characterizes an elongation level of the posterior part of the zonules.

With respect to mechanical properties of the ciliary muscle, the physics module 102 allows to set a physics-related parameter that characterizes its core's elasticity and its skin's rigidity. Moreover, the physics module 102 allows to set a physics-related parameter that characterizes weaknesses at some specific locations of the muscle's skin, thereby allowing to characterize the behavior of the muscle's skin which, during accommodation, changes its shape when submitted to the traction of the posterior part of the crystalline lens. Preferably, the physics module 102 also allows setting of a physics-related parameter that characterizes contraction and/or elongation level with respect to the whole ciliary muscle and/or with respect to only a part of it. Accordingly, the visual accommodation process may be simulated by means of modifications applied to the physics-related parameters characterizing stiffness of at least some parts of the ciliary muscle.

With respect to mechanical properties of the aqueous humor, the physics module 102 allows setting of a physics-related parameter that characterizes its dynamic viscosity, density or elasticity. Moreover, the physics module 102 allows to set several physics-related parameters that characterize fluidic properties of anterior and posterior chambers, inflow from the ciliary body at a constant mass flow rate and an outflow rate.

With respect to optical properties of the aqueous humor, the physics module 102 allows a physics-related parameter that characterizes its refractive index to be set.

With respect to mechanical properties of the vitreous body, the physics module 102 allows a physics-related parameter that characterizes its elasticity and/or an index of refraction to be set. Preferably, viscoelastic properties of the vitreous body are characterized by the physics-related module 102 via a physics-related parameter which is based on two Kelvin-Voigt model in chain with a damper.

With respect to optical properties of the vitreous body, the physics module 102 allows a physics-related parameter that characterizes its refractive index to be set.

Figure 16:
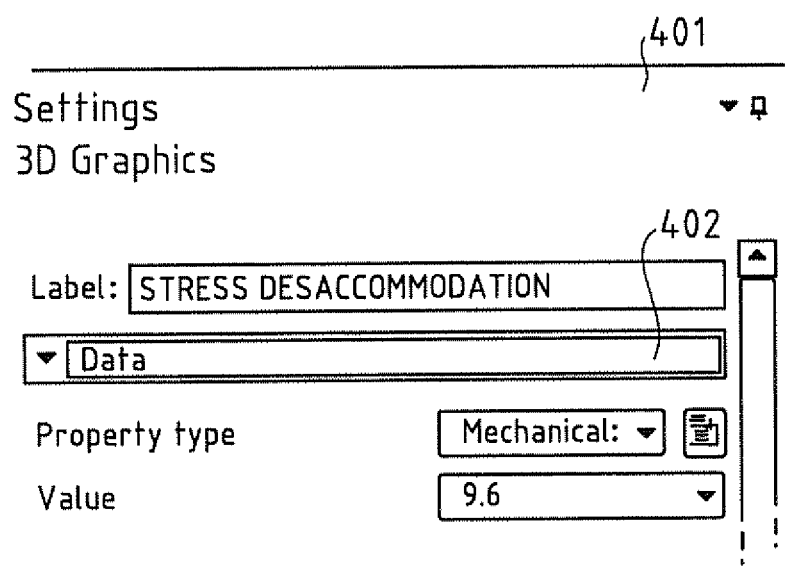
FIG. 16 is a schematic view of another window displayed in the graphical user interface of the system of FIG. 13.

In terms of man-to-machine interaction, the physics module 102 interacts with the interface module 106 to generate, as shown by FIG. 16, a window 401 of the graphical user interface provided by interface module 106. The window 401 includes at least input means 402 that may be operated to adjust all the physics-related parameters defined by the physics module 102. Alternatively, or cumulatively, the window 401 includes input areas to facilitate numerical inputs, thereby allowing also a "WYSIWYG" type of man-to-machine interaction. As mentioned above, the graphical user interface provides functionalities for management of any type of man-to-machine interactions. This applies to the window 401, which may thus allow graphical inputs to be submitted by means of pointing devices and numerical inputs to be specified by means of dedicated input areas.

Figure 17:
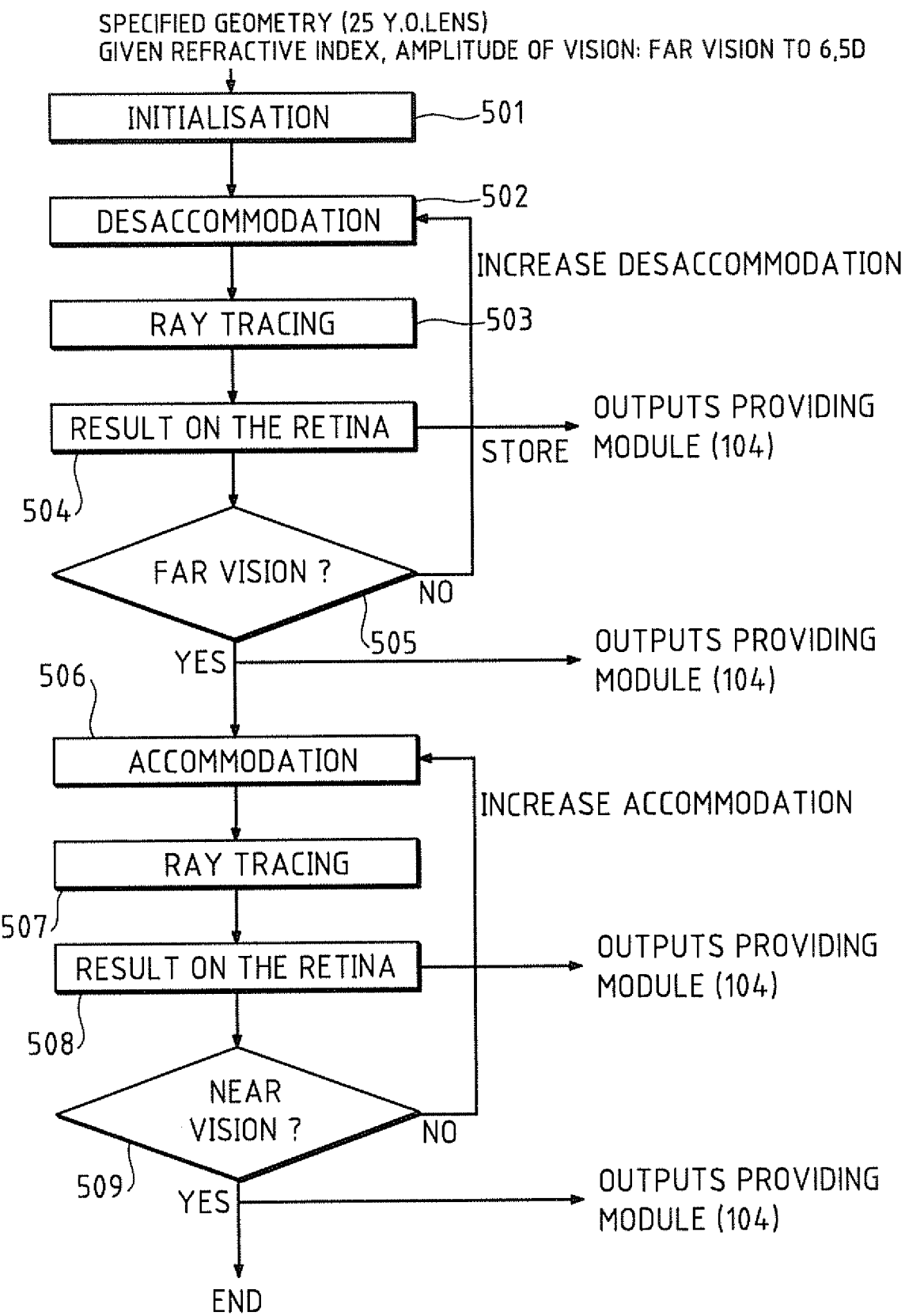
FIG. 17 is a schematic view of another process implemented by the system of FIG. 13.

The role of the simulation engine 103 is to combine the geometrical model defined by the geometry module 101 with the physics-related environment defined by the physics module 102. As such, the simulation engine 103 generates a simulation model which, to produce graphical or numerical results with respect to a process a visual accommodation, duly considers geometrical and physics-related aspects. An example of a process of combining geometrical and physics-related aspects that may be performed by the simulation engine 103 is depicted by FIG. 17.

In a first step 501, the simulation engine 103 retrieves from the geometry module 101 a geometrical model characterizing a young emmetropic eye, preferably a twenty-five years old eye. In parallel, the simulation engine 103 retrieves from the physics module 102 the refractive index parameter of the crystalline lens corresponding to the given geometry.

In a step 502, the simulation engine 103 operates the geometrical model to characterize a tension on the posterior part of the zonules, which induces a deformation of the crystalline lens and, with respect to the given geometry of a twenty-five years old eye, the simulation engine 103 determines the force needed to achieve far vision. Accordingly, during this step 502, the simulation engine 103 sets an initial value of tension applied on a posterior part of the zonules to achieve far vision. In a step 503, the simulation engine 103 generates a ray tracing and, in a step 504, it determines a corresponding result on the retina by computing the cumulated light received by the retina. In a step 505, the simulation engine 103 determines if far vision is achieved or not. If it is not the case, in order to characterize greater tension applied on the posterior part of the zonules, the simulation engine 103 increases the value of tension applied on the posterior part of the zonules using a pre-defined offset and steps 502-505 are repeated until the simulation engine 103 determines in step 505 that far vision is achieved. When the simulation engine 103 determines that far vision is achieved, it transmits the value of tension applied on the posterior part of the zonules to achieve far vision to the outputs providing module 104.

Then, in a step 506, considering the far vision achieved, the previous determined value of tension applied on posterior part of the zonules to achieve far vision remain identical, and the simulation engine 102 applies a first initial value of contraction of the ciliary muscle. In a step 507, the simulation engine 103 generates another ray tracing for a given distance of ray-emission corresponding to a close object and, in a step 508, it determines the result on the retina. Then, in a step 509, the simulation engine determines if near vision is achieved or not. If it is not the case, in order to characterize greater contraction value of the ciliary muscle, the simulation engine 103 increases the value of contraction applied on the ciliary muscle using a pre-defined offset and steps 506-509 are repeated until the simulation engine 103 determines in step 509 that near vision is achieved. When the simulation engine 103 determines that near vision is achieved, it transmits the value of contraction applied on the ciliary muscle to achieve near Vision to the outputs providing module 104.

By means of this process, the simulation engine 103 is thus able to determine the parameters of the tension and contraction characterizing an accommodation amplitude of a young eye. Moreover, considering the hypothesis that the efforts for visual accommodation remain similar for young and old people, the simulation engine 103 may for instance evaluate the accommodation amplitude of an old eye by applying the previously determined parameters of tension and contraction to the geometrical model and the physics related environment of an older eye.

The role of the output providing module 104 is to retrieve results data that are generated by the simulation engine 103 and to interact with the interface module 106 to present these results as numerical and graphical outputs.

The simulation results generated by the simulation engine 103 and retrieved by the outputs providing module 104 include, preferably with respect to all physiological entities defined by the geometrical model, data that relates to forces, mechanical stresses, deformations or displacements. With respect to optical domains, the results include data that relate to optical changes and, in relation to visual accommodation, the results retrieved by the outputs providing module 104 include at least data defining a value of accommodative amplitude. The outputs providing module 104 retrieves data from the simulation engine 103 and processes the data to feed the interface module 106. In this respect, the interface module 106 may present the results via one or more windows. Preferably, results are presented in a graphical or numerical form, the choice of format being made in accordance with a set of pre-defined formats which specifies, for each result that may be provided by the simulation engine 103, an appropriate format to be used.

A role of the update module 105 is to monitor user inputs and, if necessary, to update the geometrical model or to the physics-related environment accordingly. In this respect, the update module 105 continuously interacts with the interface module 106 so that, when the former is alerted by the latter that user inputs are submitted, it determines whether such inputs represent changes that apply to the geometrical model, so-called geometry-related changes, or to the physics-related environment, so-called physics-related changes. For instance, when the interface module 106 detects that user inputs are submitted via the three-dimensional representation 202 of the geometrical model displayed in window 201, it alerts the update module 105 that, in turn, modifies the geometrical model defined by the geometry module 101. In other words, numerical and graphical inputs are continuously monitored by the interface module 106 and processed in real-time by the update module 105 to update the simulation environment (geometry and/or physics). Thus, the update module 105, by allowing changes made to the simulation environment to be continuously monitored and processed by the system, provides automatic updating mechanisms which contribute to increase efficiency of the system.

Another role of the update module 105 is to retrieve data from remote data sources, for instance medical measurement devices or a medical imaging devices. As previously stated, the system 100 may indeed be part of a computerized therapeutic environment, in which it may be connected to medical devices from which, by means of functionalities provided by the update module 105, it may retrieve geometrical or physics-related data.

In such situations, the update module 105 is configured to interact with interfaces of those devices and it updates the geometrical model defined by the geometry module 101 or the physics-related environment defined by the physics module 104 in accordance with data that it retrieves from those data sources. Thus, by allowing for instance in-vivo data to be directly retrieved and processed by the system, the update module 105 also contributes to increase efficiency of the system 100, especially when it is used in such a computerized R&D or medical environment.

In a general manner, update module 105 is used in the computational modelling step S5 of FIG. 9 together with geometry module 101 and physics module 102 (mechanical and optical) to update the generic model and make it representative of the patient's eye. More particularly, update module 105 is configured to update the geometrical model hosted by the geometry module 101 and the physics-related environment stored by physics module 102 in accordance with data entered into the system.

The physics module 102 makes it possible to perform the calibration sub-step of step S5 of FIG. 9 and in particular to determine the refractive index as illustrated in FIG. 15 and described above. Also visual accommodation may be computed as illustrated in FIG. 17 and described above.

Update module 105 permanently controls any new input information/data in connection with a lens implant or, more generally, any eye surgical method. New input information/data may be provided by the surgeon through interface module 106. Update module 105 cooperates with the simulation engine 103 to simulate the mechanical and optical behavior of an implant in the model's patient eye (step S6 of FIG. 9).

In particular, simulation engine 103 may perform the computational steps of FIG. 17 based on the above new information/data and provides numerical and/or graphical outputs through outputs providing module 104. These outputs are then analyzed, e.g. by the surgeon, to determine if the lens implant or, more generally, any eye surgical method provides the desired results in terms of flexibility, visual accommodation and any other optical correction.

In contrast to most system for simulating visual accommodation, which often focus only on the role of the crystalline the lens, the system 100 addresses with a great level of details numerous physiological entities that are present in a real eye. Moreover, as explained above, the geometry of the eye may be controlled from measured data or whatever data that is entered, which allows the system 100 to be able to grasp most of the possible geometrical combinations that may be found in real eyes. The system 100 is thus more efficient when used, for instance, in a R&D or therapeutic environment because, in such a situation, simulation results are useful only if they are able to reflect in an accurate manner the physiological reality.

Figure 18:
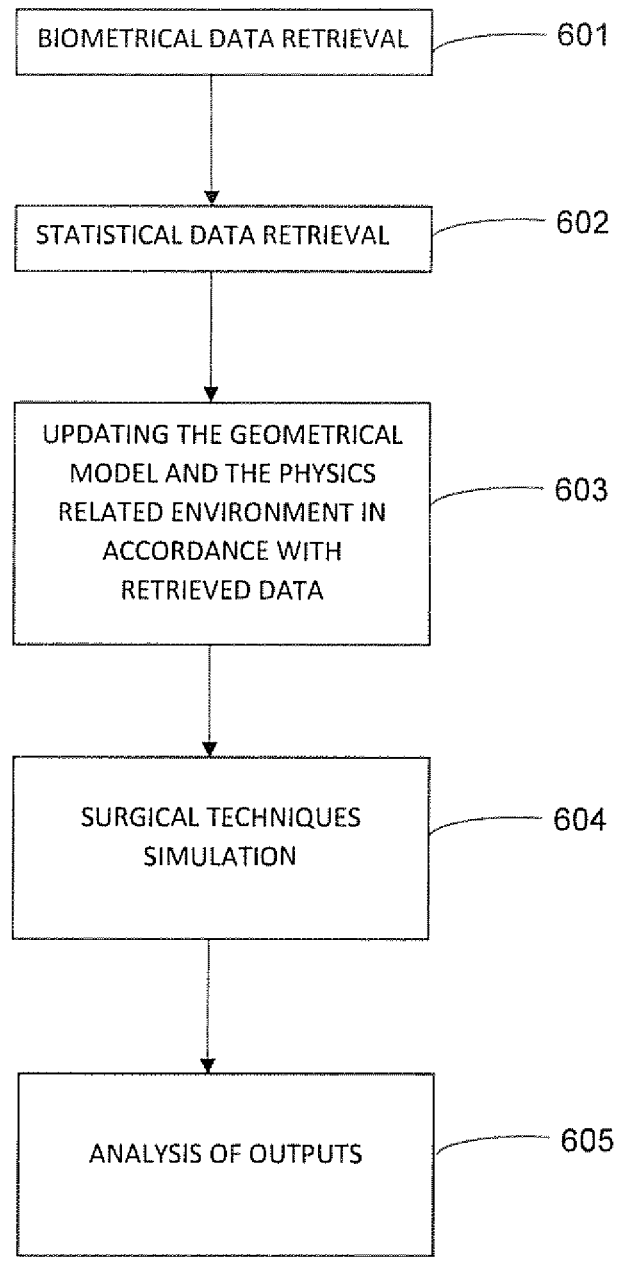
FIG. 18 is a schematic view that illustrates a possible application of FIG. 13 computer system in a therapeutic or surgical environment.

Independently from what has been described in relation with FIG. 9 the use of the computer system in a therapeutic environment may also be illustrated by FIG. 18. FIG. 18 depicts an example that shows how the system may be used as a tool in a process of corrective eye surgery, in particular within a surgical planning process. In such a process, the update module 105 first retrieves, in a step 601, biometrical data characterizing a patient's eye from a remote source such as a medical imaging device or any other appropriate system or instrument that may be used for gathering in-situ measurements of such physiological data. Then, in a step 602, the update module 105 retrieves also statistical data characterizing several physics-related parameters, for instance statistical data characterizing a refractive index parameter in relation to the patient's age. Such statistical data is stored in a dedicated database that is part of the system 100. Such data is built on the basis of studies performed on representative samples of patients, accumulated imaging and classified in accordance with several criteria such as age, ethnicity, gender, etc. Advantageously, the statistical data may be correlated to the patient to be treated by extracting from it mean values in relation to the patient's profile. Accordingly, following the step of data retrieval, step 602 may include an additional step of sorting the statistical data extracted from the database in relation to one or more characteristics that are specific to the patient to be treated, for instance the patient's age or the patient's gender. Then, in a step 603, as explained above, the update module 105 is configured to update the geometrical model hosted by the geometry module 101 and the physics-related environment managed by physics module 102 in accordance with the data that has been retrieved. Then, in a step 603, the physics module 102 may perform the computational procedure that has been described in relation to FIG. 15 to determine the best refractive index parameter. Alternatively, or cumulatively, step 603 includes a visual accommodation computation as described in relation to FIG. 17. Following this step, the geometrical model and the physics-related environment accurately reflect the anatomy of the patient's eye in terms of geometry and in terms of optical and mechanical properties before surgical treatment. Then, in a step 604, the surgeon provides inputs to the system which are meant to define surgical techniques that may be implemented. Those inputs are submitted via the interface module 106 and numerical or graphical outputs are computed by the simulation engine 103 via implementation of the computational steps that have been described in relation to FIG. 17. In a step 605, the outputs provided by the outputs providing module 104 are then analyzed in order to determine if, for instance, surgical techniques provide the desired result in terms of visual accommodation. This analysis may be performed either manually by the surgeon himself or automatically via an additional analysis module of the system 100 (not represented) that is configured to determine if a result fulfills certain predefined criteria, Then, through numerous iterations of steps 604 and 605, with respect to different surgical techniques that may be implemented, the surgeon is able to determine, for each patient, the best approach that must be followed in order to reach the desired result. In other terms, the system allows treatment's solutions to be investigated iteratively and results to be accurately forecasted and optimized without needing invasive steps to be performed.

Overall the computer system as described above is configured to receive data and output other data (either on a display assembly or interface or outside the system, e.g. the outputted transformed data may be transmitted to a distinct outside device or system). This computer system comprises computer programs that are stored on computer readable storage media and may be executed or run upon command or automatically. Execution of the programs causes execution or performance of steps of methods such as methods illustrated in FIGS. 15, 17 and 18. This also applies to some steps of the method illustrated in FIG. 9.

Figure 19A:
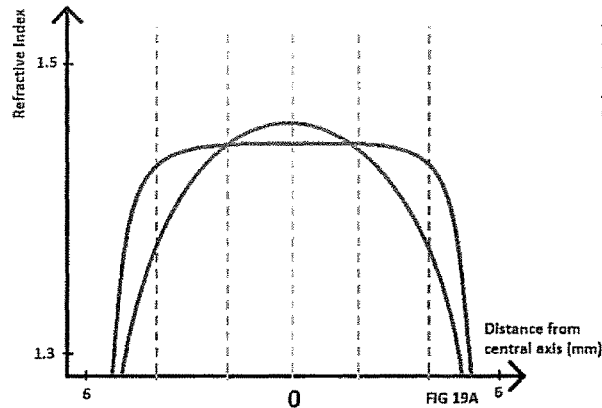
FIGS. 19A-F illustrate different gradients of refractive index.
Figure 19B:
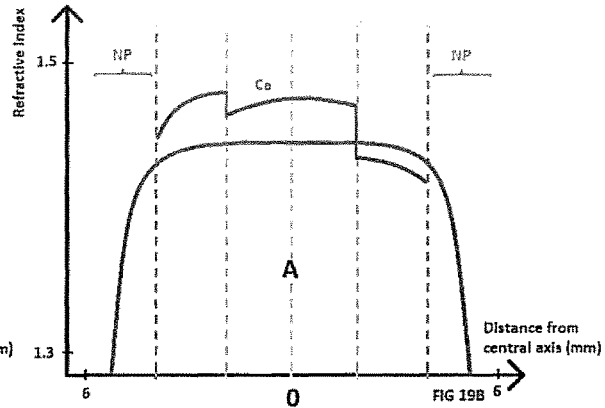
Figure 19C:
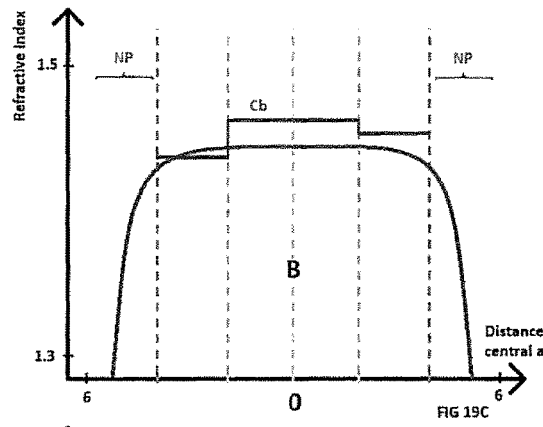
Figure 19D:
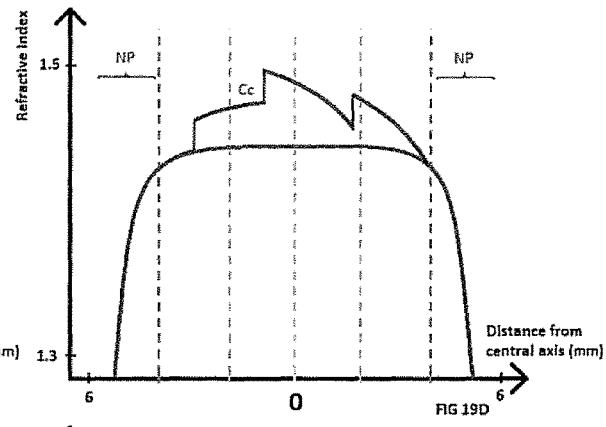
Figure 19E:
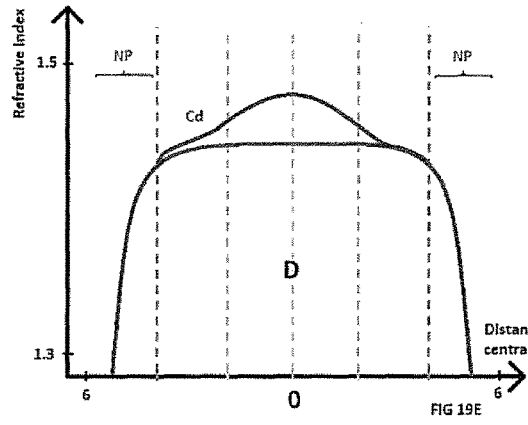
Figure 19F:
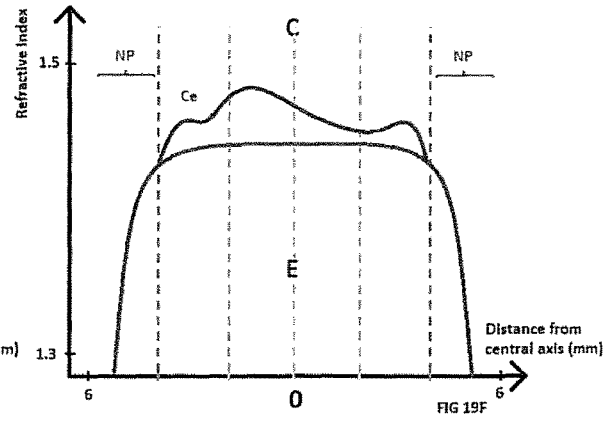

FIG. 19A illustrates the evolution or variation of the refractive index within a crystalline lens along an axis that passes by the center of the lens. Two representations are given, for a young person (dome-shaped curve) and an aged person (flat curve).

FIGS. 19B-F illustrate different examples of refractive index repartitions that may be obtained through treatment according to aspects of the invention. By way of example, an implant according to one of the above-described aspects of the invention and electromagnetic treatment as explained above may lead to such refractive index repartitions.

The following aspects are common to all FIGS. 19B-F:
the curve with a flat shape in the central part represents the refractive index curve of the aged patient's lens;
NP designates the peripheral zone of the lens that remains untreated or unmodified;
the vertical lines delineate the different zones: untreated zone in the periphery, cortical/shell zone, central/core zone;
the different curves located between the most two extreme vertical lines Ca, Cb, Cc, Cd, Ce represent the evolution/variation of the refractive index after treatment;
the different curves Ca, Cb, Cc, Cd, Ce are non axi-symmetrical since here this is a goal to achieve (although axi-symmetrical curves may be obtained in other embodiments);
any continuous curve may be more or less smoothed out.

Curve Ca shows discontinuities at the interfaces between the zones and a continuous gradient in each zone.

Curve Cb shows a stepped configuration with a continuity with the natural lens peripheral part.

Curve Cc shows continuities at the interfaces between the zones with a discontinuity in each zone.

Curve Cd shows a continuous gradient with different inflection points.

Curve Ce shows a continuous gradient with changes in the slopes and therefore different profiles in each zone.

Overall the curves have each a maximal value and an average value that are each greater than those before treatment (flat-shaped curve). To be noted that other values may alternatively be obtained, e.g. an average value that is less than that before treatment.

The representations of FIGS. 19B-F show several interfaces between zones. However, different interfaces may alternatively be chosen according to the type of implant (shell and core parts, a single implant etc.).

The representations of FIGS. 19B-F show refractive index curves after treatment that can be achieved per half-axis. For example, a left or right curve may be obtained separately and combined with another left or right curve respectively depending on the result to be achieved.

The illustrations of refractive index gradients of FIGS. 19B-F may vary according to different variant embodiments, taking over some of the principles of these Figures and possibly combining them.

To be noted that some aspects of the above detailed description may be completed if need be by any of general considerations as those mentioned above before the list of drawings.

The invention claimed is:

1. An intra capsular lens implant intended to wholly fill in the capsular bag in an eye, wherein the intra capsular lens implant comprises;

a core part and a shell part surrounding the core part, the intra capsular lens implant having a longitudinal axis corresponding to a polar axis of the intra capsular lens implant, wherein the core part comprises an anterior part and a posterior part that extend axially along the polar axis, the anterior part having an anterior pole (A) located on the polar axis and the posterior part having a posterior pole (E) located on the polar axis, the anterior part and the posterior part extending each radially relative to the polar axis on either side thereof, the anterior part and the posterior part having each two portions located on both sides of the polar axis respectively when viewed in the sagittal plane, each portion of the anterior part having a radial extension that increases from the anterior pole to a point where the anterior part ends and the posterior part begins, each portion of the posterior part having a radial extension that decreases from the point where the posterior part begins to the posterior pole, an outer outline of each portion of the anterior part forming a curve having a radius of curvature that is greater at the anterior pole than at the point, both the core part and the shell part being made of one or more materials that have elastic or visco-elastic and cohesive properties in a solid state, or the shell part being made of said one or more materials that have elastic or visco-elastic and cohesive properties in a solid state and the core part being made of a fluid that have elastic or visco-elastic and cohesive properties, both the one or more materials and the fluid having a refractive index that is suitable for being used in a crystalline lens, wherein each portion of the posterior part has an outer outline that forms a continuous curve between the point and the posterior pole when viewed in a sagittal plane, wherein the outer outline of each portion of the posterior part comprises two convex side surfaces separated by a concave central surface, wherein the shell part is made of a material of which the shear modulus is greater than that of the core part.

2. The intra capsular lens implant of claim 1, wherein the shell part is more rigid than the core part.

3. The intra capsular lens implant of claim 1, wherein the refractive indices of both the shell part and the core part are defined so as to establish a gradient of refractive index.

4. The intra capsular lens implant of claim 1, wherein the anterior part has a convex shape when viewed in a sagittal plane.

5. The intra capsular lens implant of claim 1, wherein the outer outline of each portion of the posterior part includes two points, respectively, located on the curve between the point, respectively, and the posterior pole and that form two inflexion points for the curve.

6. The intra capsular lens implant of claim 1, wherein the shell part has a shear modulus of 5 kPa to 10 kPa, and the core part has a shear modulus greater than 10 Pa and less than 2 kPa.

* * * * *